United States Patent [19]

Ballenegger et al.

[11] Patent Number: 4,644,011

[45] Date of Patent: Feb. 17, 1987

[54] PHARMACEUTICAL PREPARATIONS CONTAINING (+)-CYANIDAN-3-OL DERIVATIVES, THE USE THEREOF, NOVEL SUBSTITUTED (+)-CYANIDAN-3-OL DERIVATIVES, AND PROCESSES FOR PRODUCING THEM

[75] Inventors: Marc E. Ballenegger, Gimel; Christian G. Rimbault, Grand-Lancy; Alban I. Albert, Grand-Saconnex; André J. Weith, Signy; Pierre Courbat, Nyon, all of Switzerland; Robert G. Tyson, Clwyd, England; Derek R. Palmer, Wirral, England; David G. Thompson, Clwyd, England

[73] Assignee: Zyma SA, Nyon, Switzerland

[21] Appl. No.: 754,181

[22] Filed: Jul. 9, 1985

Related U.S. Application Data

[63] Continuation of Ser. No. 499,647, May 31, 1983, abandoned.

[30] Foreign Application Priority Data

Jun. 1, 1982 [GB] United Kingdom ............... 8215867

[51] Int. Cl.$^4$ ............................................ A61K 31/35
[52] U.S. Cl. .................................... 514/456; 514/316; 549/399
[58] Field of Search ............... 549/399; 546/187, 196, 546/197; 514/456, 422, 316, 321, 320, 210, 212, 183

[56] References Cited

U.S. PATENT DOCUMENTS 4,166,861  9/1979  Bonati et al. ................. 549/399
4,255,336  3/1981  Albert et al. .................. 549/399

OTHER PUBLICATIONS

Weinges, K. et al., Chem. Ber., vol. 99 (11) pp. 3707–3711 (1966).
Weinges, K. et al., Ann. Chem. vol., 714 pp. 193–204 (1968).
Weinges, K. et al., Justus Lielig's Annalen Chem, vol. 726, pp. 114–124 (1969).
Hundt, H. et al., J. Chem. Soc. Perkin I, pp. 1227–1234 (1981).
McGraw, G. W., J. Chem. Soc. Perkin I, pp. 973–978 (1982).
Kiatgrajai et al., J. Org. Chem., vol. 47, pp. 2913–2917 (1982).
Hillis et al., J. Appl. Chem., pp. 474–482 (9/9/59).

*Primary Examiner*—Nicky Chan
*Attorney, Agent, or Firm*—Michael W. Glynn; Irving M. Fishman

[57] ABSTRACT

Pharmaceutical preparations containing (+)-cyanidan-3-ol derivatives of the formula I

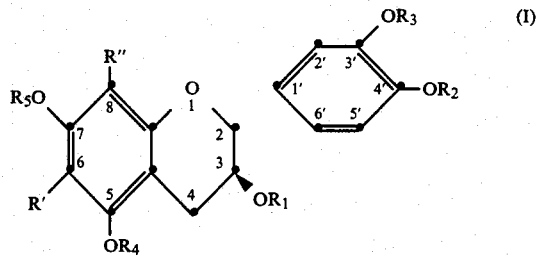

wherein R' and R" are hydrogen, an unsubstituted or substituted hydrocarbon radical, or heterocyclic radical, halogen, formyl, free or functionally modified carboxyl, free or etherified or esterified hydroxyl, free, etherified or oxidized mercapto, unsubstituted or substituted sulfamoyl, acyl or unsubstituted or substituted amino, where however R' and R" cannot both be hydrogen simultaneously, and $R_1$, $R_2$, $R_3$, $R_4$ and $R_5$ are each hydrogen or an unsubstituted or substituted hydrocarbon radical, and $R_2$ and $R_3$ together can also be an unsubstituted or substituted methylene group, and $R_1$ also an acyl group or an amidated carboxyl group; and therapeutically applicable salts of these compounds, as well as new compounds of these preparations.

These pharmaceutical preparations are particularly valuable for treating liver and venous diseases.

14 Claims, No Drawings

PHARMACEUTICAL PREPARATIONS CONTAINING (+)-CYANIDAN-3-OL DERIVATIVES, THE USE THEREOF, NOVEL SUBSTITUTED (+)-CYANIDAN-3-OL DERIVATIVES, AND PROCESSES FOR PRODUCING THEM

This application is a continuation, of application Ser. No. 499,647, filed May 31, 1983, now abandoned.

The invention relates to pharmaceutical preparations containing 6- and/or 8-substituted (+)-cyanidan-3-ol derivatives and to the therapeutic use thereof.

It has been found that 6- and/or 8-substituted (+)-cyanidan-3-ol derivatives have valuable pharmacological properties.

The invention relates therefore in particular to pharmaceutical preparations containing (+)-cyanidan-3-ol derivatives of the formula I

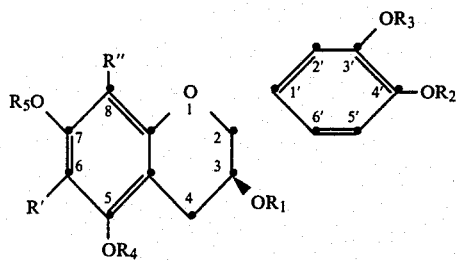

wherein R' and R" are hydrogen, an unsubstituted or substituted hydrocarbon radical, or heterocyclic radical, halogen, formyl, free or functionally modified carboxyl, free or etherified or esterified hydroxyl, free, etherified or oxidized mercapto, unsubstituted or substituted sulfamoyl, acyl or unsubstituted or substituted amino, where however R' and R" cannot both be hydrogen simultaneously, and $R_1$, $R_2$, $R_3$, $R_4$ and $R_5$ are each hydrogen or an unsubstituted or substituted hydrocarbon radical, and $R_2$ and $R_3$ together can also be an unsubstituted or substituted methylene group, and $R_1$ also an acyl group or an amidated carboxyl group; and to therapeutically applicable salts of these compounds.

Lower radicals in the following are in particular those having up to 7, especially up to 4, carbon atoms.

An unsubstituted or substituted hydrocarbon radical R', R", $R_1$, $R_2$, $R_3$, $R_4$ and $R_5$ is for example: an aliphatic, cycloaliphatic, cycloaliphatic-aliphatic, aromatic, aromatic-aliphatic or heterocyclic-aliphatic radical.

An aliphatic hydrocarbon radical, which is unsubstituted or substituted, is especially an alkyl as well as an alkenyl or alkynyl radical, in particular a lower alkyl as well as lower-alkenyl or lower alkynyl radical. Substituents of aliphatic hydrocarbon radicals are for example: free, esterified or etherified hydroxyl groups, free or etherified mercapto groups, such as lower alkanoyloxy, lower alkoxy or lower alkenyloxy groups, loweralkylthio, lower alkylsulfinyl groups, halogen or nitro and also free of esterified carboxyl groups, such as lower alkoxycarbonyl.

Lower alkyl groups are for example: methyl as well as ethyl, n-propyl, isopropyl, n-butyl, isobutyl, sec-butyl, tert-butyl, n-pentyl, isopentyl, neopentyl, n-hexyl, isohexyl or n-heptyl groups; lower alkenyl groups are for example: vinyl, allyl, 1-propenyl, isopropenyl, 1- or 2-methylallyl or 2- or 3-butenyl groups, and lower alkynyl groups are for example: propargyl or 2-butynyl groups. Substituted lower alkyl groups are for example: the nitro-lower alkyl groups, the hydroxy-lower alkyl groups, the trifluoromethyl groups, the hydroxycyano-lower alkyl groups, the hydroxyamino-lower alkyl groups, the lower-alkylthio-lower-alkyl groups, the acylalkyl groups or a free or esterified carboxy-lower-alkyl groups, for example a lower-alkoxycarbonyl-lower-alkyl group, for example methoxycarbonylethyl group, an unsubstituted or substituted imino-lower-alkyl group, such as a free or esterified hydroxyimino-lower alkyl group, a lower-alkylimino- or unsubstituted or substituted phenylimino-lower-alkyl group, an acyloxyimino-lower-alkyl group, di-lower-alkylimmonio-lower-alkyl an amino-lower-alkyl group, a di-lower-alkylamino-lower-alkyl group, or a lower-alkyleneamino-lower-alkyl group, for example a pyrrolidino- or piperidino-lower-alkyl group. A further possible substituted lower alkyl group is the lower alkyl group substituted by a 2,2-di-lower-alkyl-4,6-dioxo-1,3-dioxan-5-ylidene group, such as [(2,2-dimethyl-4,6-dioxo-1,3-dioxan-5-ylidene)]-methyl. Substituted lower alkenyl groups are for example free or esterified carboxy-lower-alkenyl groups, nitro-lower-alkenyl groups, lower alkyl-sulfinyl-lower-alkenyl, lower alkyl-sulfonyl-lower-alkenyl or aryl or lower-alkylthio-lower-alkenyl groups.

An unsubstituted or substituted cycloaliphatic or cycloaliphatic-aliphatic radical is for example a mono-, bi- or polycyclic cycloalkyl or cycloalkenyl radical or a cycloalkyl- or cycloalkenyl-lower-alkyl or -lower-alkenyl radical, wherein the cycloalkyl radical contains up to 12, for example 3–8, particularly however 3–6, ring carbon atoms, whilst a cycloalkenyl radical has for example up to 12, preferably however 5–6, carbon atoms and one or two double bonds. The aliphatic part of a cycloaliphatic-aliphatic radical can contain up to 7, but preferably up to 4, carbon atoms. The stated cyclic radicals can be, if desired, mono-, di- or polysubstituted, in a manner analogous to that in the case of the aromatic radicals given below.

An unsubstituted or substituted aromatic hydrocarbon radical is for example a monocyclic, bicyclic or polycyclic aromatic radical, such as the phenyl or naphthyl radical, which can be mono-, di- or polysubstituted. These radicals are preferably substituted by a free or esterified carboxy group, such as methoxycarbonyl, by hydroxyl or halogen, such as bromine or fluorine, or by lower alkyl, for example methyl, or by lower alkoxy, such as methoxy, or by a nitro group or by an unsubstituted or substituted amino group, for example the dimethylamino group or methylene dioxy group.

An unsubstituted or substituted aromatic-aliphatic hydrocarbon is for example an aliphatic hydrocarbon radical carrying up to 3 mono-, bi- or polycyclic aromatic radicals, which can also be substituted. It is in particular phenyl-lower-alkyl and also phenyl-lower-alkenyl or phenyl-lower-alkynyl. These radicals can, if desired, be mono-, di- or polysubstituted in the aromatic part and also in the aliphatic part.

A heterocyclic radical as such or in a heterocyclic-aliphatic group is especially a monocyclic radical. It can however also be bicyclic or polycyclic, and is in particular an aza- thia-, oxa-, thiaza-, oxaza- or diaza-cyclic radical, which is saturated or unsaturated, for example of aromatic character, and preferably contains 2–7 ring carbon atoms. These radicals can be mono-, di- or polysubstituted in the cyclic part as indicated for aromatic radicals above. The aliphatic radicals in a heterocyclic-aliphatic radical can have the meaning given above for the aliphatic part of the cycloaliphatic- or aromatic-aliphatic radicals.

Halogen atoms denoted by R' and R" are in particular fluorine, iodine and especially bromine: they can however also be chlorine atoms.

Free or functionally modified carboxyl is for example carboxy, esterified carboxyl, especially lower-alkoxycarbonyl, such as methoxycarbonyl or ethoxycarbonyl, amidated carboxyl, particularly carbamoyl which is free or substituted by alkyl, by di-lower-alkylaminoalkyl or by phenyl which is unsubstituted or for its part substituted by halogen, lower alkyl or lower alkoxy, and also the cyano group.

Esterified or etherified hydroxyl groups or etherifed mercapto groups are in particular lower alkoxy, also substituted lower alkoxy, for example by halogen, hydroxyl, mono- or di-lower-alkylamino or epoxy; they are also lower-alkenyloxy, cycloalkyloxy, phenyloxy, phenylalkoxy or lower alkoxy substituted by mono-aza, mono-oxa- or mono-thia-monocycles of aromatic character, such as pyridyl-lower-alkoxy, furyl-lower-alkoxy or thienyl-lower-alkoxy, lower-alkylthio, phenylthio or phenyl-lower-alkylthio, trifluoromethylmercapto, lower-alkoxy-carbonyloxy, lower alkylthiocarbamyloxy, di-lower-alkylcarbonyloxy or lower-alkanoyloxy, including formyloxy, lower-alkanoylthio or unsubstituted or substituted benzoyloxy, for example unsubstituted or further substituted hydroxybenzoyloxy or benzoylthio.

The acyl radicals of an aliphatic carboxylic acid are in particular acyl radicals of alkanecarboxylic acids, especially lower-alkanecarboxylic acids of lower-alkanedicarboxylic-acids, but also of alkenecarboxylic acids, particularly of lower-alkenecarboxylic acids or lower-alkenedicarboxylic acids, and also of substituted lower-alkanecarboxylic acids, such as trifluoroacetic acid.

The acyl radicals R', R" and $R_1$ of cycloaliphatic, cycloaliphatic-aliphatic, aromatic, aromatic-aliphatic carboxylic acids have, both for the ring and for the optionally present aliphatic part, the above-given meaning of the corresponding hydrocarbon radicals. They can also carry substituents, for example hydroxyl, halogen, lower alkyl and also lower alkoxy. An aromatic acyl radical is for example the benzoyl radical.

An unsubstituted or substituted amino group can be a primary, secondary or tertiary amino group. In the two last-mentioned amino groups, the nitrogen atom can carry as substituents unsubstituted or substituted aliphatic, cycloaliphatic, cycloaliphatic-aliphatic, aromatic and also araliphatic hydrocarbon radicals. Two substituents taken together can however also be an unsubstituted or substituted bivalent aliphatic hydrocarbon radical, for example a lower alkylene radical or lower alkenylene radical, in which the carbon atoms of the chain can be interrupted by a hetero atom, for example oxygen, sulfur or unsubstituted or substituted nitrogen.

Secondary or tertiary amino groups are for example: lower-alkylamino or di-lower-alkylamino groups, such as methylamino, dimethylamino, ethylamino, diethylamino, n-propylamino, di-n-propylamino, isopropylamino, di-isopropylamino or di-n-butylamino. Hydroxyl-substituted lower-alkylamino or di-lower-alkylamino groups, in which the hydroxyl group is separated from the nitrogen atom by at least 2, preferably by 2 or 3, carbon atoms, are for example: the 2-hydroxyethylamino, N-(2-hydroxyethyl)-N-methylamino or di-(2-hydroxyethyl)-amino group; cycloalkylamino or N-cycloalkyl-N-lower-alkylamino are for example the cyclohexylamino or N-cyclopentyl-N-methylamino groups.

Phenyl-lower-alkylamino or N-phenyl-lower-alkyl-N-lower-alkylamino groups are for example the benzylamino or N-benzyl-N-methylamino group.

Lower-alkyleneamino having 3 to 8, preferably 5 to 7, ring members is for example: pyrrolidino, 2,5-dimethylpyrrolidino, piperidino, 2-methyl-piperidino, 3-ethylpiperidino, hexahydro-1H-azepino or octahydroazocino. Lower-alkenyleneamino, preferably having 5 to 7 ring members, is for example 2,5-dihydro-1H-pyrrol-1-yl and 1,2,3,6-tetrahydro-1-pyridyl. Mentioned as azaalkyleneamino having 6 to 8, preferably 6, ring members, in which the azanitrogen atom is unsubstituted or preferably substituted by for example lower alkyl, hydroxy-lower-alkyl, phenyl, phenyl-lower-alkyl or pyridyl, and is separated at least by 2 carbon atoms from the amino-nitrogen atom, are for example piperazino, 4-methylpiperazino and 4-(2-hydroxyethyl)-piperazino.

To be mentioned as secondary or also as tertiary amino groups in this connection are also amino groups substituted by arylamino or arylimino groups, for example phenylhydrazino or phenylazo or lower alkylamino or lower alkylimino groups, for example methylhydrazino or methylazo.

Substituents of the methylene group which can be formed by $R_2$ and $R_3$ together, are in particular unsubstituted or substituted hydrocarbon radicals, as have been described above and is for example biphenyl-2,2'-ylene and when including the methylene group for example fluoren-9,9-ylidene.

The compounds of the pharmaceutical preparations according to the present invention possess valuable pharmacological properties. They show in particular an interesting activity in the prevention of necrosis and hepatic fibrosis and in addition inhibit lipoperoxidation. They also possess immunomodulating and antiinflammatory properties and can inhibit the release of lysosomal enzymes by increasing the stability of lysosomal membranes. They can further influence the vascular permeability and tonus. They can also modify the viscoelasticity of mucus secretion and stimulate the mucociliary transport in bronchia.

They are useful in the treatment of hepatic diseases such as acute hepatitis (viral, alcoholic, toxic), steatosis, chronic hepatitis and cirrhosis, particularly those of alcoholic origin.

Modification of experimental hepatitis induced by galactosamine, carbon tetrachloride or ethyl alcohol can be demonstrated in rats pre-treated with these compounds, either orally or intraperitoneally in doses ranging from 25 to 200 mg/kg in acute or chronic administration either in preventive or curative therapy. In acute studies, the animals are sacrificed 24 or 48 hours after administration of the toxic agent and hepatic function is measured by the following tests:

BSP clearance
plasma level of bilirubin
plasma level of transaminase
triglyceride level
total hepatic lipids.

In the chronic studies, hepatic collagen level is measured in addition to the above-mentioned parameters.

Typical results obtained in the acute galactosamine hepatitis of the rat are shown in the following table.

| substance | example No. | DE 50% ASAT* (μmoles/kg) |
|---|---|---|
| 8-hydroxyiminomethyl-(+)-cyanidan-3-ol | 90 | 140,6 |
| 6,8-dibromo-(+)-cyanidan-3-ol | 66 | 131,7 |
| 8-[2-(acetoxymethylthio)ethenyl]-3,5,7,3',4'-penta-O—benzyl-(+)-cyanidan-3-ol | 49-50-51 | 127,0 |
| 8-n-butyl-(+)-cyanidan-3-ol | 8 | 126,8 |
| 8-n-propyl-3-O—benzyl-(+)-cyanidan-3-ol | 6 | 118,5 |
| 6,8-di-(2-methylbenzyl)-(+)-cyanidan-3-ol | 20 | 98,1 |
| 8-tertiobutoxy-3,5,7,3',4'-penta-O—benzyl-(+)-cyanidan-3-ol | 119 | 53,5 |
| 8-trifluoroacetyl-3-O—benzyl-(+)-cyanidan-3-ol | 132 | 47,6 |
| 8-formyl-3-O—palmitoyl-(+)-cyanidan-3-ol | 77 | 11,3 |

*DE 50% ASAT dosage (in μmoles/kg) which induces a 50% reduction of the elevated plasma level of transaminase ASAT of the galactosamine intoxicated rats.

The effect on normal or pathological metabolism of the hepatocytes of rats kept alive can be demonstrated on isolated rat hepatocytes using the techhique of Berry & Friend, [J. Cell. Biol. 43, 506–520 (1969)] by incubating them in 2 ml Krebs-Ringer physiological solution in the presence of one of the compounds in quantities ranging from 0.1 to 1 mg/ml and with the addition of different hepatotoxic substances. On the other hand, the inhibition of lipoperoxidation by carbon tetrachloride can be demonstrated using the method of Comporti, Sacconi and Danzani, [Enzymologia, 28, 185–203 (1965)], and the intensity of lipoperoxidation in the presence of these new substances in concentrations varying between 5 and 50 μg per 4 ml is measured by quantitating the amount of malonic dialdehyde formed.

These compounds are also useful in the treatment od diseases involving an alteration of the organisms immunological response, such as all recurrent or prolonged viral infections: as for example hepatitus due to both virus B and non-A-non-B, or recurrent herpes, or for the treatment of diseases in which a stimulation of the organisms defence mechanisms may bring about healing or improvement of the patient's condition. This is particularly the case in viral, bacterial or parasitic infections, cancerous affections and the entire group of autoimmune diseases such as, for example, rheumatoid polyarthritis.

Immunomodulating properties of these compounds are demonstrated not only in neoplastic models but also by means of current immunological studies. Thus, the detection of these valuable immunomodulating properties is possible by using the leukemia L1210 Ha model in three types of experiments in mice. For example, isogenous CD2F1 mice are treated on day 0 with $10^7$ irradiated L1210 Ha cells and inoculated on day 14 with varying amounts of living cells possessing the same isogenous leukemia. The effect of these compounds, which are administered before and after inoculation, is demonstrated by an increased life span and a higher number of survivors on day 30. In addition, CD2F1 mice are inoculated with $10^5$ L1210 Ha cells and injected the following day with $10^7$ irradiated tumor cells. The compounds in question are administered before and after inoculation. The effect of these compounds, administered as above, is highly positive, as they increase both the length of life and the number of survivors at 60 days. Also, additional effects in animals previously immunodepressed by doses of 150 mg cyclophosphamide per kg confirm these results because they show that the animals' reactivity was intact. Finally CD2F1 mice transplanted with $10^5$ L1210 Ha cells, then treated the following day with Adriamycin, provide the same evidence of the beneficial effects of these compounds, when these are administered at dose range between 10 and 500 mg/kg.

These compounds possess a beneficial effect not only on ascitic tumours or on leukemia, but also on a solid tumour, i.e. the Lewis Lung (3LL) carcinoma of mice. As a matter of fact, this neoplastic model is considered by E.O.R.T.C. as that which resembles most closely human tumours. The compounds show positive results in significative manner in three series of studies. The compounds are administered for 10 days to C57 BL/6 mice infected with isogenous tumour 3LL. They are also given after treatment with methyl CCNU (methyl lomustine) in a dose range between 10 and 500 mg/kg to animals with tumour. They act also by limiting the development of metastases when the primary tumour has been removed surgically.

These compounds possess also immunostimulating activity. Thus their pharmaceutical potential has been proved in in-vivo studies by showing their ability to increase the cytotoxic capacity of purified macrophages toward cancerous cells. In fact, these macrophages, whose capacities have been appreciably increased by these substances, are believed to play an important role in both antitumoral resistance and control of immunological reactivity.

These compounds also have clearly demonstrated their therapeutic potential by showing without any possibility of doubt their positive effect on antibody production in non-neoplastic conditions which proves that their effect is in fact due to the host's reactivity. When CD2F1 mice are injected with $10^8$ sheep erythrocytes (SRBC) or with 0.5 μg polysaccharide of pneumococci S.III, the number of spleen cells capable of producing specific antibodies is significantly increased as it can be shown in the haemolytic plaque assay according to Jerne & Nordin. The antibodies are measured by peak responses either after single or repeated injections of one of these compounds.

Finally, as these compounds stabilize lysosomal membranes, potentiate the cytotoxic capacity of macrophages and decrease vascular permeability, they are useful for the treatment of disease states such as acute and chronic bronchitis in which the existing pathology of hypersecretion is complicated both by chronic inflammatory reactions and recurrent infections.

These compounds modify the viscoelaticity of mucus secretion, they stimulate the mucociliary transport in bronchi and they relaxe smooth muscles of bronchi. These properties make the compounds useful for the treatment of diseases of the respiratory tract, as for example chronic bronchitis.

The modifaction of viscoelasticity of mucus samples by these compounds is measured with a microrheometer.

The mucus is obtained from fresh pig's stomach scrapings and is purified biochemically before use. The test compounds are dissolved in specific solvants, distilled water, phosphate buffer, methanol mixture, or in DMSO (dimethylsulphoxide). 50 mg aliquotes of mucus with 5–10 μl of the test solution are added. The samples are mixed, centrifuged and incubated for 30 min. for interaction to take place. The samples are then loaded into the cell of an oscillating sphere magnetic microrheometer and a 200 μm iron sphere is placed centerally in the sample which is allowed 5 minutes for relaxation to take place. The rheological behaviour is evaluated at 25° C. over the frequency range of 0.1 to 20 Hz.

The stimulation of mucociliary transport is demonstrated with pharmacological model of frog palate. In this system, the speed of transport of particles by the ciliated epithelium of frog plate is measured.

By adding solutions of compounds to be tested (0.1–1 mg/hl) on the frog palate an increase in the speed of transport is measured.

The relaxing effect of these compounds on the smooth muscles of bronchi is demonstrated by the protection afforded by these compounds against the broncho-spasm induced by histamine aerosol in Guinea-pigs. Pretreatment of Guinea-pigs by i.p. route with the new compounds (10–100 mg/kg) allows the animals to resist more than 5 minutes to the histamine aerosol; control animals do not resist more than 1 min. and 30 sec.

These compounds are also useful for the treatment of venous or arterial circulatory diseases.

The antiinflammatory, vasculotropic and protective properties of the compounds towards the connective tissue may be demonstrated in the following studies:

(1) At doses varying between 100 and 500 mg/kg, by parenteral or oral administration, they are able to reduce oedema caused by galactosamine, by heat and by stasis. Even more important, these beneficial effects are seen in the absence of any central haemodynamic activity. The compounds favourably modify vascular reactivity in terms of both micro- and macro-circulation. They are also capable of improving peripheral blood circulation (legs). Finally, these substances counteract the toxic effects of histamine in cultures of endothelial cells.

In the following table, the results of tests concerning the reduction of edema caused by D-galactosamine, as a venous disease model, are given. These results are expressed in percent inhibition of the edema related to a non treated standard intoxicated in the same way as the treated animal. Dose is indicated in mg/kg and mode of administration is intraperitoneal (i.p.)

| substance | dose | % inhibition |
| --- | --- | --- |
| 8-benzyl-(+)-cyanidan-3-ol | 100 mg/kg | 61,7% |
| 8-n-propyl-3-O—benzyl-(+)-cyanidan-3-ol | 25 mg/kg | 56,1% |
|  | 100 mg/kg | 30,8% |
| 8-benzyl-3,5,7,3',4'-penta-O—benzyl-(+)-cyanidan-3-ol | 100 mg/kg | 52,2% |
| 8-(4-methylbenzyl)-(+)-cyanidan-3-ol | 15 mg/kg | 52% |
| 8-(2-methylbenzyl)-(+)-cyanidan-3-ol | 20 mg/kg | 46% |
| 6,8-di-(2-bromobenzyl)-(+)-cyanidan-3-ol | 30 mg/kg | 42% |
| 8-carboxy-3,5,7,3',4'-penta-O—benzyl-(+)-cyanidan-3-ol | 100 mg/kg | 40,8 |
| 6,8-di-(2-methylbenzyl)-(+)-cyanidan-3-ol | 50 mg/kg | 39% |
| 8-n-butyl-(+)-cyanidan-3-ol | 100 mg/kg | 37,8% |

(2)

"In-vitro" measurement of both the inhibition of the activity of lysosomal enzymes and the increase of the stability of lysosomal membranes at 0.05 to 2 mg per ml according to P. Niebes & Ponard (Biochem. Pharmacol. 24, 905 (1975).

(3) "In-vitro" measurement of the inhibition of other acute phase reactants, such as kinins, prostaglandins and thromboxanes.

Preferred pharmaceutical preparations contain compounds of the formula I wherein R' and R" are hydrogen, an unsubstituted or substituted aliphatic, cycloaliphatic, cycloaliphatic-aliphatic, aromatic or aromatic-aliphatic radical, halogen, formyl, free or functionally modified carboxyl, free or esterified or etherified hydroxyl or etherified mercapto, unsubstituted or substituted aliphatic acyl or primary, secondary or tertiary amine, but R' and R" cannot both be hydrogen simultaneously, and $R_1$, $R_2$, $R_3$, $R_4$ and $R_5$ are each hydrogen or an unsubstituted or substituted aliphatic, cycloaliphatic, cycloaliphatic-aliphatic or aromatic-aliphatic radical, and $R_2$ and $R_3$ together can also be a unsubstituted or substituted methylene group, and $R_1$ can also be an acyl group or an amidated carboxyl group, or therapeutically applicable salts of these compounds.

Particularly preferred pharmaceutical preparations contain compounds of the formula I wherein R' and R" are hydrogen, an unsubstituted or substituted alkyl, alkenyl or alkynyl radical, an unsubstituted or substituted cycloalkyl, or cycloalkenyl radical or a cycloalkyl- or cycloalkenyl-lower-alkyl or -lower-alkenyl radical, or an unsubstituted or substituted mono-, bi- or polycyclic aryl or aryl-lower-alkyl radical, halogen, formyl, free or or esterified carboxyl, amidated carboxyl, cyano, hydroxyl, unsubstituted or substituted lower-alkoxy, lower-alkenyloxy, lower-alkylthio, phenyltio, phenylalkylthio, lower-alkoxycarbonyloxy, lower-alkanoyloxy, formyloxy, benzoyloxy, alkanoyl, alkenoyl, unsubstituted or hydroxyl-substituted lower-alkylamino, di-lower-alkylamino, cycloalkylamino, N-cycloalkyl-N-lower-alkylamino, phenyl-lower-alkylamino, N-phenyl-lower-alkyl-N-lower-alkylamino, lower-alkyleneamino, phenylazo or phenylhydrazino, but R' and R" cannot both be hydrogen simultaneously; and $R_1$, $R_2$, $R_3$, $R_4$ and $R_5$ are each hydrogen, an unsubstituted or substituted alkyl, alkenyl or alkynyl radical, an unsubstituted or substituted cycloalkyl or cycloalkenyl radical, or a cycloalkyl or cycloalkenyl-lower-alkyl radical or lower-alkenyl radical, or an unsubstituted or substituted phenylalkyl radical, and $R_2$ and $R_3$ together can also be an unsubstituted or substituted methylene group, whilst $R_1$ can also be an acyl group or an amidated carboxyl group, and therapeutically applicable salts of these compounds.

More especially preferred pharmaceutical preparations contain compounds of the formula I wherein R' and R" are hydrogen, an alkyl radical which is unsubstituted or substituted by hydroxyl, oxo, amino, imino, di-lower-alkylamino, halogen, hydroxylimino, phenylimino, nitrophenylimino, acetylimino, cyano, carboxyl or lower-alkylsulfinyl, an alkenyl radical which is unsubstituted or substituted by carboxyl, lower-alkylcarbonyl, nitro, methylsulfinyl or acetoxymethylthio, or an alkynyl radical, a cycloalkyl or cycloalkyl-lower-alkyl or -lower-alkenyl radical, a phenyl or phenyl-lower-alkyl radical each unsubstituted or substituted by halogen, for example bromine or fluorine, or by lower alkyl, for example methyl, or by lower alkoxy, for example methoxy, or by a nitro group, or by a di-lower-alkylamino group, or they are halogen, formyl, carboxyl which is free of esterified by lower alkyl, for example methyl or ethyl, amidated carboxyl, in particular carbamoyl substituted by alkyl, di-lower-alkylamino or phenyl, cyano, hydroxyl, lower alkoxy which is unsubstituted or substituted by halogen, hydroxyl, mono- or di-lower-alkylamino or epoxy, or they are lower-alkenyloxy, lower-alkylthio, phenylalkoxy, phenylthio, phenylalkylthio, lower-alkoxy-carbonyloxy, lower-alkanoyloxy, formyloxy, benzoyloxy, alkanoyl, alkenoyl, benzoyl, unsubstituted or hydroxyl-substituted lower-alkylamino, di-lower-alkylamino, cycloalkylamino, N-cycloalkyl-N-lower-alkylamino, phenyl-lower-alkylamino, N-phenyl-lower-alkyl-N-lower-alkylamino, lower-alkyleneamino, phenylazo or phenylhydrazino, but R' and R'' cannot both be hydrogen simultaneously, and $R_1$, $R_2$, $R_3$, $R_4$ and $R_5$ are each hydrogen, lower alkyl, lower alkenyl, lower alkynyl, cycloalkyl, cycloalkenyl, cycloalkyl or cycloalkenyl-lower-alkyl or -lower-alkenyl radical or phenyl-alkyl radical, and $R_2$ and $R_3$ together can also be a methylene group substituted by phenyl radicals, whilst $R_1$ can also be an acyl group or an amidated carboxyl group; and therapeutically applicable salts of these compounds.

The specially preferred pharmaceutical preparations for the treatment of liver diseases contain compounds of the formula I wherein R' is hydrogen, halogen or lower-alkylbenzyl, and R'' is lower alkyl which is unsubstituted or substituted by hydroxyimino, lower alkenyl substituted by acetoxymethylthio, lower-alkylbenzyl, halogen, formyl, lower alkoxy or trifluoroacetyl, and $R_1$, $R_2$, $R_3$, $R_4$ and $R_5$ are each hydrogen, lower alkyl or phenyl-lower-alkyl, and $R_1$ can also be a higher acyl group; and therapeutically applicable salts of these compounds.

The most preferred pharmaceutical preparations for the treatment of liver diseases contain any one of the compounds: 8-(hydroxyiminomethyl)-(+)-cyanidan-3-ol, 6,8-dibromo-(+)-cyanidan-3-ol, 8-[2-(acetoxymethylthio)ethenyl]-3,5,7,3',4'-penta-O-benzyl-(+)-cyanidan-3-ol, 8-n-butyl-(+)-cyanidan-3-ol, 8-n-propyl-3-O-benzyl-(+)-cyanidan-3-ol, 6,8-di-(2-methylbenzyl)-(+)-cyanidan-3-ol, 8-tertiobutoxy-3,5,7,3',4'-penta-O-benzyl-(+)-cyanidan-3-ol, 8-trifluoroacetyl-3-O-benzyl-(+)-cyanidan-3-ol and, in particular, 8-formyl-3-O-palmitoyl-(+)-cyanidan-3-ol.

The specially preferred pharmaceutical preparations for the treatment of venous diseases contain compounds of the formula I wherein R' is hydrogen, lower-alkylbenzyl or halobenzyl, and R'' is lower alkyl, benzyl unsubstituted or substituted by lower alkyl or halogen, or it is carboxyl, and $R_1$, $R_2$, $R_3$, $R_4$ and $R_5$ are each hydrogen, lower alkyl or phenyl-lower-alkyl; and therapeutically applicable salts of these compounds.

The most preferred pharmaceutical preparations for the treatment of venous diseases contain any one of the compounds: 8-benzyl-(+)-cyanidan-3-ol, 8-n-propyl-3-O-benzyl-(+)-cyanidan-3-ol, 8-benzyl-3,5,7,3',4'-penta-O-benzyl-(+)-cyanidan-3-ol, 8-(4-methylbenzyl)-(+)-cyanidan-3-ol, 8-(2-methylbenzyl)-(+)-cyanidan-3-ol, 6,8-di-(2-bromobenzyl)-(+)-cyanidan-3-ol, 8-carboxyl-3,5,7,3',4'-penta-O-benzyl-(+)-cyanidan-3-ol, 6,8-di-(2-methylbenzyl)-(+)-cyanidan-3-ol and 8-n-butyl-(+)-cyanidan-3-ol.

The invention relates also to the use of these pharmaceutical preparations for combating conditions of disease of the aforementioned type.

The invention relates in addition to novel substituted (+)-3-cyanidanol derivatives of the general formula I wherein R' and R'' are an unsubstituted or substituted hydrocarbon radical, halogen, formyl, free or functionally modified carboxyl, free or etherified or esterified hydroxyl or mercapto, acyl or unsubstituted or substituted amino, but R' and R'' cannot both be hydrogen simultaneously, and $R_1$, $R_2$, $R_3$, $R_4$ and $R_5$ are each hydrogen or an unsubstituted or substituted hydrocarbon radical, and $R_2$ and $R_3$ together can also be a substituted or unsubstituted methylene group, whilst $R_1$ can also be an acyl group or an amidated carboxyl group, whereby however:

when $R_1$, $R_2$, $R_3$, $R_4$ and $R_5$ are hydrogen, R' cannot be hydrogen und simultaneously R'' benzyl, 2-hydroxybenzyl, 4-hydroxybenzyl or hydroxymethyl; R' cannot be hydrogen and simultaneously R'' 22-hydroxybenzyl or 4-hydroxybenzyl; and R' and R'' cannot both be hydroxymethyl;

when $R_2$, $R_3$, $R_4$ and $R_5$ are benzyl, R' cannot be hydrogen and simultaneously R'' benzyl and $R_1$ hydrogen, methyl or acetyl; or when $R_2$, $R_3$, $R_4$ and $R_5$ are methyl, one of the radicals R' and R'' cannot be 2-methoxybenzyl or 4-methoxybenzyl and the other hydrogen, and simultaneously $R_1$ hydrogen, R' and R'' cannot both be 2-methoxybenzyl, and simultaneously $R_1$ hydrogen; R' cannot be carboxyl or hydroxymethyl, and simultaneously R'' hydrogen and $R_1$ hydrogen or benzyl; R' cannot be methoxymethyl or acetoxymethyl, and simultaneously R'' hydrogen and $R_1$ acetyl; R' cannot be bromine, and simultaneously R'' hydrogen and $R_1$ hydrogen, benzyl or acetyl; R' and R'' cannot both be bromine, and simultaneously $R_1$ hydrogen, methyl, benzyl or acetyl; one of the radicals R' and R'' cannot be acetoxy or methoxycarbonyl and the other hydrogen, and simultaneously $R_1$ hydrogen, benzyl or acetyl; and one of the radicals R' and R'' cannot be hydroxyl and the other hydrogen, and simultaneously $R_1$ hydrogen or benzyl; or when $R_2$, $R_3$, $R_4$ and $R_5$ are methyl and R' hydrogen, R'' cannot be bromine, and simultaneously $R_1$ hydrogen, methyl, benzyl or acetyl; R'' cannot be benzyl, and simultaneously $R_1$ hydrogen, benzyl or methyl; R'' cannot be methoxy, and simultaneously $R_1$ methyl or acetyl; R'' cannot be methylthio, and simultaneously $R_1$ hydrogen or acetyl; and R'' cannot be α-hydroxybenzyl, and simultaneously $R_1$ benzyl;

and to therapeutically applicable salts of these compounds.

Preferred novel compounds are those of the formula I wherein R' and R'' are hydrogen, an unsubstituted or substituted aliphatic, cycloaliphatic, cycloaliphatic-aliphatic, aromatic or aromatic-aliphatic radial, halogen, formyl, free or functionally modified carboxyl, free or esterified or etherified hydroxyl or etherified mercapto, unsubstituted or substituted aliphatic acyl or primary, secondary or tertiary amine, and $R_1$, $R_2$, $R_3$, $R_4$ and $R_5$ are each hydrogen or an unsubstituted or substituted aliphatic, cycloaliphatic, cycloaliphatic-aliphatic or aromatic-aliphatic radical, and $R_2$ and $R_3$ together can also be an unsubstituted or substituted methylene group, whist $R_1$ can also be an acyl group or an amidated carboxyl group, with the exception of the compounds excluded above; and therapeutically applicable salts of these compounds.

Particularly preferred novel compounds of the formula I are those wherein R' and R'' are hydrogen, an unsubstituted or substituted alkyl, alkenyl or alkynyl radical, an unsubstituted or substituted cycloalkyl or cycloalkenyl radical or a cycloalkyl- or cycloalkenyl-lower-alkyl or -lower-alkenyl radical, or an unsubstituted or substituted mono-, bi- or polycyclic aryl or aryl-loweralkyl radical, halogen, formyl, free of esterified carboxyl, amidated carboxyl, cyano, hydroxyl, unsubstituted or substituted lower alkoxy, lower alkenyloxy, lower alkylthio, phenylthio, phenylalkylthio, lower alkoxycarbonyloxy, lower alkanoyloxy, formyloxy benzyloxy, alkanoyl, alkenoyl, unsubstituted or hydroxyl-substituted lower alkylamino, di-lower-alkylamino, cycloalkylamino, N-cycloalkyl-N-lower-alkylamino, phenyl-lower-alkylamino, N-phenyl-lower-alkyl-N-lower-alkylamino, lower-alkyleneamino, phenylazo or phenylhydrazino, and $R_1$, $R_2$, $R_3$, $R_4$ and $R_5$ are each hydrogen, an unsubstituted or substituted alkyl, alkenyl or alkynyl radical, an unsubstituted or substituted cycloalkyl or cycloalkenyl radical or a cycloalkyl- or cycloalkenyl-lower-alkyl or -loweralkenyl radical, or an unsubstituted or substituted phenyl-alkyl radical, and $R_2$ and $R_3$ together can also be an unsubstituted or a substituted methylene group, and $R_1$ can also be an acyl group or an amidated carboxyl group, with the exception of the compounds excluded above; and therapeutically applicable salts of these compounds.

More especially preferred novel compounds are those of the formula I wherein R' and R" are hydrogen, an alkyl radical which is unsubstituted or substituted by hydroxyl, oxo, amino, imino, di-lower-alkylamino, halogen, hydroxyimino, phenylimino, nitrophenylimino, acetylimino, cyano, carboxyl or lower-alkylsulfinyl, an alkenyl radical which is unsubstituted or substituted by carboxyl, lower-alkylcarboxy, nitro, methylsulfinyl or acetoxymethylthio, or they are an alkynyl radical, a cycloalkyl or cycloalkyl-lower-alkyl or -lower-alkenyl radical, a phenyl or phenyl-lower-alkyl radical each unsubstituted or substituted by halogen, for example bromine or fluorine, or by lower alkyl, for example methyl, or by lower alkoxy, for example methoxy, or by a nitro group or by a di-lower-alkylamino group, or they are halogen, formyl, carboxyl which is free or esterified by lower alkyl, for example methyl or ethyl, amidated carboxyl, in particular carbamoyl substituted by alkyl, di-lower-alkylamino or phenyl, cyano, hydroxyl, lower alkoxy which is unsubstituted or substituted by halogen, hydroxyl, mono- or di-lower-alkylamino or epoxy, or they are lower-alkenyloxy, lower-alkylthio, phenylthio, phenyl-lower-alkylthio, lower-alkoxycarbonyloxy, lower-alkanoyloxy, formyloxy, benzyloxy, alkanoyl, alkenoyl, unsubstituted or hydroxyl-substituted lower-alkylamino, di-lower-alkylamino, cycloalkylamino, N-cycloalkyl-N-lower-alkylamino, phenyl-lower-alkylamino, N-phenyl-lower-alkyl-N-lower-alkylamino, lower-alkyleneamino, phenylazo or phenyl-hydrazino, and $R_1$, $R_2$, $R_3$, $R_4$ and $R_5$ are each hydrogen, lower-alkyl, lower-alkenyl, lower alkynyl, cycloalkyl, cycloalkenyl, cycloalkyl- or cycloalkenyl-lower-alkyl or -lower-alkenyl or phenyl-lower-alkyl, and $R_2$ and $R_3$ together can also be an unsubstituted or substituted methylene group, whilst $R_1$ can also be an acyl group or an amidated carboxyl group, whereby however:

when $R_1$, $R_2$, $R_3$, $R_4$ and $R_5$ are hydrogen, R' cannot be hydrogen, and simultaneously R" benzyl or hydroxymetyl; and R' and R" cannot both be hydroxymethyl;

when $R_2$, $R_3$, $R_4$ and $R_5$ are benzyl, R' cannot be hydrogen, and simultaneously R" benzyl and $R_1$ hydrogen, methyl or acetyl; or when $R_2$, $R_3$, $R_4$ and $R_5$ are methyl, one of the radicals R' and R" cannot be 2-methoxybenzyl or 4-methoxybenzyl and the other hydrogen, and simultaneously $R_1$ hydrogen; R' and R" cannot both be 2-methoxybenzyl, and simultaneously $R_1$ hydrogen; R' cannot be carboxyl or hydroxymethyl, and simultaneously R" hydrogen and $R_1$ hydrogen or benzyl; R' cannot be bromine, and simultaneously R" hydrogen and $R_1$ hydrogen, benzyl or acetyl; R' and R" cannot both be bromine, and simultaneously $R_1$ hydrogen, methyl, benzyl or acetyl; one of the radicals R' and R" cannot be acetoxy or methoxycarbonyl and the other hydrogen, and simultaneously $R_1$ hydrogen, benzyl or acetyl; and one of the radicals R' and R" cannot be hydroxyl and the other hydrogen, and simultaneously $R_1$ hydrogen or benzyl; or when $R_2$, $R_3$, $R_4$ and $R_5$ are methyl and R' is hydrogen, R" cannot be bromine, and simultaneously $R_1$ hydrogen, methyl, benzyl or acetyl; R" cannot be benzyl, and simultaneously $R_1$ hydrogen, benzy or acetyl; R" cannot be methoxy, and simultaneously $R_1$ methyl or acetyl; and R" cannot be methylthio, and simultaneously $R_1$ hydrogen or acetyl, and therapeutically applicable salts of these compounds.

The specially preferred novel compounds are those of the formula I wherein R' is hydrogen, halogen, lower-alkylbenzyl or halobenzyl, and R" is lower alkyl hydroxyimino-lower-alkyl or acetoxy-lower-alkenyl, or it is benzyl, halogen formyl, lower alkoxy or trifluoroacetyl each unsubstituted or substituted by lower alkyl or halogen, or it is carboxyl, and $R_1$, $R_2$, $R_3$, $R_4$ and $R_5$ are each hydrogen, lower alkyl or phenyl-lower-alkyl, and $R_1$ can also be a higher alkanoyl group, whereby however:

when $R_1$, $R_2$, $R_3$, $R_4$, $R_5$ and R' are hydrogen, R" cannot be benzyl; or when $R_2$, $R_3$, $R_4$ and $R_5$ are benzyl, R' cannot be hydrogen, and simultaneously R" benzyl and $R_1$ hydrogen or methyl; or when $R_2$, $R_3$, $R_4$ and $R_5$ are methyl, R' cannot be bromine, and simultaneously R" hydrogen and $R_1$ hydrogen or benzyl, and R' and R" cannot both be bromine, and simultaneously $R_1$ hydrogen, methyl or benzyl; or when $R_2$, $R_3$, $R_4$ and $R_5$ are methyl and R' is hydrogen, R" cannot be bromine, and simultaneously $R_1$ hydrogen, methyl or benzyl, and R" cannot be benzyl, and simultaneously $R_1$ hydrogen or benzyl, and R" cannot be methoxy, and simultaneously $R_1$ methyl or acetyl;

The most preferred compounds are the following: 8-(hydroxyiminomethyl)-(+)-cyanidan-3-ol, 8-[2-(acetoxymethylthio)ethenyl]-2,5,7,3',4'-penta-O-benzyl-(+)-cyanidan-3-ol, 8-n-butyl-(+)-cyanidan-3-ol, 8-n-propyl-3-O-benzyl-(+)-cyanidan-3-ol, 6,8-di-(2-methylbenzyl)-(+)-cyanidan-3-ol, 8-tertiobutoxy-3,5,7,3',4'-penta-O-benzyl-(+)-cyanidan-3-ol, 8-trifluoroacetyl-3-O-benzyl-(+)-cyanidan-3-ol, and particularly 8-formyl-3-O-palmitoyl-(+)-cyanidan-3-ol, 8-n-propyl-3-O-benzyl-(+)-cyanidan-3-ol, 8-benzyl-3,5,7,3',4'-penta-O-benzyl-(+)-cyanidan-3-ol, 8-(4-methylbenzyl)-(+)-cyanidan-3-ol, 8-(2-methylbenzyl-(+)-cyanidan-3-ol, 6,8-di-(2-bromobenzyl)-(+)-cyanidan-3-ol, 8-n-butyl-(+)-cyanidan-3-ol and 8-carboxy-3,5,7,3',4'-penta-O-benzyl-(+)-cyanidan-3-ol, and therapeutically applicable salts of these compounds.

Compounds of the general formula I can be produced by processes known per se. Thus, the novel compounds of the general formula I as defined above with the exception of the compounds excluded above, and therapeutically applicable salts of these compounds, can be produced by replacing, in the 8- and/or 6-position of a compound of the formula II

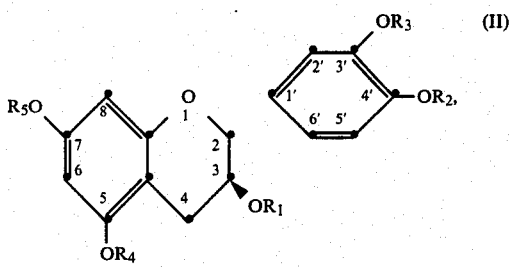

in which R₁, R₂, R₃, R₄ and R₅ have the meanings defined in the formula I, one or two hydrogen atoms by a substituent R' and/or R", and, if desired, converting a resulting compound of this general formula I into another compound of this formula I according to the invention, and/or, if desired, converting a free compound obtained into a salt, or a salt into the free compound or into another salt.

One or two hydrogen atoms in the 8- and/or 6-position of the compounds of the formula II can be replaced in a manner known per se, for example by halogen, unsubstituted or substituted hydrocarbon radicals, formyl or acyl. The replacement of hydrogen in the 8- and/or 6-position can be effected for example by elementary halogen, for example bromine, in an inert solvent according to 'Methoden der organischen Chemie' given in Houben-Weyl (fourth Edition), Vol. 5/4, pp. 233–249; or by chlorine in an analogous manner according to the processes described in Houben-Weyl (fourth Edition), Vol. 5/3, pp. 651–673. Further halogenating agents which can be used for example for the replacement of hydrogen by bromine are: hypobromous acid, acylhypobromites and organic bromine comounds, for example N-bromosuccinimide, N-bromoacetamide, N-bromophthalimide, pyridinium perbromide, dioxane dibromide, 1,3-dibromo-5,5-dimethyl-hydantoin and 2,4,4,6-tetrabromo-2,5-cyclohexadien-1-one, whereby one or two bromine atoms can be introduced.

The exchange of hydrogen in the 8- and/or 6-position can be performed for example also in trifluoroacetic acid with titanium tetrachloride according to Tetrahedron Letters (1970), p. 2211, or with trichlorocyanuric acid in an inert solvent according to Journ. Org. Chem. Vol. 35, p. 719, (1970).

The replacement of hydrogen in the 8- and/or 6-position by iodine can be effected for example by elementary iodine in the presence of mercury oxide or nitric acid. Instead of using elementary iodine, it is possible to use for example also potassium iodide in the presence of a thallium salt, for example thallium (III)-trifluoroacetate, according to Tetrahedron Letters (1969), p. 2427.

Unsubstituted or substituted hydrocarbon radicals, particularly unsubstituted or substituted alkyl and also aryl-lower-alkyl radicals, such as unsubstituted or substituted benzyl radicals, can be introduced in the 8- and/or 6-position by heating compounds of the formula II with alkyl- or aryl-lower-alkyl-halides, in which process one or two hydrogen atoms can be replaced by an unsubstituted or substituted hydrocarbon radical. The reactions of compounds of the formula II with alkyl halides or aryl-lower-alkyl halides can also be performed in the presence of catalytic amounts of a Lewis acid, for example of anhydrous aluminium chloride according to Friedel-Crafts, Org. Reaction 3, 1 ff. (1946). In place of aluminium chloride, it is also possible to use, according to Org. Reactions 3, 1 ff. (1946), iron (III)-chloride or zinc(II)-chloride. Instead of alkylhalides, alcohols can be used together with boron trifluoride-etherate.

The exchange of hydrogen in the 8- and/or 6-position by a formyl group can be performed for example according to Vilsmeier by means of N-substituted formamides, for example N,N-dimethylformamide, in the presence of phosphorus oxychloride according to Houben-Weyl, 4th Edition, Vol. 7/2, pp. 29–36 and Ber., 60 (1927) p. 121. Most suitable as formylating agent is formyl-monomethyl-aniline because of the increased reactivity of its complex with phosphorus oxychloride. As further modifications, suitable formylating agents are formamide, formylpiperidine and dimethylformamide. The phosphorus oxychloride used here can be successfully replaced in some cases by phosgene. It is moreover possible to convert a compound of the formula II in which R₁ to R₅ are hydrocarbon radicals into a corresponding 8- and/or 6-metal compound, for example by means of phenyllithium in ether firstly into a corresponding lithium compound, and to then react this with an N,N-disubstituted formamide, for example N-methylformanilide to give a compound of the formula I (cp. Org. React. 8, 258 (1954)).

A further process variant suitable for introducing the formyl group in the 8- and/or 6-position is the method of L. Gattermann (according to Houben-Weyl, 4th Edition, Vol. 7/2, pp. 20–27), where formylation can be effected by use of a mixture of hydrogen cyanide, hydrogen chloride and aluminium chloride, the reaction product firstly obtained being then converted by hydrolysis, for example by a dilute mineral acid, for example dilute hydrochloric acid, into the desired formyl compound. For compounds in which R₄ and/or R₅ are hydrogen, a suitable Friedel-Crafts catalyst, in place of aluminium chloride, is zinc(II)-chloride. Reactions of this type are advantageously performed at a temperature of 40°–90° C. A generally applicable variant of the above reaction is the reaction with zinc(II)-cyanide and hydrogen chloride, in the absence or presence of aluminium chloride (cp. J. Am. Chem. Soc. 64, 30 (1942)).

A suitable method for the introduction of the formyl groups in the 8- and/or 6-position of the compounds of the formula II in which R₄ and/or R₅ are hydrogen is that of K. Reimer and F. Tiemann, which method comprises the reaction of such compounds of the formula II with chloroform and sodium hydroxide solution (cp. Houben-Weyl, 4th Edition, Vol. 7/2, pp. 36–38).

A further process variant for the introduction of the formyl group consists of the condensation of a compound of the formula II with formaldehyde, in the presence of an oxidising agent, according to Houben-Weyl, 4th Edition, Vol. 7/2, pp. 38–43. The oxidising agent employed can be for example phenylhydroxylaminosulfonic acid or p-nitrosodimethylaniline. The Schiff bases firstly obtained are cleaved hydrolytically, for example with sodium hydroxide solution.

Compounds of the formula I in which there is an acyl group in the 8- and/or 6-position can be produced for example using the Friedel-Craft method (cp. G. A. Olah, Friedel-Crafts and Related Reactions, Vol. I, Interscience, New York, 1963–1965), by reaction of a compound of the formula II with a reactive functional derivative, especially a halide or an anhydride, of an aliphatic, cycloaliphatic, cycloaliphatic-aliphatic, aromatic or aromatic-aliphatic carboxylic acid in the presence of a Lewis acid, for example aluminium chloride, antimony(III)-chloride or antimony(V)-chloride, iron-(III)-chloride, zinc(II)-chloride or boron trifluoride.

A further process variant for the introduction of an acyl group in the 8- and/or 6-position is the method developed by K. Hoesch and J. Houben (cp. P. E. Spoerri and A. S. du Bois, The Hoesch Synthesis, Org. Reactions 5, 387 ff. (1949) and B., 48, 1122 (1915)), which comprises the reaction of a compound of the formula II with a nitrile in the presence of a Lewis acid, for example aluminium chloride or zinc(II)-chloride, and hydrogen chloride in an inert solvent. The intermediately formed ketimine hydrochlorides are hydrolysed by the addition of water to the desired acyl compounds.

Compounds of the formula I obtained can be converted into other compounds of the formula I in a manner known per se.

For example, compounds of the formula I in which R′ and/or R″ are cyano can be obtained from corresponding compounds in which R′ and/or R″ are halogen by reaction with copper(I)-cyanide in pyridine according to Org. Synth. (1955) Col. Vol. 3, 631, 212; J. Am. Chem. Soc. (1966) 88, 3318; J. Org. Chem. (1952) 17, 298; preferably at a temperature of 25°–225° C. It is possible to perform in an analogous manner the reaction with copper(I)-cyanide also in dimethylformamide in the presence of iron(III)-chloride and hydrogen chloride according to J. Org. Chem. (1961) 26, 2522. Other polar solvents can also be used, such as 1-methyl-2-pyrrolidone according to J. Org. Chem. (1961) 26, 2525; 2-hexamethyl-phosphoric acid-triamide according to J. Org. Chem. (1969) 34; 3626; or dimethylsulfoxide according to Proc. Chem. Soc. (1962) 113.

Compounds of the general formula I in which R′ and/or R″ is halogen can be converted into compounds of the formula I wherein R′ and/or R″ are formyl by converting the halogen compound of the formula I into an organometallic compound, especially into an organomagnesium, organozinc or organolithium compound, and converting this, by reaction with a derivative of formic acid, for example formic acid ester, especially orthoformic acid ester, N,N-disubstituted formamides, particularly N-substituted formanilides or N-arylformimido ester, and decomposition of the immediate reaction products (cp. Houben-Weyl. 4th Edition, Vol. 7/1, pp. 64–70; Org. Synth. (1955) Col. Vol. 3, 701; (1943) Col. Vol. 2, 323 and Ber. (1970) 103, 643; Annalen (1912) 393, 215; Chimia (1964) 18, 141; J. Chem. Soc. (1956) 4691; J. Org. Chem. (1970) 35, 711; J. Org. Chem. (1941) 6, 489), into the corresponding compound of the general formula I with formyl in the 8- and/or 6-position.

Furthermore, compounds of the formula I in which R′ and/or R″ are halogen can be converted into compounds of the formula I wherein R′ and/or R″ are an acyl radical by converting the halogen compound of the formula I into an organometal compound, particularly into an organomagnesium, organocadmium, organozinc or organolithium compound, and reacting this with a reactive functional derivative, especially with a halide, anhydride, ester or nitrile, of an aliphatic, cycloaliphatic, cycloaliphaticaliphatic, aromatic or aromatic-aliphatic carboxylic acid, and decomposing the immediate product obtained to the corresponding compound of the formula I in which R′ and/or R″ are an acyl group (cp. Houben-Weyl, 4th Edition, Vol. 7/2a, pp. 558–597; and Org. React. 8, 28).

Compounds of the formula I in which R′ and/or R″ are halogen can be converted into compounds of the formula I wherein R′ and/or R″ are a free or functionally modified carboxyl, especially into an ester or a monosubstituted amide, by converting the halogen compound of the formula I into an organometal compound, particularly into an organomagnesium, organocadmium, organozinc or organolithium compound, and reacting this with a reactive derivative of carbonic acid, especially carbon dioxide, a carbonic ester halide or an isocyanate, or with carbon monoxide (cp. J. Org. Chem. (1959), 24, 504; J. Am. Chem. Soc. (1939) 61, 1371; and Bull. Chem. Soc. Jap. (1967) 40, 2203).

Compounds of the general formula I in which R′ and/or R″ are halogen can be converted into compounds of the formula I wherein R′ and/or R″ are an unsubstituted or substituted hydrocarbon radical, particularly an unsubstituted alkyl, aryl-lower-alkyl or aryl radical, by reacting a compound of the formula I in which R′ and/or R″ are halogen with an organometallic compound of the radical R′ and/or R″ to be introduced. For example, organoalkali metal or organoalkaline-earth metal compounds, for example organolithium and organosodium compounds or organomagnesium compounds, can be reacted by the processes described in Houben-Weyl (4th Edition) Vol. 7/2a, pp. 486–502 (cp. J. Am. Chem. Soc., (1968), 90, 2423; Tetrahedron Letters (1970) 26, 4041; J. Am. Chem. Soc. (1929), 51, 1483, J. Am. Chem. Soc. (1938) 60, 2598). According to the stated references, it is also possible in each case for two halogen compounds, corresponding to the radicals to be reacted, to be reacted in the presence of an alkali metal or alkaline-earth metal, or in the presence of a compound releasing one of these, for examples butyl lithium, where the reaction proceeds by way of an organometallic compound as intermediate stage. The organometallic compounds used can however also be for example organoaluminium, organocopper-lithium or organomanganese-lithium compounds (cp. J. Org. Chem. (1970), 35, 532; J. Am. Chem. Soc. (1968), 90, 5615; and Tetrahedron Letters, (1970), 315).

Compounds of the general formula I in which R′ and/or R″ are halogen can also be converted into compounds of the formula I wherein R′ and/or R″ are a hydroxyl group by hydrolysing a compound in which R′ and/or R″ are halogen with a strong base, for example sodium or potassium hydroxide solution, preferably in the presence of a catalyst, for example copper(II)-sulfate (cp. Can. J. Chem. (1962), 40, 2175; or J. Org. Chem. (1939), 4, 318). A conversion of a mono- or dihalogen compound of the formula I into a corresponding hydroxyl compound can also be performed by converting the mono- or dihalogen compound into a corresponding metal compound, for example into an alkali metal compound, such as a lithium compound, or alkaline-earth metal compound, such as a magnesium compound, or a heavy metal compound, for example a mercury halide compound, and hydrolysing this metal compound under oxidising conditions (cp. J. Org. Chem. (1957) 22, 1001; J. Am. Chem. Soc. (1959) 81, 4230; Org. Synth. (1963) 43, 55; and Tetetrahydron Letters (1970), 2679). The oxidising agent used can be for example hydrogen peroxide, t-butylhydroperoxide as well as the lithium salt thereof, and also the perbenzoic ester thereof, and also oxygen or ozone.

In addition, compounds of the general formula I in which R′ and/or R″ is halogen can be converted into compounds of the general formula I in which R' and/or R" is an etherified hydroxyl group by reacting a mono- or dihalogen compound of the formula I with a magnesium halide, especially with a magnesium bromide compound, and reacting the resulting magnesium organic compound with a perbenzoic ester, for example with a tertiary butyl ester (cp. J. Am. Chem. Soc. (1959), 81, 4230; and Org. Synth. (1963) 43, 55).

Compounds of the general formula I in which R' and/or R" are halogen can also be converted into compounds of the formula I in which R' and/or R" is an esterified hydroxyl group by reacting a mono- or dihalogen compound of the formula I with a metal salt of a carboxylic acid, especially a heavy metal salt, for example a silver or copper salt, or with an alkali metal salt, for example a sodium or potassium salt, of a carboxylic acid (cp J. Am. Chem. Soc. (1951), 73, 5487; ibidem (1949), 71, 3214; and ibidem (1966), 88, 4521).

Compounds of the general formula I in which R' and/or R" are formyl can be converted into compounds of the formula I in which R' and/or R" are a [2,2-di-(lower-alkoxycarbonyl)-vinyl]group, where a lower-alkoxycarbonyl group in the substituent can be in each case also replaced by cyano or amido, by reacting a compound of the formula I in which R' and/or R" are formyl with a malonic acid derivative, for example malonic acid diethyl ester, cyanoacetic acid and esters and amides thereof, malonic acid, malonnitrile, malonamide or malonmonoamide ester, in the presence of a slightly basic catalyst, such as ammonia, secondary and tertiary amines, for example di- or triethylamine, piperidine and pyridine (cp. G. Jones, Org. Reactions 15, 204 ff. (1967); E. Knoevenagel, Ber. dtsch. chem. Ges. 29 (1896) 121; 31 (1898) 2598; 37 (1904) 4461; Doebner, Ber. dtsch. chem. Ges. 33 (1900) 2140; (1902) 1137).

It is possible to use as starting materials for the reaction, in place of the malonic acid derivatives listed above, also other compounds having an activated methylene group, for example acetoacetic acid esters and β-diketones, and also analogs in which one or both carbonyls are replaced by sulfo groups, as well as nitroalkanes.

Resulting compounds of the formula I in which R' and/or R" are a [2,2-di-(lower-alkoxycarbonyl)-vinyl] group can be converted into compounds of the formula I wherein R' and/or R" are carboxyethenyl by decarboxylation. The decarboxylation can be performed by pyrolysis or by hydrolysis, for example in an alkaline or acid medium.

Compounds of the general formula I in which R' and/or R" are a formyl group can also be converted into compounds of the formula I wherein R' and/or R" are an unsubstituted or substituted carboxyethenyl group by reacting a compound of the formula I in which R' and/or R" is a formyl group with acetic anhydride or with the anhydride of a substituted acetic acid in the presence of a basic condensing agent, especially sodium acetate (cp. J. R. Johnson, Organic Reactions 1, 210 (1942); H. O. House, Modern Synthetic Reactions 2nd ed. (W. A. Benjamin, California, 1972) pp. 660-663; P. H. Leake, Chem. Reviews 56 (1956) 27).

Mono- and/or diformyl compounds of the general formula I can be converted into compounds of the formula I wherein R' and/or R" are a 1-hydroxycyanomethyl radical or an unsubstituted or substituted 1-aminomethyl cyanide by reacting a mono- and/or diformyl compound of the general formula I with a reagent releasing hydrogen cyanide, for example with an alkali cyanide, especially potassium cyanide, in the presence of acetic acid, or with anhydrous hydrogen cyanide in the presence of an alkaline catalyst, for example a potassium hydroxide solution (cp. H. H. Hustedt and E. Pfeil, Liebigs Ann. Chem. 640 (1961) 15; A. J. Ulte, Receuil Trav. chim. Pays-Bas 28 (1909) 1, 248, 257; Ber. dtsch. chem. Ges. 39 (1906) 1856), or with hydrogen cyanide, or with a reagent releasing this, in the presence of ammonia or a primary or secondary amine (cp. A. Strecker, Liebigs Ann. Chem. 75 (1850) 27, 91 (1854) 349; or Migrdichian, The Chemistry of Organic Cyanogen Compounds (New York 1947) 198).

According to a further process variant, mono- or diformyl compounds of the general formula I can be converted into corresponding compounds having 1-hydroxy-2-methylsulfinyl-ethyl and/or 2-methylsulfinyl-ethenyl as R' and/or R" by reacting a formyl compound of the formula I with dimethyl sulfoxide in the presence of s strong base, for example an alkali hydroxide, such as sodium hydroxide, or with the reaction product of dimethyl sulfoxide and the strong base (cp. dimethyl sulfoxide, Diether Martin et al, Akademie Verlag (1971) 344-366).

Mono- or diformyl compounds of the general formula I can be converted into compounds of the formula I wherein R' and/or R" are an unsubstituted or substituted 2-lower-alkoxycarbonylethenyl by reacting a mono- or diformyl compound of the general formula I with an unsubstituted or substituted acetic acid lower alkyl ester in the presence of an alkaline condensing agent, for example metallic sodium or sodium hydroxide (cp. Houben-Weyl-Müller 8, (1952) 514, 4 II (1955) 25; Org. Reactions, Vol. 16, 1; H. O. House, Modern Synthetic Reactions (W. A. Benjamin California, 2nd ed. 1972) pp. 632-639; and J. A. Fine, Ph. Pulaski, J. Org. Chem. 38, 1747 (1973)).

Compounds of the general formula I in which R' and/or R" are a formyl group can be converted, in a manner known per se, into compounds of the formula I in which R' and/or R" are a free or functionally modified formyl group, for example acetal, oxime, semicarbazone, thiosemicarbazone, hydrazone, oxime ether or unsubstituted or substituted imine, for example the radical of a Schiff base (cp. Chemiker Zeitung "Addition an die Carbonyl group" 80, 379 (1956); Weygand, Hilgetag, Org. Chem. Experimentierkunst, Leipzig 1970, 4th Edition, 391-396 and 517-528).

Compounds of the general formula I in which R' and/or R" are formyl or acyl can be converted into compounds of the formula I in which R' and/or R" are an esterified hydroxyl group by reacting a compound of the formula I in which R' and/or R" are formyl or acyl with a peroxide, for example with an organic or inorganic peroxy acid, for example peroxymonosulfuric acid (Caro's acid), peroxybenzoic acid, peroxyacetic acid, monoperoxyphthalic acid and trifluoroperoxyacetic acid (cp. C. H. Hassall, Organic Reactions 9, 73 (1957); P. A. S. Smith, in P. de Mayo, Ed., Molecular Rearrangements, vol. 1 (Wiley-Interscience, New York, 1963), pp. 568-591; Ch. Bischoff, Z. Chem. 13, 11 (1973); A. DeBoer, R. E. Ellwanger, J. Org. Chem. 39, 77 (1974); H. O. House, Modern Synthetic reactions (W. A. Benjamin, Inc., London, 2nd ed., 1972), pp. 323-327; S. A. Monti, Ch. K. Ward, Tetrahedron Letters 1971, 697; Y. Ogata, Y. Sawaki, J. Am. Chem. Soc. 94, 4189 (1972); M. Winnik, V. Stoute, Can. J. Chem. 51, 2788 (1973); J. Am. Chem. Soc. 96, 1977 (1974); D.

H. Aue, D. Thomas, J. Org. Chem. 39, 3855 (1974); and Y. Ogata et al., ibid. 39, 216 (1974)).

Compounds of the general formula I in which R' and/or R" are a formyl group can also be converted into compounds of the general formula I wherein R' and/or R" are an unsaturated radical at the linkage point, for example an unsubstituted or substituted ethenyl compound, by reacting a corresponding compound of the formula I wherein R' and/or R" are formyl or acyl with a triphenylphosphinemethylene group which is unsubstituted or substituted in the methylene group, or with a reagent releasing this triphenylphosphinemethylene, for example triphenylphosphinemethyl bromide, in the presence of phenyl lithium (cp. G. Wittig and U. Schöllkopf, Ber. 87, 1318 (1954); G. Wittig and W. Haag, ibid 88, 1654 (1955).

Compounds of the general formula I in which R' and/or R" are formyl or acyl can be converted into compounds of the formula I wherein R' and/or R" are an unsubstituted or substituted 2-lower-alkoxycarbonyl-1-hydroxyethyl group or 2-lower-alkoxycarbonylvinyl by reacting a compound of the general formula I in which R' and/or R" are formyl or acyl with an unsubstituted or substituted haloacetic acid ester, particularly bromoacetic acid-lower-alkyl ester, in the presence of metallic zinc in an inert solvent, for example ether, benzene, toluene or tetrahydrofuran, and hydrolysing the organic zinc compound obtained to give a β-hydroxycarboxylic acid ester, and then optionally dehydrating this to the unsaturated compound in which R' and/or R" are an unsubstituted or substituted 2-lower-alkoxycarbonylvinyl radical. The reaction can be catalysed by small additions of elementary iodine. Metallic lithium can also be used, in place of metallic zinc, for producing an organolithium compound (cp. R. L. Shriner, Organic Reactions 1, 1 (1942); D. G. M. Diaper, A. Kuksis, Chem. Revs. 59, 89 (1959); H. O. House, Modern Synthetic Reactions 2nd ed. (W. A. Benjamin, California, 1972), pp. 671–682; M. Gaudemar, Organometal. Chem. Rev. Sect. A 8, 183 (1972); M. W. Rathke, Organic Reactions 22, 423 (1975); A. Balsamo et al., Tetrahedron Letters 1974, 1005; J. F. Ruppert, J. D. White, J. Org. Chem. 39, 269 (1974); J. E. Baldwin, J. A. Walker, Chem. Commun. 1973, 117; A. P. Krapcho et al., J. Org. Chem. 39, 1322, 1650 (1974); Tetrahedron Letters 1974, 2721).

Compounds of the formula I in which R' and/or R" are unsubstituted or substituted α-hydroxy hydrocarbon radicals can be obtained by reducing a mono- or diformyl compound or diacyl compound of the general formula I. The reduction can be effected in a manner known per se, for example by catalytically activated or nascent hydrogen. The reduction can also be performed with the aid of metal hydrides, for example aluminium hydride or boron hydride and diborane, especially however with complex metal hydrides, such as lithium aluminium hydride, sodium boron hydride, lithium tritertbutoxyaluminium hydride. Reduction of the compounds of the formula I in which R' and/or R" are formyl or acyl can be performed according to Meerwein-Ponndorf-Verly with use of a secondary alcohol, for example isopropanol, in the presence of aluminium-triisopropylate. As solvents can be used aromatic hydrocarbons, such as benzene or toluene (cp. Houben-Weyl, Methodes der Org. Chemie, 4th Edition, 7/1, 1086 (1954), C. H. Snyder, M Micklus, J. Org. Chem. 35, 264 (1970)).

Mono- and/or dialkanoyl compounds, especially mono- or diacetyl compounds, of the formula I can be converted by reaction with ammonium polysulfide, or by reaction in the presence of sulfur and primary or secondary amines, for example morpholine, into compounds of the formula I in which R' and/or R" are a carbamoyl-lower-alkyl group, especially carbamoyl-methyl or an N-substituted thiocarbamoyl-lower-alkyl group, for example morpholinothiocarbamoyl-methyl (cp. C.Willgerodt, Ber. 20 2467 (1887); 21, 534 (1888); K. Kindler, Ann. 431, 193 (1923); M. Carmock, M. A. Spielman, Organic Reactions 3, 83 (1946); and F. Asinger et al., Augew. Chem. Int. Ed. 3, 19 (1964)).

Compounds of the formula I in which R' and/or R" are an unsubstituted or substituted N-mono- or disubstituted α-aminomethylacyl group or an α-methyleneacyl group can be obtained by reacting according to Mannich a compound of the general formula I in which R' and/or R" are acyl radicals, which contain in the α-position with respect to the carbonyl group at least one hydrogen atom, with formaldehyde and ammonia or with a primary or secondary amine, and optionally removing ammonia or the employed primary or secondary amine from the aminomethyl compound firstly obtained (cp. C. Mannich, W. Krosche, Arch. Pharm. 250, 647 (1912); F. F. Blicke, Org. Reactions 1, 303 (1942); H. Hellmann, G. Opitz, Angew. Chem. 68, 265 (1956); S. A. Monti, G. D. Costillo, J. Org. Chem. 35, 3764 (1970)).

Compounds of the formula I in which R' and/or R" are a lower aliphatic radical substituted by lower alkyl-sulfinyl, for example lower alkyl or lower alkenyl, especially vinyl, can be converted into compounds of the formula I wherein R' and/or R" is an α-acyloxy-lower-alkylthio-lower-alkyl radical or -lower-alkenyl radical, for example the acetoxymethylthio-vinyl radical, by rearranging the above-mentioned starting compounds of the formula I with an anhydride, for example acetic anhydride, in the presence of a base, such as sodium acetate or potassium tertiary butylate (cp. Theilheimer 15 (1961) No. 177; Theilheimer 19 (1965) No. 827; L. Horner, P. Kaiser, Ann. 626, 19 (1959); H. D. Becker, G. J. Mikol, G. A. Russel, J. Am. Chem. Soc. 85, 3410 (1963); C. R. Johnson, W. G. Phillips, J. Am. Chem. Soc. 91 682 (1969); T. Jagiara et al., TetraHydron 28, 2765 (1972)).

Mono- or diformyl compounds of the formula I can be converted into compounds of the formula I in which R' and/or R" are unsubstituted or mono- or disubstituted carbamoyl or lower alkoxycarbonyl by reacting one of the stated starting materials, in the presence of an alkali metal cyanide and a selective oxidising agent, particularly manganese dioxide, with ammonia or with a primary or secondary amine or a lower alkanol (cp. U.S. Pat. No. 3,948,931).

Compounds of the formula I in which R' and/or R" are formyl can be converted into compounds of the formula I wherein R' and/or R" are a 1-hydroxy-2-nitro-lower-alkyl radical or a 2-nitro-1-lower-alkenyl radical by reacting a corresponding compound of the formula I with a nitro-lower-alkane in the presence of an organic or inorganic base, for example pyridine or piperidine, a basic ion-exchanger resin, such as Amberlite ® IRA 400, or sodium hydroxide, and optionally hydrogenating the compound of the formula I obtained, by which means there are obtained compounds of the formula I in which R' and/or R" are a 2-nitro-lower-alkyl group or, on continuation of hydrogenation, a 2-amino-lower-alkyl group (cp. C. J. Schmidle, R. C. Mansfield, Ind. Engng. Chem. 44, 1388 (1952); C. A. Sprang, E. F. Degering, J. Amer. chem. Soc. 64, 1063 (1942); H. B. Hass, F. Riley, The Nitroparaffins, Chem. Reviews 32, 373–420 (1943)).

Compounds of the general formula I in which R' and/or R" are carboxyl, formyl or aryl can be converted into compounds of the general formula I wherein R' and/or R" are amino or cyano and/or formamido, or monosubstituted carbamoyl and/or acylamino, by reacting corresponding compounds of the general formula I with hydrazoic acid in the presence or absence of additional inorganic acids, for example mineral acids, such as hydrochloric acid or, in particular, sulfuric acid (H. Wolff, Organic Reactions 3,307 (1946)).

Compounds of the general formula I in which R' and/or R" are formyl or acyl can be converted into compounds of the formula I wherein R' and/or R" are unsubstituted or disubstituted 2-oxiranyl by reacting a corresponding starting material of the formula I with diazomethane, and converting the resulting mono- or bis-diazoniumbetain compound, in a manner known per se, into compounds of the general formula I in which R' and/or R" are disubstituted 2-oxiranyl, methylene-homologous acyl or acylmethyl (cp. B. Eistert, Ang. Ch. 54, 99, 124 (1941); Ang. Ch. 55, 118 (1942)).

Compounds of the general formula I in which at least one of the symbols $R_1$, $R_2$, $R_3$, $R_4$ and $R_5$ is hydrogen and/or at least one of the symbols R' and R" is free hydroxyl, and the remaining symbols have the meanings defined under the formula I, can also be obtained by performing solvolysis or reduction, particularly hydrogenolysis, in a compound of the general formula I in which at least one of the symbols $OR_1$, $OR_2$, $OR_3$, $OR_4$, $OR_5$, R' and R" is an ether group which can be readily solvolysed or readily detached by reduction, in particular which can be readily hydrogenolysed, or at least one of the symbols $OR_1$, R' and R" is an acyloxy group which can be readily solvolysed or hydrogenolysed, or in a compound of the general formula III

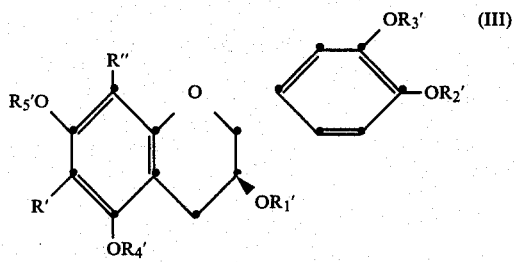

in which at least one of the symbols $OR_2'$, $OR_3'$ $OR_4'$ and $OR_5'$ is an acyloxy group which can be readily solvolysed or hydrogenolysed, and the remaining symbols have the meanings given under the formula I or $OR_2$, $OR_3$, $OR_4$ and $OR_5$, and $R_1$, R' and R" likewise have the meanings defined under the formula I.

An ether or acyloxy group which can be readily solvolysed or hydrogenolysed is for example an ether or acyloxy group which is detachable by solvolysis, including hydrolysis, acidolysis or alcoholysis, or by means of reduction, including hydrogenolysis.

An acyloxy group detachable by solvolysis is for example an acyloxy group in which the acyl moiety is the radical of an organic carboxylic acid, for example lower alkanoyl, such as acetyl, halo-lower-alkanoyl, such as haloacetyl, for example chloroacetyl, or carbamoyl, or aroyl, such as benzoyl, also the acyl moiety is the radical of a semi-ester of carbonic acid, such as lower alkoxycarbonyl, for example methoxycarbonyl, ethoxycarbonyl or tert-butyloxycarbonyl, 2-halo-lower-alkoxycarbonyl, for example 2,2,2-trichloroethoxycarbonyl or 2-iodoethoxycarbonyl, unsubstituted or substituted 1-phenyl-lower-alkoxycarbonyl, for example benzyloxycarbonyl or diphenylmethoxycarbonyl, or aroylmethoxycarbonyl, for example phenacyloxycarbonyl, also an unsubstituted or substituted 1-polyphenyl-lower-alkyl group wherein substituents of the phenyl moiety can be for example lower alkyl or lower alkoxy, such as methyl or methoxy, and in particular trityl, or an organosilyl radical, especially trimethylsilyl.

An ether group which is detachable by solvolysis is for example lower alkoxy, for example methoxy or ethoxy, or a 1-phenyl-lower-alkoxy group, such as benzyloxy. These radicals can be substituted by lower alkoxy, for example methoxy or ethoxy, or lower-alkoxyethoxy, for example methoxyethoxy.

Benzyloxy radicals as detachable ether groups can be unsubstituted or substituted by one or more substituents, for example lower alkyl, such as methyl, ethyl, isopropyl or n-propyl, halogen, for example chlorine or bromine, or lower alkoxy, for example methoxy or ethoxy. These substituents are situated preferably in the ortho position or in the para-position.

Likewise detachable by solvolysis, particularly by hydrolysis or alcoholysis, in an acid medium are for their part aliphatic ether groups substituted in the α-position by an ether group, such as ethoxymethoxy, butoxymethoxy or 1-ethoxyethoxy, and particularly analogous cyclic radicals, for example 1-oxacycloalkan-2-yloxy groups, especially tetrahydropyran-2-yloxy, also for example 4-methoxytetrahydropyran-4-yloxy.

When the solvolysis of the ether or acyloxy groups is performed by hydrolysis, this is carried out, depending on the nature of the detachable groups, in the presence of an organic acid, such as p-toluenesulfonic acid, or a mineral acid, such as hydrochloric acid or sulfuric acid, or in the presence of an alkali metal- or alkaline-earth metal-hydroxide or -carbonate, or in the presence of ammonia or of an amine, such as isopropylamine, or hydrazine hydrate. If solvolysis is performed by means of one of the above-mentioned acids in an alcohol, for example by means of p-toluenesulfonic acid in ethyl alcohol, solvolysis is performed by alcoholysis.

Ether groups, for example lower alkoxy groups, in particular methoxy or ethoxy, can be detached in solution or in the melt by means of a metal halide, such as aluminium halide or boron halide, for example aluminium trichloride, aluminium tribromide, boron trichloride or boron tribromide. Suitable solvents are for example benzene, nitrobenzene or ethylene chloride (cp. J. Chem. Soc. (1961), 1008; Ber. (1943), 76B, 900; J. Org. Chem. (1962), 27, 2037; Ber. 93 (1960), 2761; J. Am. Chem. Soc. (1968), 24,2289; and Tetrahedron Letters (1966), 4155).

Acyloxy groups detachable by acidolysis are those in which the acyl moiety is an acid radical of semi-esters of carbonic acid, for example tert-lower-alkoxycarbonyl or unsubstituted or substituted diphenylmethoxycarbonyl. Also ether groups, for example tert-lower alkoxy groups, can be detached by acidolysis. Detachment by acidolysis can be performed by treatment with suitable strong organic carboxylic acids, such as lower-alkanecarboxylic acids unsubstituted or substituted by halogen, especially by fluorine, particularly trifluoroacetic acid (if necessary in the presence of an activating agent, such as anisole), as well as with formic acid. Where no prior mention is made, the above reactions are performed in the presence of a solvent or solvent mixture, suitable reactants also being able to act as such.

An ether group detachable by reduction, especially by hydrogenolysis, is in particular an α-aryl-lower-alkyl group, such as an unsubstituted or substituted 1-phenyl-lower-alkyl group, wherein lower alkyl has up to 7 carbon atoms, and wherein substituents, especially of the phenyl moiety, can be for example lower alkyl or lower alkoxy having in each case up to 7 carbon atoms, for example methyl or methoxy, and more especially however benzyl.

The reductive detachment of the ether groups $OR_1$, $OR_2$, $OR_3$, $OR_4$, $OR_5$, $R'$ or $R''$ can be performed in particular for example by treatment with catalytically activated hydrogen, such as hydrogen in the presence of a suitable hydrogenating catalyst, for example a nickel, platinum or palladium catalyst, and also a rhodium or ruthenium catalyst; or the process is performed with a hydride reducing agent, for example lithium aluminium hydride.

By acyloxy radicals detachable by hydrogenolysis are meant those groups which are detached by treatment with a chemical reducing agent (especially with a reducing metal or a reducing metal compound). Such radicals are in particular 2-halo-lower-alkoxycarbonyloxy, such as 2,2,2-trichloroethoxycarbonyloxy, which are detached for example with a reducing heavy metal, for example zinc, or with a reducing heavy metal salt, such as a chromium(II) salt, for example chromium(II)-chloride or -acetate, usually in the presence of an organic carboxylic acid, such as formic acid or acetic acid.

The above reduction reactions are performed in a manner known per se, usually in the presence of an inert solvent and, if necessary, with cooling or heating, for example in a temperature range of about −20° to about 150° C., and/or in a closed vessel under pressure.

Depending on the ether or acyloxy group present, there is preferably selected the most mild of the described solvolysis or hydrogenolysis methods, in order to avoid changes in the flavone structure.

There can be obtained moreover by these solvolysis or hydrogenolysis methods compounds of the general formula I wherein $R'$ and/or $R''$ can also be a primary or secondary amino group, the starting materials in this case being compounds of the general formula I in which $R'$ and/or $R''$ are an amino group protected by at least one protective group.

An amino protective group is in particular an acyl group, such as acyl of an aliphatic, aromatic or araliphatic carboxylic acid, especially lower alkanoyl, for example acetyl or propionyl, or aroyl, for example benzoyl, or acyl of formic acid or of a carbonic acid semi-derivative, for example of a carbonic acid semi-ester, such as formyl, lower alkoxycarbonyl, for example ethoxycarbonyl or tert-butyloxycarbonyl, or aryl-lower-alkoxycarbonyl, for example benzyloxycarbonyl.

The detachment of an acyl radical used as an amino protective group can be performed in a manner known per se, for example by solvolysis, particularly by means of alcoholysis, also by means of hydrolysis. The detaching of an acyl radical by alcoholysis can be carried out for example in the presence of a strong basic agent, at elevated temperature, for example at about 50° C. to about 120° C. There is used in particular a lower alkanol, for example n-butanol or ethanol, and as a strong base an alkali metal lower alkanolate, for example a sodium or potassium lower alkanolate, for example -n-butylate or -ethylate, or an alkali metal hydroxide, for example sodium or potassium hydroxide.

Amino protective groups, for example lower-alkoxycarbonyl groups, such as tert-butyloxycarbonyl, can be detached particularly gently by acidolysis, for example by treatment with trifluoroacetic acid.

A further amino protective group which can be especially mildly detached is an ethoxycarbonyl group which carries in the β-position a silyl group substituted by three hydrocarbon radicals, such as a triphenylsilyl, dimethylbutyl-silyl or in particular trimethylsilyl group. A β-(trimethylsilyl)-ethoxycarbonyl group of this kind forms with the amino group to be protected a corresponding β-trimethylsilylethoxycarbonylamino group, which can be detached, under mild conditions, by reaction with fluoride ions. Reagents releasing fluoride ions are for example fluorides of quaternary organic bases, such as tetraethylammonium fluoride.

It is to be ensured that only those amino protective groups are used which can be detached selectively with retention of the desired structure of the compounds of the general formula I.

Compounds of the formula I in which at least one of the groups $OR_1$, $OR_2$, $OR_3$, $OR_4$, $OR_5$, $R'$ or $R''$ corresponds to one of the ether groups defined above, and the other symbols have the meanings given in the foregoing, can be obtained by reacting a compound of the formula I, in which at least one of the above-mentioned symbols is a hydroxyl group which is free, metallised, or esterified with a hydrohalic acid, with a compound of the formula IV $$X\text{-}R''' \qquad \text{(IV)}$$

wherein X is a free, metallised, or reactively esterified hydroxyl group, and $R'''$ together with an oxygen atom attached thereto corresponds to at least one of the above-defined ether groups $OR_1$, $OR_2$, $OR_3$, $OR_4$, $OR_5$, $R'$ and $R''$, or $X\text{-}R'''$ is a compound introducing the ether radical $R'''$, if at least one of the symbols $OR_1$, $OR_2$, $OR_3$, $OR_4$, $OR_5$, $R'$ or $R''$ is a free hydroxyl group.

If $X\text{-}R'''$ is a compound introducing the radical $R'''$, it can be a corresponding diazo compound, an acetal corresponding to the alcohol $R'''OH$, or a corresponding ortho ester, a corresponding oxonium, carbenium or halonium salt or a corresponding triazene compound. If the substituents from the group $OR_1$, $OR_2$, $OR_3$, $OR_4$, $OR_5$, $R'$, $R''$ or X of the formulae I and IV are a free hydroxyl group, the reaction is performed in the presence of proton donors, that is to say, by means of acid catalysis. The proton donors used are in particular strong inorganic acids or organic sulfonic acids, for example mineral acids, such as hydrohalic acids, for example hydrochloric acid, also sulfuric acid, or for example p-toluenesulfonic acid, but also Lewis acids, such as halides of boron, aluminium or zinc, for example boron trifluoride, aluminium chloride or zinc chloride. Etherification is preferably performed without an addition of solvent in the corresponding alcoholic solution, that is, in an alcohol of the formula $R'''OH$, provided this is in the liquid state at the applied temperature.

If one or more from the group $OR_1$, $OR_2$, $OR_3$, $OR_4$, $OR_5$, R' or R" is a hydroxyl group which is free or metallised, preferably metallised by an alkali metal atom, for example ONa, X is present as a reactive esterified hydroxyl group. In the reverse case, when X is a free or metallised hydroxyl group, one or more from the group $OR_1$, $OR_2$, $OR_3$, $OR_4$, $OR_5$, R' or R" is a hydroxyl group esterified with hydrohalic acid. A reactive esterified hydroxyl group X is preferably a hydroxyl group esterified by a strong mineral or sulfonic acid, such as a hydrohalic acid, sulfuric acid, lower-alkanesulfonic acid or benzene-sulfonic acid, for example hydrochloric, hydrobromic, methanesulfonic, trifluoromethanesulfonic, benzenesulfonic or p-toluenesulfonic acid. Such esters are, inter alia: lower alkyl halides, di-lower-alkyl sulfates, such as dimethyl sulfate, also fluorosulfonic acid ester, such as lower alkyl ester, for example fluorosulfonic acid-methyl ester, or unsubstituted or halogen-substituted methanesulfonic acid-lower-alkyl ester, for example trifluoromethanesulfonic acid-methyl ester. The hydroxyl group of the starting material of the formula I or IV can however also be esterified for example by a lower alkanecarboxylic acid, such as acetic acid or propionic acid. When one of the radicals from the compounds of the formula I or IV is the free hydroxyl group, etherification is performed in the presence of basic condensation agents which bind the formed acids. Such agents are carbonates or hydrogen carbonates of alkaline-earth metals or alkali metals, for example calcium or sodium carbonates or -hydrogen carbonates, or tertiary amines, for example tri-lower-alkylamines, pyridines or lower-alkylated pyridines. If the one starting material is used in the form of the metallised compound (for example $X_1 = ONa$), the reaction is performed under neutral reaction conditions. Finally, when X is a hydroxyl group esterified by a lower alkanecarboxylic acid, for example a hydroxyl group esterified by acetic acid, the reaction with a corresponding alcohol of the compound of the formula I, in which at least one of the symbols $OR_1$, $OR_2$, $OR_3$, $OR_4$, $OR_5$, R' or R" is a free hydroxyl group, can be performed in an acid medium, preferably in the presence of a mineral acid, for example a hydrohalic acid, such as hydrochloric acid. The reactions are performed, if necessary, with the addition of an inert solvent, such as an optionally halogenated (such as chlorinated) aliphatic, cycloaliphatic or aromatic hydrocarbon, for example methylene chloride, of an ether, such as dioxane or tetrahydrofuran, or of a mixture of these solvents.

The above-described etherification reaction can be considerably accelerated by phase-transfer catalysis [cp. Dehmlow, Angewandte Chemie, Vol. 5, p. 187 (1974)]. Suitable phase-transfer catalysts are quaternary phosphonium salts and particularly quaternary ammonium salts, such as unsubstituted or substituted tetraalkylammonium halides, for example tetrabutylammonium chloride, -bromide or -iodide, or benzyltriethylammonium chloride, used in catalytic or up to equimolar amounts. The organic phase used can be any solvent immiscible with water, for example one of the optionally halogenated (such as chlorinated), lower aliphatic, cycloaliphatic or aromatic hydrocarbons, such as tri- or tetrachloroethylene, tetrachloroethane, carbon tetrachloride, chlorobenzene, toluene or xylene. Alkali metal carbonates or -hydrogen carbonates suitable as condensation agents are for example: potassium or sodium carbonate or -hydrogen carbonate, alkali metal phosphates, for example potassium phosphate, and alkali metal hydroxides, for example sodium hydroxide.

Compounds of the formula I wherein at least one of the symbols $OR_1$, $OR_2$, $OR_3$, $OR_4$, $OR_5$, R' or R" is the free hydroxyl group can be etherified, as already stated above, also by reaction with corresponding diazo compounds. Such compounds are for example: diazo-lower-alkanes, such as diazomethane, diazoethane or diazo-n-butane, but also phenyl-diazo-lower-alkanes, for example phenyl-diazomethane. These reagents are applied in the presence of a suitable inert solvent, such as an aliphatic, cycloaliphatic or aromatic hydrocarbon, such as hexane, cyclohexane, benzene or toluene, or in the presence of a halogenated aliphatic hydrocarbon, for example methylene chloride, or an ether, such as di-lower-alkyl ether, for example diethyl ether, or in the presence of a cyclic ether, for example tetrahydrofuran or dioxane, or a solvent mixture, and, depending on the diazo reagent, with cooling, at room temperature or with slight heating, also, if necessary, in a closed vessel and/or under an inert gas, for example in a nitrogen atmosphere.

When at least one of the symbols $OR_1$, $OR_2$, $OR_3$, $OR_4$, $OR_5$, R' or R" is hydroxyl, further etherifying agents are suitable acetal compounds, for example gem-di-lower-alkoxy-lower alkanes, such as 2,2-dimethoxypropane, which are used in the presence of strong organic sulfonic acids, such as p-toluenesulfonic acid, and of a suitable solvent, such as a di-lower-alkyl- or lower-alkylenesulfoxide, for example dimethyl sulfoxide; or suitable ortho esters, for example orthoformic acid-tri-lower-alkyl esters, for example orthoformic acid-triethyl esters, which are used in the presence of a strong mineral acid, for example sulfuric acid, or a strong organic sulfonic acid, such as p-toluenesulfonic acid, and a suitable solvent, such as an ether, for example dioxane.

When at least one from the group of symbols $OR_1$, $OR_2$, $OR_3$, $OR_4$, $OR_5$, R' or R" is the free hydroxyl group, further etherifying agents are corresponding tri-substituted oxonium salts (so-called Meerwein salts), or disubstituted carbenium or halonium salts, wherein the substituents are the etherifying radicals R, for example tri-lower-alkyloxonium salts, and di-lower-alkoxycarbenium or di-lower-alkylhalonium salts, especially the corresponding salts with complex, fluorine-containing acids, such as the corresponding tetrafluoroborates, hexafluorophosphates, hexafluoroantimonates or hexachloroantimonates. Such reagents are for example: trimethyloxonium- or triethyloxonium-hexafluoroantimonate, -hexachloroantimonate, -hexafluorophosphate or -tetrafluoroborate, dimethoxycarbeniumhexafluorophosphate or dimethylbromoniumhexafluoroantimonate. These etherifying agents are used preferably in an inert solvent, such as in an ether or a halogenated hydrocarbon, for example diethyl ether, tetrahydrofuran or methylene chloride, or in a mixture thereof, in necessary in the presence of a base, such as an organic base, for example a, preferably sterically hindered, tri-lower-alkylamine, for example N,N-diisopropyl-N-ethylamine, and with cooling, at room temperature or with slight heating, for example at about −20° to about 50° C., if necessary in a closed vessel and/or in an inert gas, for example in a nitrogen atmosphere.

When one of the substituents $OR_1$, $OR_2$, $OR_3$, $OR_4$, $OR_5$, R' or R" of the compound of the formula I is a free hydroxyl group, further etherifying agents are finally corresponding 1-substituted 3-aryltriazene compounds wherein the substituent is the etherifying radical R, and aryl is preferably unsubstitued or substituted phenyl, for example lower alkylphenyl, such as 4-methylphenyl. Such triazene compounds are 3-aryl-1-lower-alkyltriazenes, for example 3-(4-methylphenyl)-1-methyl-triazene, 3-(4-methylphenyl)-1-ethyl-triazene or 3-(4-methylphenyl)-1-isopropyl-triazene. These reagents are used usually in the presence of inert solvents, such as optionally halogenated hydrocarbons or ethers, for example benzene, or solvent mixtures, and with cooling, at room temperature and preferably at elevated temperature, for example at about 20° to about 100° C., if necessary in a closed vessel and/or in an inert gas, for example in a nitrogen atmosphere.

In the compounds of the formula I, a hydroxyl group esterified with a hydrohalic acid is for example a chlorine, bromine or iodine atom.

The conversion of a free hydroxyl group into a hydroxyl group esterified by a hydrohalic acid, that is to say, into a halogen atom, is usually performed by treatment with a halogenating, especially chlorinating, agent. Such agents are for example: thionyl chloride, thionyl bromide, phosphorus tribromide, phosphorus oxybromide or -chloride or phosphorus pentachloride, which are customarily used in the presence of an inert solvent or diluent, for example tetrahydrofuran, dioxane, methylene chloride or dimethyl sulfoxide.

Compounds of the general formula I or of the above-mentioned formula III, in which at least one of the symbols $OR_1$, $OR_2$, $OR_3$, $OR_4$, $OR_5$, R′, R″, $OR_2′$, $OR_3′$, $OR_4′$ or $OR_5′$ are an acyloxy group, can be obtained by converting a compound of the formula I, in which at least one of the symbols $OR_1$, $OR_2$, $OR_3$, $OR_4$, $OR_5$, R′ or R″ is a free hydroxyl group, with an acylating agent introducing the desired acyl radical of an organic carboxylic acid, into an acyloxy group. Such agents are for example corresponding carboxylic acids or reactive derivatives thereof, such as anhydrides or acid halides, for example acid chlorides or acid bromides. The reactions can be performed optionally in the presence of condensation agents, in the case of free carboxylic acids, for example, in the presence of cabodiimide compounds, such as dicyclohexylcarbodiimide, or carbonyl compounds, such as diimidazolylcarbonyl. With the use of acid derivatives, for example acid halides, the reactions are performed advantageously in the presence of a basic agent, for example a tri-lower-alkylamine, such as triethylamine, or in the presence of a heterocyclic base, for example pyridine.

Within the limits of the definition of the final products, it is possible to modify substituents in the compounds obtained. Thus, in a product of the formula I, the substituents $OR_1$, $OR_2$, $OR_3$, $OR_4$, $OR_5$, R′ or R″ can be exchanged, by treatment with another alcohol of the formula R‴OH, optionally in the presence of an acid, for another substituent OR‴. Lower alkoxy groups for example can therefore be converted in a known manner, for example by reaction with a diazo-lower-alkane, or by reaction with a lower alkyl halide, such as iodide or bromide, for example in the presence of silver oxide or silver carbonate, into another lower alkoxy group.

The above-mentioned reactions are performed by methods known per se, in the presence or absence of diluents, preferably in those which are inert to the reagents and which dissolve them, catalysts, condensation agents or neutralising agents, and/or in an inert atmosphere, with cooling, at room temperature or at elevated temperature, preferably at the boiling point of the employed solvent, and under normal or elevated pressure.

Compounds of the general formula I in which R′ and/or R″ are carboxyl, or in which carboxyl is contained as a substituent, and salts of such compounds with bases can be obtained by liberation of the carboxyl group(s) and, optionally, subsequent salt formation with bases. The liberation of the carboxyl group(s) can be effected in a manner known per se, particularly by hydrolysis or by reduction, especially by hydrogenolysis. Funtionally modified carboxyl groups suitable for hydrolysis are for example ester groups, in particular lower alkyl ester groups, i.e. lower alkoxycarbonyl, also for example unsubstituted or (analogously to benzyloxy) substituted benzyloxycarbonyl, also phenacyloxycarbonyl or phthalimidomethoxycarbonyl, and, as a further type, amide and thioamide groups, and corresponding derivatives of saturated nitrogen-containing heterocycles, for example carbamoyl, mono- and di-lower-alkylcarbamoyl, lower alkylenecarbamoyl or morpholinocarbonyl, and thio-analogs, thereof, for example the thiocarbamoyl or morpholinocarbonyl preferentially obtained in the Willgerodt-Kindler reaction. Also suitable are nitrile groups and the imido esters preferably produced from such groups in a manner known per se, particularly imido-lower-alkyl ester groups.

The hydrolysis reaction is preferably performed in an aqueous or organic-aqueous, acid or basic medium, at room temperature up to the boiling temperature of the reaction medium. It can be performed for example in aqueous lower-alkanolic alkali hydroxide solutions or alkali carbonate solutions. From the alkali metal salt solutions of the free carboxylic acids firstly formed, it is possible either to liberate the acids by acidification, or to obtain directly, by concentration or by evaporation and subsequent recrystallisation, the corresponding pure alkali metal salt. The acid medium used can be for example sulfuric acid diluted with water, such as 60–70% sulfuric acid, or aqueous or lower-alkanolic-aqueous hydrochloric acid. An acidified medium results also when an imido-lower-alkyl ester hydrochloride formed from a nitrile by treatment with hydrogen chloride and a lower alkanol is treated directly with water, preferably at elevated temperature.

Groups convertable by reduction into free carboxyl are both groups which, to the required end, can be detached by chemical reduction, and such groups which can be detached by reduction by means of catalytically activated hydrogen, that is, by hydrogenolysis. The first group includes in particular 2-halogenated lower-alkyl ester groups, such as 2,2,2-trichloroethoxycarbonyl, also unsubstituted or (analogously to benzyloxy) substituted phenacyl, as well as phthalimidomethyl, from which the carboxyl group can be liberated for example by treatment with reducing metals and acids, for example with zinc in acetic acid at elevated temperature, for example at the boiling temperature. Ester groups detachable by hydrogenolysis are for example α-aryl-lower-alkyl ester groups, especially benzyloxycarbonyl unsubstituted or substituted in the ring in the manner described above for benzyloxy, also unsubstituted or analogously substituted phenacyl, which can be cleaved by treatment with hydrogen in the presence of a suitable hydrogenating catalyst, for example a nickel, platinum or palladium catalyst, and also a rhodium or ruthenium catalyst.

Both the hydrolytic and the reductive or hydrogenolytic liberation of carboxyl groups can be effected also in the same operation as the corresponding liberation of hydroxyl groups $OR_1$, $OR_2$, and so forth, from acyloxy groups, or from ether groups which can be detached by reduction or can by hydrogenolysed.

Compounds of the general formula I in which R' and/or R'' either are functionally modified carboxyl, or contain this as substituent, can be obtained from corresponding compounds wherein R' and/or R'' are free or differently functionally modified carboxyl, by conversion of the last-mentioned groups in a manner known per se. The desired functionally modified carboxyl is for example esterified carboxyl, especially lower alkoxycarbonyl or amidated carboxyl, particularly carbamoyl which is unsubstituted or substituted by alkyl, di-loweralkylaminoalkyl, and/or phenyl which is unsubstituted or in its turn substituted in the ring by halogen, lower alkyl or lower alkoxy. To carry out the above-mentioned process, compounds of the general formula I for example in which R' and/or R'' either are carboxyl, or contain carboxyl as substituent, or reactive functional derivatives of such compounds, for example anhydrides, particularly mixed anhydrides, such as those with hydrohalic acids or with monoesters of carbonic acid, also activated esters, for example cyanomethyl esters or p-nitrobenzyl esters, and also lower alkyl esters, are reacted with hydroxyl compounds, especially lower alkanols, or with ammonia or primary or secondary amines. It is also possible to react salts, particularly alkali metal salts or alkaline-earth metal salts, of free carboxylic acids with reactive esters of hydroxyl compounds, especially of lower alkanols, such as hydrohalic acid esters, or esters with organic sulfonic acids, for example lower-alkanesulfonic acid or arenesulfonic acid esters, such as methanesulfonic acid esters or p-toluenesulfonic acid esters; or with carbamic acid halides derived from secondary amines, in particular carbamic acid chlorides; or free carboxylic acids can also be reacted with diazo-lower-alkanes to lower alkyl esters, or with isocyanates to N-monosubstituted amides. Furthermore, it is also possible to convert nitriles, in a manner known per se, into N-unsubstituted amides or into esters, especially lower alkyl esters.

The reaction of free carboxylic acids embraced by the general formula I with hydroxyl compounds is performed advantageously in the presence of an acid catalyst splitting off water, such as a protonic acid, for example hydrochloric or hydrobromic acid, sulfuric, phosphoric or boric acid, benzenesulfonic or toluenesulfonic acid, or a Lewis acid, for example of boron-trifluoride etherate, in an excess of the employed hydroxyl compound and/or in an inert solvent, for example in a hydrocarbon of the benzene series, such as benzene or toluene, in a halogenated hydrocarbon, such as chloroform, methylene chloride or chlorobenzene, or in an ether-like solvent, such as tetrahydrofuran, if necessary with removal by distillation, for example azeotropic distillation, of the water released during the reaction. The reactions can also be performed in the presence of other water-binding condensation agents, for example carbodiimides substituted by hydrocarbon radicals, such as N,N'-diethyl-, N,N'-dicyclohexyl- or N-ethyl-N'-(3-dimethylaminopropyl)-carbodiimide, in inert organic solvents, for example in the aforementioned. Halides and other mixed anhydrides are reacted for example in the presence of acid-binding agents, for example organic, especially tertiary, nitrogen bases, for example triethylamine, N,N-diisopropyl-N-ethylamine or pyridine, or in the presence of inorganic bases, for example alkali metal- or alkaline-earth metal-hydroxides or -carbonates, such as sodium, potassium or calcium hydroxide or -carbonate, in inert organic solvents, for example in the above-mentioned, and if necessary with heating. The reactions of reactive esters of carboxylic acids embraced by the general formula I, for example the cyanomethyl esters or p-nitrobenzyl esters, with hydroxyl compounds are performed for example in a solvent inert to the reactants, for example in a hydrocarbon, such as toluene or xylene, in an ethereal solvent, such as tetrahydrofuran or dioxane, or at moderate temperatures also an ester, such as ethyl acetate, in the temperature range of about 0° to about 120° C., preferably at room temperature up to about 60° C. For transesterification of lower alkyl esters of carboxylic acids embraced by the general formula I, there are preferably used hydroxyl compounds having a boiling point clearly above that of the esterified lower alkanols, and the reaction is performed for example in an excess of the hydroxyl compound and/or in an inert organic solvent preferably having a boiling point clearly above that of the lower alkanol, preferably in the presence of a catalyst, for example an alkali metal-lower-alkoxide, such as sodium or potassium methoxide or -ethoxide, at elevated temperature, and preferably with removal of the liberated lower alkanol by distillation. The hydrolysis of imido esters, especially imido-lower-alkyl esters, of carboxylic acids embraced by the general formula I is performed for example by means of aqueous mineral acid, such as hydrochloric acid or sulfuric acid, whereby for example the imido ester hydrochlorides obtained by the addition reaction of hydrogen chloride with nitriles and reaction of the product with anhydrous hydroxyl compounds, particularly lower alkanols, can, after the addition of water, be hydrolysed directly to the corresponding esters; or from a mixture for example of nitrile, hydroxyl compound and sulfuric acid of suitable water content, there can be obtained, without isolation of the imido ester formed in situ, the corresponding ester embraced by the general formula I.

The reaction of free carboxylic acids embraced by the general formula I with ammonia or with primary or secondary amines is performed for example in the presence of the above-mentioned water-binding agents and in the inert organic solvents mentioned above; it is also possible however to convert the ammonium salts, formed from the free carboxylic acids and ammonia or amines, by heating, optionally in a suitable organic solvent having a medium or higher boiling point, for example xylene, chlorobenzene or 1,2,3,4-tetrahydronaphthalene, and removal, by distillation, optionally azeotropic distillation, of the water liberated during the reaction, into amides embraced by the general formula I.

Suitable reactive functional derivatives of carboxylic acids embraced by the general formula I for reaction with ammonia or with primary or secondary amines, and appertaining condensation agents and solvents are essentially the same as those given above for reactions with hydroxyl compounds, with the difference that the acid-binding agent used can also be an excess of the ammonia to be reacted, and the acid-binding agent and optionally sole reaction medium used can be, in place of others, that is to say, tertiary organic bases, also an excess of the amine to be reacted. The partial hydrolysis of the corresponding nitriles, which is a further possibility for the formation of N-unsubstituted amides, can be performed for example by means of aqueous mineral acids, such as hydrochloric acid or dilute sulfuric acid, at room temperature or at a moderately elevated temperature. Furthermore, nitriles can be converted into the corresponding N-unsubstituted amides by treatment with peroxides or peroxy acids, for example hydrogen peroxide, in an inert reaction medium, for example in an aqueous lower alkanol, with moderate heating.

In the process according to the invention, those starting materials of the formulae II, III and IV are in general to be reacted and those process measures applied which do not yield compounds of the general formula I which have been excluded in the second definition of this formula for the novel compounds as being known per se.

Acid addition salts of compounds of the formula I are obtained in customary manner, for example by treating with an acid or a suitable anion exchanger. The resulting salts can be converted into the free compounds in a manner known per se, for example by treating with a suitable basic agent, for example a metal hydroxide, ammonia or a hydroxyl ion exchanger. On the other hand, compounds having a phenolic hydroxy group can be converted into an alkali metal salt in a manner known per se by treating, for example, with an alkali metal hydroxide. The free compounds can be obtained by treating with an acid.

The therapeuctically acceptable salts mentioned above are preferred. These or other salts, for example the picrates, can also be used in the purification of free bases. The bases are converted into their salts, the salts are separated and the bases are liberated from the salts. Owing to the close relationships between the novel compounds in free form and in the form of their salts, hereinbefore and hereinafter there shall optionally be understood by free compounds and salts, where appropriate with regard to meaning and purpose, also the corresponding salts and free compounds, respectively.

Starting materials and end products that are isomeric mixtures can be separated into the individual isomers by methods known per se, for example by fractional distillation, crystallisation and/or chromatography. Racemic products can be separated into the optical antipodes, for example by chromatography and/or separation of their diastereoisomeric salts, for example by fractional crystallisation of the d- or l-camphor-sulphonates, -mandelates, -tartrates or -dibenzoyltartrates.

The invention relates also to modifications of the present process, according to which an intermediate obtainable at any stage of the process is used as starting material and the remaining process steps are carried out, or the process is discontinued at any stage, or according to which a starting material is formed under the reaction conditions, or in which a starting material is used in the form of a salt or a reactive derivative. The invention also comprises novel intermediates resulting therefrom.

In the process of the present invention the starting materials used are preferably those which result in the compounds described at the beginning as being especially valuable.

The starting materials used in the process for the manufacture of the compounds of the present invention are known or, if they are novel, they can be manufactured by methods known per se, for example in a manner analogous to that described in the Examples. The invention relates also to novel starting materials.

The pharmaceutical preparations according to the invention contain at least one compound of the general formula I or a salt thereof as the active substance together with a customary pharmaceutical carrier. The type of carrier depends largely on the field of use. The pharmaceutical compositions according to the invention which contain, as active substances, compounds of the formula I can be administered orally, parenterally or rectally.

For oral treatment there come into consideration, especially, solid dosage unit forms, such as tablets, dragées and capsules, which preferably contain between 10 and 90% of an active substance of the general formula I or a salt in order to allow administration to warm-blooded animals of daily doses of from 1 to 50 mg/kg. For the manufacture of tablets and dragée cores, the compounds of the general formula I are combined with solid, pulverulent carriers, such as lactose, saccharose, sorbitol, maize starch, potato starch or amylopectin, cellulose derivatives or gelatine, preferably with the addition of lubricants, such as magnesium or calcium stearate, or polyethylene glycols of a suitable molecular weight. Dragée cores are subsequently coated, for example with concentrated sugar solutions which may contain, in addition, gum arabic, talc and/or titanium dioxide, or with a lacquer dissolved in readily volatile organic solvents or solvent mixtures. Colouring substances can be added to these coatings, for example for indicating different doses of active substance. Soft gelatine capsules and other closed capsules consist, for example, of a mixture of gelatine and glycerin and may contain, for example, mixtures of a compound of the formula I and polyethylene glycol. Dry-filled capsules contain, for example, granules of an active substance with solid, pulverulent carriers, such as, for example, lactose, saccharose, sorbitol, mannitol; starches, such as potato starch, maize starch or amylopectin, cellulose derivatives and gelatine and also magnesium stearate or stearic acid.

Unit dosage forms that come into consideration for rectal administration are, for example, suppositories which consist of a combination of an active substance with a suppository base based on natural or synthetic triglycerides (for example cocoa butter), polyethylene glycols or suitable higher fatty alcohols, and gelatine rectal capsules which contain a combination of the active substance with polyethylene glycols.

Ampoule solutions for parenteral administration especially for intramuscular or intravenous administration, contain a compound of the formula I or a salt thereof in a concentration of preferably 0.5 to 5% as an aqueous dispersion prepared with the aid of customary sulubilisers and/or emulsifiers, and, optionally, stabilisers, or preferably as an aqueous solution of a pharmaceutically acceptable water-soluble salt of a compound of the general formula I.

The concentration of the active substance for liquids that are to be taken orally, such as syrups or elixirs, is so selected that a single dose can easily be measured, for example as the contents of a teaspoon or a measuring spoon of, for example, 5 ml, or also as a multiple of that volume.

The following Examples (a) to (c) are intended to illustrate the manufacture of some typical forms of administration, but do not in any way represent the only embodiments of those forms of administration.

(a) 250 g of active substance are mixed with 550 g of lactose and 292 g of potato starch, and the mixture is moistened with an alcoholic solution of 8 g of gelatine and granulated by being passed through a sieve. After drying, 60 g of talc, 10 g of magnesium stearate and 20 g of colloidal silica are added and the mixture is pressed to form 10,000 tablets each weighing 119 mg and each containing 25 mg of active substance, which may, if desired, be provided with dividing notches of a finer adjustment of the dosage.

(b) A granulate is prepared from 100 g of active substance, 379 g of lactose and the alcoholic solution of 6 g of gelatine, which, after being dried, is mixed with 10 g of colloidal silica, 40 g of talc, 60 g of potato starch and 5 g of magnesium stearate and pressed to form 10,000 dragée cores. These are subsequently coated with a concentrated syrup consisting of 533.5 g of cryst, saccharose, 20 g of shellac, 75 g of gum arabic, 250 g of talc, 20 g of colloidal silica and 1.5 g of colouring substance, and dried. The resulting dragées each weight 150 mg and each contain 10 mg of active substance.

(c) 25 g of active substance and 1975 g of finely ground suppository base (for example, cocoa butter) are thoroughly mixed and then melted. 1000 suppositories of 2 g are cast from the melt which has been kept homogenous by stirring. They each contain 25 mg of active substance.

The following Examples serve to illustrate the invention but are not intended to limit the scope thereof in any way. Temperatures are given in degrees Centigrade and data regarding parts relate to parts by weight. Unless defined otherwise, the evaporation of solvents is carried out under reduced pressure, for example between approximately 0.1 and 15 mm Hg.

EXAMPLE 1

A suspension of 0.6 g palladium chloride in 90 ml methyl alcohol is hydrogenated with vigorous stirring. When hydrogen absorption has stopped, the methyl alcohol is removed by suction, and the catalyst is rinced twice in ethyl acetate. A solution of 2.3 g 8-methyl-3,5,7,3',4'-penta-O-benzyl-(+)-cyanidan-3-ol in 90 ml ethyl acetate is added and hydrogenated. When the hydrogen is no longer taken up, the solution is purified with nitrogen and the catalyser filtered and washed with ethyl acetate. The filtrates are combined and completely evaporated. The residue is placed in 5 ml water and then almost completely evaporated. The residue is finally vacuum dried over phosphorous pentoxide to constant weight. One obtains 8-methyl-(+)-cyanidan-3-ol in the form of a white amorphous solid; m.p.=205° C.

EXAMPLE 2

A solution of 1.0 g 8-formyl-3,5,7,3',4'-penta-O-benzyl(+)-cyanidan-3-ol in 90 ml ethyl acetate is hydrogenated over 500 mg palladium 5% on activated charcoal. Hydrogenation takes 4 hours. After filtration and evaporation of the solvent under vacuum, the product is purified on a silicagel chromatographic column (eluant=benzene/diethylether 2:1). The product is dried under vacuum and 8-methyl(+)-cyanidan-3-ol is obtained; m.p.=205° C.

EXAMPLE 3

41 g 8-bromo-3,5,7,3',4'-penta-O-benzyl-(+)-cyanidan-3-ol is dissolved in 400 ml anhydrous tetrahydrofuran. After cooling to −70° C., 34 ml of a 1.47M solution of n-butyl lithium in n-hexane are added. After 10 minutes, 13 ml previously condensed methyl chloride are slowly introduced. The temperature is allowed to rise to 20° C. whilst maintaining slight bubbling of methyl chloride gas. After hydrolysing with 3 ml water, the tetrahydrofuran is evaporated off and 350 ml dichloromethane is added. The resulting solution is washed with water, dried over magnesium sulphate, then completely evaporated. The residue obtained is recrystallised in a mixture of chloroform and methyl alcohol. One obtains 8-methyl-3,5,7,3',4'-penta-O-benzyl-(+)-cyanidan-3-ol; m.p.=84°–86° C.

Instead of methyl chloride, one can also use dimethyl sulphate (9.5 ml) or methyl iodide (6.2 ml).

EXAMPLE 4

A solution of 2 g 8-(1-hydroxy propyl)-3,5,7,3',4'-penta-O-benzyl-(+)-cyanidan-3-ol in 200 ml ethyl acetate is hydrogenated over 1 g palladium 10% on activated charcoal. Hydrogenation lasts for 3 hours at 50° C. After the usual treatment (see example 1) one obtains 8-n-propyl-(+) -cyanidan-3-ol in the form of a white solid; m.p.=134° C.

EXAMPLE 5

A solution of 3.6 g 8-allyl-3,5,7,3',4'-penta-O-benzyl-(+)-cyanidan-3-ol in 360 ml ethyl acetate is hydrogenated at room temperature over 1.8 g 10% palladium on active charcoal. Hydrogenation is complete in 2 hours. After usual treatment (cf. example 1) one obtains 8-n-propyl-(+)-cyanidan-3-ol (same substance as that in example 4).

EXAMPLE 6

A solution of 22.5 g 8-(1-hydroxypropyl)-3,5,7,3',4'-penta-O-benzyl-(+)-cyanidan-3-ol in 800 ml ethyl acetate is hydrogenated at room temperature over 11.2 g palladium 10% on activated charcoal. Hydrogenation lasts for 31 hours. After the usual treatment (cf. example 1) one obtains 8-n-propyl-3-O-benzyl-(+)-cyanidan-3-ol in the form of a white solid; m.p.=61.5°–62° C.

EXAMPLE 7

A solution of 26 g 8-(butene-1-yl)-3,5,7,3',4'-penta-O-benzyl-(+)-cyanidan-3-ol in 1.5liter of a mixture (9 to 1) of ethyl acetate and ethyl alcohol is hydrogenated at room temperature over 13 g palladium 10% on activated charcoal. Hydrogenation lasts for 24 hours. After the usual treatment (cf. example 1) 8-n-butyl-(+)-cyanidan-3-ol in the form of a white solid is isolated; m.p.=178.7° C.

EXAMPLE 8

36.0 g 8-(but-1-enyl)-3-O-methyl-5,7,3',4'-tetra-O-benzyl-(+)-cyanidan-3-ol is dissolved in a mixture of 360 ml ethylacetate and 40 ml ethanol. 18.0 g 10% palladium on activated charcoal is added and the stirred mixture is hydrogenated for 24 hours. After this time, the catalyst is filtered and the solvent evaporated in vacuo to give a pale-yellow oil. After treatment in the usual manner (cf. example 1) 8-n-butyl-3-O-methyl-(+)-cyanidan-3-ol is obtained as a white solid; m.p.: 94°–95° C.

EXAMPLE 9

As example 3, but after 10 minutes, 20 ml of freshly distilled allyl bromide is slowly added. The residue is recrystallised in a mixture of chloroform and methyl alcohol. Thus one obtains 8-allyl-3,5,7,3',4'-penta-O- benzyl-(+)-cyanidan-3-ol in the form of white crystals; m.p.=79°-82° C.

EXAMPLE 10

A suspension of 0,32 g magnesium in 5 ml anhydrous ether is reflux heated with constant stirring. A solution of 1.33 g n-propyl bromide in 5 ml ether is slowly added, then reflux heating continued for 1 hour.

Afterwards a solution of 5 g 8-formyl-O-methyl-5,7,3',4'-tetra-O-benzyl-(+)-cyanidan-3-ol in 20 ml dry tetrahydrofuran is slowly added, then refluxing continued again for 15 hours. The mixture is allowed to cool to room temperature and then 20 ml water and a 2N hydrochloric acid solution are added, stirring until all mineral matter has been dissolved. The two phases are separated and the aqueous phase extracted with 30 ml ether. The combined organic solutions are washed in 50 ml water, then dried over magnesium sulphate. After vacuum evaporation of the solvents, the resulting product is crystallised twice in a mixture of ethyl alcohol and ethyl acetate. After drying under vacuum, one obtains 8-(butene-1-yl)-3-O-methyl-5,7,3',4'-tetra-O-benzyl-(+)-cyanidan-3-ol; m.p.=128°-129° C.

EXAMPLE 11

Same operational method as in example 10 but taking 5.3 g 8-formyl-3-O-butyl-3,5,7,3'-4'-tetra-O-benzyl-(+)-cyanidan-3-ol. After recrystallisation in a mixture of ethyl alcohol and ethyl acetate and drying under vacuum, one obtains 8-(butene-1-yl)-3-O-butyl-5,7,3',4'-tetra-O-benzyl-(+)-cyanidan-3-ol; m.p.=106°-107° C.

EXAMPLE 12

Same operational method as example 10, but taking 6.6 g 8-formyl-3-O-palmitoyl-5,7,3',4'-tetra-O-benzyl-(+)-cyanidan-3-ol. After passing over a silica gel chromatographic column (eluant: petroleum ether b.p. 60°-80° C./chloroform 2:1) one obtains 8-(butene-1-yl)-3-O-palmitoyl-5,7,3',4'-tetra-O-benzyl-(+)-cyanidan-3-ol as a low melting solid.

EXAMPLE 13

A solution of 13,6 g n-propyl bromide in 50 ml ehter is slowly added to a suspension of 3.2 g magnesium in 150 ml reflux heated ether. After complete disappearance of the magnesium, a solution of 57 g 8-formyl-3,5,7,3',4'-penta-O-benzyl-(+)-cyanidan-3-ol in 150 ml tetrahydrofuran is slowly added.

Reflux is maintained for 15 hours. After cooling, hydrolysis is carried out with a 2N hydrochloric acid solution and stirring until the inorganic material has dissolved. The layers are separated and the aqueous phase is extracted two times with ether. The combined organic phases are washed with water and then dried over magnesium sulphate. After evaporation, the residue is titurated in ethyl alcohol this allowing isolation of a solid. This gives after crystallisation in a mixture of ethyl alcohol and ethyl acetate, 8-(butene-1-yl)-3,5,7,3',4'-penta-O-benzyl-(+)-cyanidan-3-ol; m.p.=114°-115° C.

EXAMPLE 14

60 g acetamide is melted by heating at 95° C. under nitrogen and 2.9 g (+)-cyanidan-3-ol is added whilst stirring, then 4.28 g benzyl bromide. After stirring for 2 hours at 95° C., this is allowed to cool and 100 ml water is added and the solution extracted with ethyl acetate. The organic extract is washed with a solution of 1% sodium carbonate in water, then with water and finally dried on magnesium sulphate and filtered. The ethyl acetate is then evaporated and the resulting residue crystallised several times in a mixture of ethyl alcohol and water. 6.8-dibenzyl-(+)-cyanidan-3-ol is obtained, m.p.=126° C.

EXAMPLE 15

56,1 g of finely powdered potassium hydroxide is vigorously stirred in 70 ml dimethylsulfoxide to form a suspension. This is cooled to about +5° C. and to this are added simultaneously a solution made up of 23.5 g 6,8-dibenzyl-(+)-cyanidan-3-ol in 50 ml dimethylsulfoxide and 44.3 g benzylchloride. 45 minutes after the addition of the reagents, the mixture is allowed to obtain room temperature and stirring is continued for 75 minutes. Then the mixture is poured into crushed ice, neutralised to pH7 with 3.5N aqueous solution of sulfuric acid and extraction carried out with dichloromethane. The organic phase is washed with water, dried over anhydrous magnesium sulfate and evaporated. The residue is crystallised in a mixture of hexane and toluene; 6,8-dibenzyl-3,5,7,3',4'-penta-O-benzylcyanidan-3-ol is obtained.

EXAMPLE 16

The mother liquor of the crystallisation of 6,8-dibenzyl-(+)-cyanidan-3-ol (see example 14) is evaporated and the residue is eluted on a dry column of silicagel with a mixture of chloroform, ethyl acetate and formic acid of the following proportions by volume 5:5:1. In this way a fraction of pure 6-benzyl-(+)-cyanidan-3-ol is obtained; m.p.=174°-176° C.

EXAMPLE 17

As in example 15, but starting from 19.0 g 8-benzyl-(+)-cyanidan-3-ol and obtaining 8-benzyl-3,5,7,3',4'-penta-O-benzyl-(+)-cyanidan-3-ol; m.p.: 133°-134° C.

EXAMPLE 18

A solution of 29 g (+)-cyanidan-3-ol in 400 ml dimethylsulphoxide and 76.3 g 4-fluoro-benzyl bromide are dropped in 200 ml 2N sodium hydroxyde aqueous solution so that the temperature does not rise above 25° C. This solution is stirred at 25° C. during 1 hour and half, then it is neutralised t pH7 with a 2N hydrochloric acid aqueous solution and 500 ml water is added; a precipitate is formed, which is filtered and dissolved in ethyl acetate. The resulting liquor is washed with water, dried over anhydrous magnesium sulfate, filtered and evaporated to dryness. The residue is dissolved again in a mixture of ethyl acetate and methanol, then hydrogenated over palladium 10% on activated charcoal. After filtration and evaporation of the solvent, the remaining solid is crystallised in a mixture of methanol and water. In this way, 6,8-di-(4-fluoro-benzyl)-(+)-cyanidan-3-ol is obtained; m.p. 123° C.

EXAMPLE 19

As in example 18, but using 68.4 g benzyl bromide, and obtaining 6,8-dibenzyl-(+)-cyanidan-3-ol; m.p.: 126° C., $[\alpha]_D^{25} = -113°$ (C=0,5% in ethanol:water 95:5).

EXAMPLE 20

As in example 14, but using 3.7 g 2-methyl benzyl bromide and obtaining 6,8-di-(2-methyl benzyl)-(+)-cyanidan-3-ol; m.p.=113° C.

EXAMPLE 21

By evaporating the mother liquor after crystallisation of 6,8-di-(2-methylbenzyl)-(+)-cyanidan-3-ol (see example 20) until all the ethyl alcohol has been removed, a rubbery mass is precipitated and eliminated, then a crystalline product is filtered and then crystallised in a mixture of ethyl alcohol and water. 6-(2-methyl benzyl)-(+)-cyanidan-3-ol is obtained; m.p.: 192° C.

EXAMPLE 22

A suspension of 1.46 g magnesium in 30 ml anhydrous tetrahydrofuran is prepared under strictly anhydrous conditions and nitrogen. 10.4 freshly distilled 4-bromotoluene diluted with 10 ml dry tetrahydrofuran is then dropped in and an iodine crystal is added. After reflux heating for one hour and half, when most of magnesium has reacted, a solution of 30.7 g 8-formyl-3,5,7,3',4'-penta-O-benzyl-(+)-cyanidan-3-ol in 100 ml dry tetrahydrofuran is introduced in the reactor. Reflux heating is maintained for one and half more hour and after cooling 50 ml water is added and the mixture is neutralised with a 2N hydrochloric acid aqueous solution. The organic layer is separated and the aqueous layer is extracted with ethyl acetate. The organic solutions are combined, dried over magnesium sulphate, filtered and evaporated to dryness. The residue is dissolved in 300 ml ethyl acetate and hydrogenated over 10% palladium on activated charcoal. After filtrating the catalyst and evaporating the solvent, the residual compound is dissolved in a mixture of ethanol and water, from which crystallised 8-(4-methylbenzyl)-(+)-cyanidan-3-ol is obtained; m.p.: 200°–202° C.

EXAMPLE 23

As in example 22, but adding 10.7 g 2-bromotoluene and hydrogenating at 50° C. in 400 ml of a mixture of ethyl alcohol and ethyl acetate plus 0.1% formic acid. After crystallisation in aqueous ethyl alcohol 8-(2-methyl benzyl)-(+)-cyanidan-3-ol is obtained; m.p.: 198°–201° C.

EXAMPLE 24

A solution of 37.0 g 8-formyl-3,5,7,3',4'-penta-O-benzyl-(+)-cyanidan-3-ol in 100 ml dry tetrahydrofuran is added to a reflux heated suspension of 2.0 g lithium aluminohydride in 50 ml dry tetrahydrofuran. The mixture is refluxed for 2 hours, cooled to room temperature and water is slowly added. After filtering off the solid, this is washed in tetrahydrofuran. The combined organic phases are evaporated and the residue is crystallised twice in ethyl alcohol. After drying under vacuum, one obtains 8-hydroxymethyl-3,5,7,3',4'-penta-O-benzyl-(+)-cyanidan-3-ol; m.p.=96°–97° C.

EXAMPLE 25

A solution of 7.7 g ethyl bromide in 35 ml dry ether is added to a suspension of 2.1 g magnesium in 35 ml dry ether at a rate which allows a slight reflux to be maintained. The mixture is reflux heated for 1 hour and then a solution of 41.3 g 8-formyl-3,5,7,3',4'-penta-O-benzyl-(+)-cyanidan-3-ol in 140 ml dry tetrahydrofuran is added. This is refluxed for another 1 hour and 30 minutes. After cooling, a little water is added then 2N HCl. The two phases are separated and the aqueous phase extracted twice with 50 ml ether. The combined organic phases are dried over magnesium sulphate and the solvents evaporated. The residue is recrystallised twice in a mixture of ethyl alcohol and ethyl acetate. After drying under vacuum, one obtains 8-(1-hydroxy propyl)-3,5,7,3',4'-penta-O-benzyl-(+)-cyanidan-3-ol; m.p.=108°–108.5° C.

EXAMPLE 26

165 g mercuric trifluoracetate is slurried in 20 ml dry methanol and a solution of 1.65 g 8-(but-1-enyl)-3,5,7,3',4'-penta-O-benzyl-(+)-cyanidan-3-ol in 40 ml dry tetrahydrofuran is then added. The resulting mixture is stirred at room temperature for 3 days. Addition of 8 ml of a 3M sodium hydroxyde solution and stirring for 1 hour give rise to the formation of a precipitate of mercury metal. 100 ml of water is added to the separated aqueous phase and the product is extracted with 100 ml methylenedichloride. The organic solution is separated off, washed with 50 ml water, dried with magnesium sulfate and evaporated in vacuo to give a pale-yellow gum. The crude product is purified by column chromatography on silicagel using chloroform as eluant to give 8-(2-methoxybutyl)-3,5,7,3',4'-penta-O-benzyl-(+)-cyanidan-3-ol with a low melting solid (mixture of both diastereoisomers).

EXAMPLE 27

22.1 g potassium t-butylate and 7.5 liters liquid ammonia are placed in a photolytic reactor fitted with a 460 watt medium pressure Hanovia lamp and cooled by a mixture of carbonic anhydride and acetone. The suspension is stirred until the potassium t-butylate is dissolved, then 12 ml absolute acetone and 12 g 8-bromo-3,5,7,3',4'-penta-O-methyl-(+)-cyanidan-3-ol (which remains partially insoluble) are added. This is illuminated and stirred under nitrogen for 3 hours whilst maintaining the temperature at about −30° C. Ammonium chloride is added to the resulting solution then the ammonia is allowed to slowly evaporate off. The residue is then placed in 200 ml dichloromethane, extracted three times with 200 ml water then the combined aqueous phases extracted with 200 ml dichloromethane. The combined organic phases are extracted with 50 ml water, then dried over magnesium sulphate before completely evaporating the solvent. The resulting liquid is purified by passage over a silica gel chromatographic column [eluant: ethyl acetate/petroleum ether (b.p. 60°–80° C.) 1:9], then by recrystallisation in a mixture of ethyl acetate and petroleum ether (b.p. 60°–80° C.). After drying under vacuum, one obtains 8-(2-oxo propyl)-3,5,7,3',4'-penta-O-methyl-(+)-cyanidan-3-ol, in the form of a white solid; m.p.=104°–105° C.

EXAMPLE 28

A solution of 32.0 g 8-(2-carboxyethenyl)-3,5,7,3',4'-penta-O-benzyl-(+)-cyanidan-3-ol in 1,6 liter ethyl acetate is hydrogenated over 16 g palladium 10% on activated charcoal. Hydrogenation lasts 60 hours. After the usual treatment (see example 1), one obtains 8-(2-carboxyethyl)-(+)-cyanidan-3-ol; m.p.=82°–83° C.

EXAMPLE 29

To a 20 g solution of 8-formyl-3,5,7,3',4'-penta-O-methyl-(+)-cyanidan-3-ol in 100 ml dichloromethane is added 100 mg of zinc iodide. After warming at 55° one adds 8.8 ml of trimethylsilyl cyanide. Stirring is maintained one hour. After evaporation, the residue is solubilised in 100 methanol for 20 hours. Evaporation gives a resin which turns out to be unstable for long period storage. Nevertheless, spectroscopic data clearly shows that this resin consist of 8-(1-cyano-1-hydroxymethyl)-3,5,7,3',4'-penta-O-methyl-(+)-cyanidan-3-ol.

EXAMPLE 30

To a stirred solution of 20 g of 8-formyl-3,5,7,3',4'-penta-O-methyl-(+)-cyanidan-3-ol in 100 ml of dichloromethane is added 100 mg of zinc iodide. After warming at 55°, one adds 8.7 ml of trimethylsilylcyanide and stirring is maintained one hour. Solvent is then evaporated and the residue dissolved in 100 ml of absolute tetrahydrofurane. This solution is slowly added to a 10° C. suspension of 3 g lithium aluminium hydride in 50 ml of absolute tetrahydrofurane. After one hour one adds carefully 80 ml of a saturated sodium sulphate solution, and the precipitate is filtrated. After warming the liquid phase is evaporated and the residue is solubilised in 250 ml of methylene chloride. This solution is extracted with 100 ml of a solution 0.5N hydrochloric acid. The water phase is alkalinised with a sodium hydroxide solution and extracted 5 times with dichloromethane. The organic phase is washed with water, dried over magnesium sulphate and evaporated. The residue is recristallised in a mixture of ethyl acetate and diisopropylether to give of 8-(2-amino-1-hydroxyethyl)-3,5,7,3',4'-penta-O-methyl-(+)-cyanidan-3-ol; m.p.: 112°–116° C.

EXAMPLE 31

A solution of 3 g 8-(2-amino-1-hydroxy ethyl)-3,5,7,3',4'-penta-O-methyl-(+)-cyanidan-3-ol and 0.7 g oxalic acid in 250 ml methanol is refluxed for 30 min. After evaporation of the solvent, the residue is suspended in 200 ml refluxing ethyl acetate. After cooling the solid phase is filtered. Recrystallisation in methanol gives hemioxalate of 8-(2-amino-1-hydroxy ethyl)-3,5,7,3',4'-penta-O-methyl-(+)-cyanidan-3-ol as white cristals; m.p.: 184°–186° C.

EXAMPLE 32

As example 31, but using 0.45 ml glacial acetic acid. One obtains the acetate of 8-(2-amino-1-hydroxy ethyl)-3,5,7,3',4'-penta-O-methyl-(+)-cyanidan-3-ol as a white powder; m.p.: 162°–165°.

EXAMPLE 33

As example 31, but starting from 0.89 g of fumaric acid. One obtains the hemifumarate of 8-(2-amino 1-hydroxy ethyl)-3,5,7,3',4'-penta-O-methyl-(+)-cyanidan-3-ol as white cristals; m.p. 185°–187° C.

EXAMPLE 34

As example 30, but starting from 39.6 g of 8-formyl-3,5,7,3',4'-penta-O-benzyl-(+)-cyanidan-3-ol. One obtains 8-(2-amino-1-hydroxy-ethyl)-3,5,7,3',4'-penta-O-benzyl-(+)-cyanidan-3-ol as a resin.

EXAMPLE 35

As example 32, but starting from 5.72 g of 8-(2-amino-1-hydroxy ethyl)-3,5,7,3',4'-penta-O-benzyl-(+)-cyanidan-3-ol. One obtains the corresponding acetate as a white powder; m.p.: 151°–153° C.

EXAMPLE 36

As example 31, but starting from 5.72 g of 8-(2-amino-1-hydroxy ethyl)-3,5,7,3',4'-penta-O-benzyl-(+)-cyanidan-3-ol. One obtains the corresponding hemioxalate as a white powder; m.p.: 152°–155° C.

EXAMPLE 37

As example 33, but starting from 5.72 g of 8-(2-amino-1-hydroxy ethyl)-3,5,7,3',4'-penta-O-benzyl-(+)-cyanidan-3-ol. One obtains the corresponding hemifumarate as a white powder; m.p. 161°–164° C.

EXAMPLE 38

280 ml dimethyl sulphoxide is added to 11 g sodium hydroxide (previously cleared of its oil by successive washing with petroleum ether). After heating to 78° C. for 1 hour, one obtains a 1.63N solution of dimethylsulphoxide anion. 70 ml of this solution is added to a cooled solution of 92.3 g 8-formyl 3,5,7,3',4'-penta-O-benzyl-(+)-cyanidan-3-ol in 550 ml dimethylsulphoxide. After 30 minutes, this is hydrolysed with 500 ml of a saturated solution of ammonium chloride and 2.5 liters water is added. Extraction is carried out with methylene chloride. After washing with water, drying over magnesium sulphate and removal of the solvents, one observes that the residue consists of a mixture of 2 components, which are separated by chromatography on silicagel using a 40/60/1 mixture of n-hexane, ethyl acetate and methyl alcohol as eluant. One isolates 20.7 g (21%) 8-(2-methylsulfinylethenyl)-3,5,7,3',4'-penta-O-benzyl-(+)-cyanidan-3-ol; m.p.=140°–142° C.; and 65.9 g (65%) 8-(1-hydroxy-2-methylsulfinylethenyl)-3,5,7,3',4'-penta-O-benzyl-(+)-cyanidan-3-ol, $[\alpha]_D^{20} = -0,4°$ (0.5% solution in acetone).

EXAMPLE 39

To 1,4 g of dry copper-powder, under a cover of nitrogen, is added 1.69 g trifluoromethyl-mercury$^{II}$ dissolved in 10 ml of N-methyl-2-pyrrolidone. The mixture is heated to 140° C. for 2 hours. Subsequently, 2.16 g 8-iodo-3,5,7,3',4'-penta-O-benzyl-(+)-cyanidan-3-ol in 5 ml N-methyl-2-pyrrolidone is added. The reaction mixture is then heated to 150° C. for 3 hours. After cooling to room temperature, 100 ml of diethylether is added and the mixture is filtered. The solution is washed 4 times with water and dried over magnesium sulfate. Evaporation of the solvent affords a brown oil which is dissolved in chloroform and treated with activated charcoal. The chloroform is then removed and the product is crystallised in diethylether. After drying in vacuo 8-trifluoromethyl-3,5,7,3',4'-penta-O-benzyl-(+)-cyanidan-3-ol is obtained; m.p.: 73°–75° C.

EXAMPLE 40

To a solution of 8.2 g N-N'-methylene-bispiperidine in 20 ml dry ethyl alcohol one adds under nitrogen a solution of 8.9 g 3',4'-O,O-diphenylmethylene-(+)-cyanidan-3-ol in 200 ml dry ethyl alcohol. This is stirred at room temperature for 16 hours and the precipitate formed filtered off and washed in a little ethyl alcohol and dried under vacuum. One obtains 6,8-di-(1-piperidyl methyl)-3',4'-O,O-diphenylmethylene-(+)-cyanidan-3-ol; m.p.=169°–170° C.

EXAMPLE 41

30.8 g 8-formyl-3,5,7,3',4'-penta-O-benzyl-(+)-cyanidan-3-ol and 0.34 g piperidine are added to a solution of 5.0 g malonic acid in 40 ml dry pyridine. This is heated to 100° C., stirring for 2 hours and 30 minutes. After cooling, the solution is poured into a 80 ml mixture of ice and water. After decanting, the oily liquid formed is placed in 200 ml ether and washed in 200 ml hydrochloric acid, then 200 ml water. After drying over magnesium sulphate and evaporation of the solvent, one obtains 8-(2-carboxy ethenyl)-3,5,7,3',4'-penta-O-benzyl-(+)-cyanidan-3-ol; m.p.=64°–65° C.

EXAMPLE 42

A solution of 5.0 g 8-formyl-3,5,7,3',4'-penta-O-benzyl-(+)-cyanidan-3-ol and 1.7 g ethyl bromoacetate in a mixture of 10 ml dry tetrahydrofuran and 20 ml dry benzene is added over a period of 15 minutes to 0.85 g activated zinc. The reaction is initiated by the addition of an iodine crystal, then the mixture is reflux heated for 18 hours.

After cooling to room temperature, 20 ml 5N sulphuric acid is added and the solution stirred vigorously for 30 minutes. The two phases are separated and the organic phase washed in 20 ml water, then 20 ml of saturated sodium bicarbonate solution. After drying over magnesium sulphate and evaporation of the solvents, one obtains 8-(2-ethoxycarbonylethenyl)-3,5,7,3',4'-penta-O-benzyl-(+)-cyanidan-3-ol; m.p.=117°–118° C.

EXAMPLE 43

A solution of 5.0 g 8-formyl-3,5,7,3',4'-penta-O-benzl-(+)-cyanidan-3-ol and 1.4 g 2,2-dimethyl-1,3-dioxane-4,6-dione in 30 ml anhydrous pyridine is heated at 75° C. for 16 hours. After cooling to room temperature, the solution is poured, stirring constantly, into 150 ml ice and water mixture. The water is poured off and the resulting oily liquid dissolved in 20 ml acetone. This solution is poured into 150 ml ice and water mixture and shaken vigorously. The solvent is poured off, then the operation repeated. After drying under vacuum over phosphorous pentoxide, one obtains 8-[(2,2-dimethyl-1,3-dioxane-4,6-dione-5-ylidene)-methyl]-3,5,7,3',4'-penta-O-benzyl-(+)-cyanidan-3-ol in the form of a yellow solid; m.p.=85°–86° C.

EXAMPLE 44

A solution of 12 g 8-(1-hydroxy-2-methylsulphinyl ethyl)-3,5,7,3',4'-penta-O-methyl-(+)-cyanidan-3-ol and 1.2 g anhydrous oxalic acid in 120 ml toluene is heated at 50° C. for 15 hours in the presence of molecular sieves 3 Å. After neutralising with a 7% aqueous solution of sodium bicarbonate, the solution is filtered, washed in water then dried over magnesium sulphate. The residue obtained after concentration is recrystallised in isopropyl ether. In this way, one obtains 8-(2-methylsulphinyl ethenyl)-3,5,7,3',4'-penta-O-methyl-(+)-cyanidan-3-ol; m.p.:148°–151° C.

EXAMPLE 45

A solution of 93.1 g 8-formyl-3,5,7,3',4'-penta-O-methyl (+)-cyanidan-3-ol in 550 dimethyl sulphoxide is cooled to 5° C. and to this is added a 140 ml 1.63N dimethylsulphoxide anion solution prepared in example 38. After 30 minutes, this is hydrolysed with 500 ml ammonium chloride and 2.5 liters water is added. After extraction with methylene chloride, washing of the organic phase in water, drying over magnesium sulphate and concentration, one obtains a residue which is recrystallised in a mixture of isopropyl ether and isopropyl alcohol. In this way a solid white 8-(1-hydroxy-2-methylsulphinyl ethyl)-3,5,7,3',4'-penta-O-methyl-(+)-cyanidan-3-ol is obtained; m.p.=140°–141° C.

EXAMPLE 46

As in example 44, but starting with 12 g 8-(1-hydroxy-2-methylsulphinyl ethyl)-3,5,7,3',4'-penta-O-benzyl-(+)-cyanidan-3-ol. In this way, one obtains 8-(2-methylsulphinyl ethenyl)-3,5,7,3',4'-penta-O-benzyl-(+)-cyanidan-3-ol after crystallisation in ethyl alcohol; Same substance as that in example 38.

EXAMPLE 47

65 g of the crude product obtained in example 45 is dissolved in 250 ml acetic anhydride and then 65 g anhydrous sodium acetate is added. After reflux heating for 2 hours, this is allowed to cool and then filtered on a small dry silicagel column. The acetic anhydride is distilled under vacuum and the residue recrystallised in ethyl alcohol. In this way, one obtains, in the form of white crystals 8-(2-acetoxymethylthio ethenyl)-3,5,7,3',4'-penta-O-methyl-(+)-cyanidan-3-ol that is 81.5% compared to 8-formyl-3,5,7,3',4'-penta-O-methyl-(+)-cyanidan-3-ol; m.p.=103°–106° C.

EXAMPLE 48

As in example 47, but starting with 8 g 8-(2-methylsulphinyl ethenyl)-3,5,7,3',4'-penta-O-methyl-(+)-cyanidan-3-ol. In this way, one obtains 8-(2-acetoxymethylthio ethenyl)-3,5,7,3',4'-penta-O-methyl-(+)-cyanidan-3-ol; Same substance as that in example 47.

EXAMPLE 49

10 g 8-(2-methylsulphinyl ethenyl)-3,5,7,3',4'-penta-O-benzyl-(+)-cyanidan-3-ol, 10 g anhydrous sodium acetate and 40 ml acetic anhydride are reflux mixed for 2 hours. After cooling, the mixture is filtered over a short dry silicagel column and the acetic anhydride distilled under vacuum. The residue is recrystallised in a mixture of hexane and toluene. In this way one obtains 8-(2-acetoxymethylthio ethenyl)-3,5,7,3',4'-penta-O-benzyl-(+)-cyanidan-3-ol; m.p.=125°–126° C.

EXAMPLE 50

As example 49, but starting with 53 g of the crude mixture obtained in example 38. In this way, one obtains 8-(2-acetoxymethylthio ethenyl)-3,5,7,3',4'-penta-O-benzyl-(+)-cyanidan-3-ol; same substance as that in example 49.

EXAMPLE 51

As example 49, but starting with 10 g 8-(1-hydroxy-2-methylsulfinylethyl)-3,5,7,3',4'-penta-O-benzyl-(+)-cyanidan-3-ol. In this way, one obtains 8-(2-acetoxymethylthio ethenyl)-3,5,7,3',4'-penta-O-benzyl-(+)-cyanidan-3-ol; same substance as in example 49.

EXAMPLE 52

20.0 g 8-(2-nitroethenyl)-3,5,7,3',4'-penta-O-benzyl-(+)-cyanidan-3-ol is dissolved in 250 ml ethylacetate and 10 g 5% palladium on activated charcoal is added. The stirred mixture is hydrogenated for 18 hours. After this time, the catalyst is filtered off and the solvent evaporated in vacuo. The residue is purified by column chromatography on silicagel. Elution with benzene/diethylether (3:2) gives 8-(2-nitroethenyl)-3-O-benzyl-(+)-cyanican-3-ol as a white solid; m.p.: 47–49° C.

EXAMPLE 53

59 g 8-formyl-3,5,7,3',4'-penta-O-benzyl-(+)-cyanidan-3-ol is dissolved in a mixture of 500 ml dry pyridine and 12.8 g piperidine. 12.0 g nitromethane is slowly added with constant stirring and the mixture then heated at 65° C. for 3 hours. After cooling, the solvents are evaporated off under vacuum and the residue placed in 400 ml dichloromethane. The solution is washed with 200 ml 2N hydrochloric acid, then twice with 200 ml water. The solution is dried over magnesium sulphate, evaporated under vacuum and the residue recrystallised in a mixture of ethyl alcohol and ethyl acetate. After drying under vacuum, one obtains 8-(2-nitro ethenyl)-3,5,7,3',4'-penta-O-benzyl-(+)-cyanidan-3-ol; m.p.: 153°-154° C.

EXAMPLE 54

As in example 22, but adding 10.7 g 4-bromofluorobenzene and using diethyl ether for extracting the aqueous layer. Hydrogenation is carried out in 400 ml of ethyl alcohol at 70° C. during 2 hours and half, then at 25° C. during 72 hours. After filtrating the catalyst and evaporating the solvent, the residue is purified by elution through a silicagel Merck 60 column with a mixture of ethyl acetate and chloroform, then by crystallisation of the interesting fractions in a mixture of ethyl alcohol and water. 8-(4-fluorobenzyl)-(+)-cyanidan-3-ol is obtained; m.p. 200°-201° C.

EXAMPLE 55

A suspension of 1.85 g magnesium in 50 ml anhydrous tetrahydrofuran is prepared under strictly anhydrous conditions and nitrogen. 14 g freshly distilled 4-bromofluorobenzene is then added drop by drop and an iodine crystal is added. After one hour reflux heating, when most of magnesium has reacted, a solution of 19.4 g 8-formyl-3,5,7,3',4'-penta-O-methyl-(+)-cyanidan-3-ol in 450 ml dry tetrahydrofuran is introduced into the reactor. Reflux heating is maintained for one more hour and after cooling 50 ml of water and 50 ml of 2N hydrochloric acid are slowly added. The organic layer is separated and the aqueous layer is extracted with ethyl acetate. The organic solutions are combined, dried over magnesium sulphate and the solvent evaporated. The residue is dissolved in 300 ml ethyl acetate and hydrogenated over 10% palladium on activated charcoal. After filtrating the catalyst and evaporating the solvent, the residual compound is dissolved in a mixture of methanol and ethyl acetate, from which crystallised 8-(4-fluorobenzyl)-3,5,7,3',4'-penta-O-methyl-(+)-cyanidan-3-ol; m.p. 144° C.

EXAMPLE 56

As in example 55, but adding 13.7 g 4-bromotoluene. The resulting compound is crystallised in a mixture of ethanol and water; 8-(4-methylbenzyl)-3,5,7,3',4'-penta-O-methyl-(+)-cyanidan-3-ol is obtained; m.p.: 97°-98° C.

EXAMPLE 57

As in example 14, but using 5 g bromo-2-benzyl bromide and stirring at 95° C. for 6 hours. 6,8-di-(2-bromo benzyl)-(+)-cyanidan-3-ol is obtained; m.p.: 120° C.

EXAMPLE 58

As in example 22, but adding 11.4 g 4-bromoanisole and hydrogenating in a mixture of methanol and ethyl acetate plus 0.5% formic acid. After crystallising in a mixture of ethanol and water 8-(4-methoxybenzyl)-(+)-cyanidan-3-ol is obtained; m.p.: 188°-189° C.

EXAMPLE 59

As in example 55, but adding 15 g 4-bromomethoxybenzene. The resulting compound is crystallised in methanol and 8-(4-methoxy-benzyl)-3,5,7,3',4'-penta-O-methyl-(+)-cyanidan-3-ol is obtained; m.p. 95°-96° C.

EXAMPLE 60

As in example 55, but adding 16 g 4-bromo-N,N-dimethylaniline. Hydrogenation is carried out in methanol containing 0,2% formic acid over 10% palladium on activated charcoal. After filtration of the catalyst and evaporation of the solvent, the resulting compound is crystallised in methanol and 8-(4-N,N-dimethylaminobenzyl)-3,5,7,3',4'-penta-O-methyl-(+)-cyanidan-3-ol is obtained; m.p.: 101° C.

EXAMPLE 61

As in example 14, but using 5.4 g 4-nitrobenzyl bromide and stirring at 95° C. for 4 hours. 6,8-di-(4-nitrobenzyl)-(+)-cyanidan-3-ol is obtained; m.p.: 136°-137° C.

EXAMPLE 62

To a solution of 5.8 g N,N'-benzylidin-bispiperidine in 40 ml dry ethyl alcohol, is added stirring vigorously under nitrogen, a solution of 4.45 g 3',4'-O,O-diphenylmethylene (+)-cyanidan-3-ol in 70 ml dry ethyl alcohol. The mixture is reflux heated for 1 hour 30 minutes, cooled to 0° C. and the solid which forms, filtered off. After recrystallisation of the precipitate in ethyl alcohol and drying under vacuum, one obtains 6,8-di[phenyl-(1-piperidyl-methyl)]-3',4'-O,O-diphenylmethylene-(+)-cyanidan-3-ol; m.p.=160°-161° C.

EXAMPLE 63

100 mg xenon fluoride is added to a solution of 213 mg 3,5,7,3',4'-penta-O-methyl-(+)-cyanidan-3-ol in 2 ml dichloromethane containing anhydrous sodium sulfate and previously freezed to −196° C. under high vacuum (2,5.10$^{-2}$ mm Hg). After tightly stopping the vessel the temperature is allowed to rise slowly to 0° C. and maintained at this level for 15 minutes. The solvent and hydrogen fluoride evolved during the reaction are evaporated by gently heating under vacuum. Chloroform is added to the residue, the suspension filtered and the filtrate evaporated to dryness. The crude mass contains 24% of the waited compound which is isolated by elution through a Woelm A III dry silicagel column; 8-fluoro-3,5,7,3',4'-penta-O-methyl-(+)-cyanidan-3-ol is obtained; m.p.: 166°-168° C.

EXAMPLE 64

3.4 ml of a 1.47M n-butyl lithium solution in n-hexane is added slowly under nitrogen at −70° C. to a solution of 4.1 g 8-bromo-3,5,7,3',4'-penta-O-benzyl-(+)-cyanidan-3-ol in 40 ml tetrahydrofuran. After 30 minutes this solution is added to a solution of 2 g perchloryl fluoride in 40 ml tetrahydrofuran at −70° C. The mixture is stirred for 1 hour at −70° C., for 2 hours at a temperature between −30° C. and −40° C. and then for 1 hour at room temperature. After removal of the gas under vacuum, the mixture is placed in 300 ml water. Extraction is carried out with toluene, the organic phase is washed with water, dried over magnesium sulphate and the solvent evaporated. The product is purified by chromatography on a silicagel column (eluant=toluene), then by recrystallisation in cyclohexane, 8-fluoro- 3,5,7,3',4'-penta-O-benzyl-(+)-cyanidan-3-ol is obtained; m.p.=96°–98° C.

EXAMPLE 65

12.7 g 2,4,4,6-tetrabromo-2,5-cyclohexadiene-1-one is added to a solution of 20 g 3,5,7,3',4'-pentakis-O-trimethylsilyl-(+)-cyanidan-3-ol in 310 ml carbon tetrachloride. After 2 hours the solvent is evaporated. The residue is treated with 300 ml methyl alcohol 80% under reflux for 5 hours. The solvent is evaporated and residue freeze-dried. The product obtained is purified by extraction with dichloromethane in a soxhlet and the remaining solid by chromatography on a Sephadex $LH_{20}$ column (eluant: methyl alcohol 65%). In this way one obtains 8-bromo-(+)-cyanidan-3-ol; m.p.=150° C.; $[\alpha]_D^{20} = -81.0°$; (C=0.5 in EtOH 95%).

EXAMPLE 66

20 g (+)-cyanidan-3-ol is dissolved in 700 ml ethyl acetate under reflux. The solution is cooled down and 57 g 2,4,4,6-tetrabromo-2,5-cyclohexadiene-1-one are added. After 3 hours at room temperature, this is then evaporated at low temperature and the residue is extracted by means of methylene chloride in a soxhlet overnight. From this, one obtains 29 g of a solid which contains 91%, 6,8-dibromo-(+)-cyanidan-3-ol which is then purified to 99% by chromatography on a Sephadex $LH_{20}$ column (65% methyl alcohol as eluant); m.p.: 195° C.

EXAMPLE 67

50 g dioxane is treated with 99 g bromine. The solution is poured into 200 ml water and the precipitate removed and dried. 20.8 g of this bromine-dioxane complex is added by small portions to a solution of 46.5 g 3-O-methyl-5,7,3',4'-tetra-O-benzyl-(+)-cyanidan-3-ol in 1 liter methylene chloride at −20° C. The temperature is allowed to rise to −5° C. and the solution is washed with a 5% sodium bisulphite solution. This is then neutralised with a 5% sodium bicarbonate solution, then with water and dried over magnesium sulphate. The residue obtained after evaporation is crystallised twice in a mixture of acetone and hexane. In this way 8-bromo-3-O-methyl-5,7,3',4'-tetra-O-benzyl-(+)-cyanidan-3-ol is obtained; m.p.: 120° C.

EXAMPLE 68

Over a period of one hour, a solution of 22.7 g bromine in 500 ml dichloromethane is added to a solution of 100 g 3,5,7,3',4'-penta-O-benzyl-(+)-cyanidan-3-ol in one liter of dichloromethane at −10° C., while stirring under nitrogen. The temperature is then allowed to rise so that it reaches 5° C. after 2 hours, then washed with an aqueous solution of 5% sodium bicarbonate is carried out. This is dried on magnesium sulphate and the solvent evaporated under vacuum. The residue is crystallised once in a mixture of ethyl acetate and ethyl alcohol. In this way 8-bromo-3,5,7,3',4'-penta-O-benzyl (+)-cyanidan-3-ol is obtained; m.p.: 110°–111° C.

EXAMPLE 69

1.5 bromine dioxane (prepared as in example 67) is gradually added at −30° C. to a solution of 3.7 g 3,5,7,3',4'-penta-O-benzyl-(+)-cyanidan-3-ol in 75 ml methylene chloride.

30 minutes later the temperature is allowed to reach +5° C. and it is washed with a 5% solution of sodium bisulphite then with a solution of 5% sodium bicarbonate and finally with water. Drying is carried out over magnesium sulphate. After evaporation of the solvent a resin is obtained. This is recrystallised twice in a mixture of acetone and hexane. A yield of 3.2 g (78%) 8-bromo 3,5,7,3',4'-penta-O-benzyl-(+)-cyanidan-3-ol is obtained; same substance as that in example 68.

EXAMPLE 70

A solution of 100 g 3,5,7,3',4'-penta-O-benzyl-(+)-cyanidan-3-ol and 21 g 1,3-dibromo-5,5-dimethylhydantoin in 1 liter of acetone is stirred for 3½ days at room temperature. The solvent is then evaporated under vacuum and the resulting oil dissolved in 1 liter dichloromethane. The solution is washed with a 5% aqueous solution of sodium bisulphite, with a 5% aqueous solution of sodium bicarbonate and with water, then dried and the solvent evaporated under vacuum. The solid residue is then crystallised once in a mixture of ethyl acetate and ethyl alcohol. This produces the 8-bromo-3,5,7,3',4'-penta-O-benzyl (+)-cyanidan-3-ol; same substance as in example 68.

EXAMPLE 71

7.4 g 3,5,7,3',4'-penta-O-benzyl-(+)-cyanidan-3-ol is dissolved in 150 ml carbon tetrachloride, the solution is cooled to 0° C. and over a period of 25 minutes 65 ml of a solution containing 3.3 g bromine in carbon tetrachloride is added. This is stirred for 15 minutes, then washed successively with 50 ml of a 5% sodium bisulphite solution in water and 50 ml of a 5% sodium bicarbonate solution in water, then finally twice with 50 ml water. The lwoer phase is dried over magnesium sulphate, decanted and the carbon tetrachloride evaporated off. The solid residue is crystallised twice from a mixture of chloroform-hexane and this produces 6,8-dibromo-3,5,7,3',4'-penta-O-benzyl-(+)-cyanidan-3-ol; m.p.: 133°–135° C.

EXAMPLE 72

To a solution of 21.3 g 3,5,7,3',4'-penta-O-benzyl-(+)-cyanidan-3-ol in 32 ml dichloromethane and 4 ml ethyl alcohol are added 7.9 g iodine and 6.24 g yellow mercuric oxide in small quantities alternatively and over a period of 30 minutes. The solution is then stirred at room temperature for 2 hours 30 minutes. This is then filtered and the precipitate washed with 80 ml dichloromethane. The filtrate and the dichloromethane extract are combined and then washed 3 times with an aqueous solution of sodium iodide. After drying over magnesium sulphate, the solvent is evaporated off and the residue recrystallised in a mixture of acetone and petroleum ether (p.e. 60°–80° C.). In this way 8-iodo-3,5,7,3',4'-penta-O-benzyl-(+)-cyanidan-3-ol are obtained; m.p. 115°–117° C.

EXAMPLE 73

15.1 g thallium$^{III}$ trifluoro acetate is added to a solution of 20.6 g 3,5,7,3',4'-penta-O-benzyl-(+)-cyanidan-3-ol in 90 ml acetonitrile. This is stirred for 20 hours at room temperature, then 10.7 g potassium iodide dissolved in 100 ml water is slowly added. After stirring for 2 hours, 12.5 g sodium metabisulphite in 50 ml water is added and the mixture is stirred for 45 min. more. The solution is alkalinised by the addition of an aqaueous 4N sodium hydroxide, then the precipitate filtered off. After adding 300 ml ether to the filtrate, this is stirred for 2 hours, then the precipitate filtered off. The two phases of the filtrate are separated and the aqueous phase is extracted twice with ether. The organic phases are combined and dried over magnesium sulphate before evaporating off the solvent. The product is purified by chromatography on a silica gel column (eluent=chloroform), then by recrystallisation in a mixture of acetone and petroleum ether. A yield of 8-iodo-3,5,7,3',4'-penta-O-benzyl-(+)-cyanidan-3-ol is obtained; m.p.: 115°–117° C.

EXAMPLE 74

10 g 8-formyl-3,5,7,3',4'-penta-O-benzyl-(+)-cyanidan-3-ol is dissolved in a mixture of 100 ml ethyl acetate and 50 ml toluene, then hydrogenated at room temperature during one and half hour with 2 g palladium 5% on activated charcoal. The catalyst is filtered off, the solvent evaporated and the residue is crystallised in a mixture of methanol and water (25:75 v/v). 8-formyl-(+)-cyanidan-3-ol is obtained; m.p.: 229°–231° C.

EXAMPLE 75

A solution of 4.0 g 8-formyl-3-O-methyl-5,7,3',4'-tetra-O-benzyl-(+)-cyanidan-3-ol in 350 ml anhydrous ethyl acetate is hydrogenated over 2.0 g 5% palladium on active charcoal. Hydrogenation lasts 19 hours. After usual treatment (see example 1) one obtains 8-formyl-3-O-methyl-(+)-cyanidan-3-ol; m.p.: 201°–202° C.

EXAMPLE 76

A solution of 40.0 g 8-formyl-3-O-n-butyl-5,7,3',4'-tetra-O-benzyl-(+)-cyanidan-3-ol in 800 ml ethyl acetate is hydrogenated over 20 g 5% palladium on activated charcoal. Hydrogenation lasts for 6 hours. After usual treatment, (see example 1), one obtains 8-formyl-3-O-butyl-(+)-cyanidan-3-ol; m.p.: 79°–80° C.

EXAMPLE 77

A solution of 1.0 g 8-formyl-3-O-palmitoyl-5,7,3',4'-tetra-O-benzyl-(+)-cyanidan-3-ol in 100 ml ethyl acetate is hydrogenated over 0.5 g 10% palladium on activated charcoal. After absorption of 4 hydrogen equivalents (7 hours) the catalyst is filtered and evaporated. The yellow oily liquid obtained is twice mixed in water and freeze-dried. After vacuum drying over phosphorus pentoxide, one obtains 8-formyl-3-O-palmitoyl-(+)-cyanidan-3-ol in the form of a pale, yellow solid; m.p.: 57°–58° C.

EXAMPLE 78

29.6 g 3,5,7,3',4'-penta-O-benzyl-(+)-cyanidan-3-ol is dissolved in 40 ml dry dimethylformamide. After cooling to 10°–12° C., 6.4 g phosphorus oxychloride is added slowly. The reaction is exothermic and temperature is kept below 15° C. by means of a freezing bath. After stirring for one hour at room temperature, 100 ml water is added. The oily precipitate is separated by decanting and placed in 200 ml methylene chloride. The organic phase is neutralised with a saturated solution of sodium bicarbonate then washed with water and dried over magnesium sulphate. After evaporation and drying under vacuum at 35° C. a solid brown mass is obtained. This moss is cristallized from a mixture of toluene-n-hexane to give 8-formyl-3,5,7,3',4'-penta-O-benzyl-(+)-cyanidan-3-ol; m.p.: 98°–99° C.

EXAMPLE 79

As in example 78, but starting with 28, 24 g 3-O-butyl-5,7,3',4'-tetra-O-benzyl-(+)-cyanidan-3-ol, one obtains 8-formyl-3-O-butyl-5,7,3',4'-tetra-O-benzyl-(+)-cyanidan-3-ol in the form of a solid brown resin.

EXAMPLE 80

As example 78, but starting with 27.1 g 5,7,3',4'-tetra-O-benzyl-(+)-cyanidan-3-ol and 12.8 g phosphorous oxychloride. One obtains 8-formyl-3-O-formyl-5,7,3',4'-tetra-O-benzyl-(+)-cyanidan-3-ol in the form of white crystals after recrystallisation in a mixture of ethyl alcohol and ethyl acetate; m.p.: 145.5° C.

EXAMPLE 81

As in example 78, but starting with 32.52 g 3-O-palmitoyl-5,7,3',4'-tetra-O-benzyl-(+)-cyanidan-3-ol, one obtains 8-formyl-3-O-palmitoyl-5,7,3',4'-tetra-O-benzyl-(+)-cyanidan-3-ol in the form of a yellow-brown solid; m.p.: 65.5°–67° C.

EXAMPLE 82

As in example 78, but starting with 30.8 g 3,O-phenylcarbamoyl-5,7,3',4'-tetra-O-benzyl-(+)-cyanidan-3-ol, one obtains 8-formyl-3-O-phenylcarbamoyl-5,7,3',4'-tetra-O-benzyl-(+)-cyanidan-3-ol in the form of a white solid; m.p.: 159°–160° C.

EXAMPLE 83

A solution of 32 g 3,5,7,3',4'-penta-O-methyl-(+)-cyanidan-3-ol in 72 ml dimethylformamide is treated with 9.7 ml phosphorous oxychloride. The temperature is kept at 10°–15° C. by means of an ice bath and controled rate of addition. After 15 minutes the solution is stirred at room temperature for an hour. The flask is cooled down again with an ice bath and 250 ml of an aqueous saturated solution of sodium acetate is slowly added. This produces a white precipitate in a few minutes. After one hour, 200 ml methylene chloride is added. After separating the two phases, the aqueous phase is twice extracted with 50 ml methylene chloride. The organic phases are recombined, washed twice with a saturated sodium chloride solution, neutralised with a 10% aqueous solution of sodium bicarbonate, then washed again with a saturated sodium chloride solution. After drying over magnesium sulphate, filtering and evaporation, a solid, white residue is obtained. This is recrystallised in a mixture of ethyl alcohol and cyclohexane. In this way, one obtains 8-formyl-3,5,7,3',4'-penta-O-methyl-(+)-cyanidan-3-ol in the form of white crystals: m.p.: 147.5°–148° C.

EXAMPLE 84

As in example 78, but starting with 26.6 g 3-O-methyl-5,7,3',4'-tetra-O-benzyl-(+)-cyanidan-3-ol; one obtains 8-formyl-3-O-methyl-5,7,3',4'-tetra-O-benzyl-(+)-cyanidan-3-ol in the form of a yellowish solid.

EXAMPLE 85

3 ml dimethylformamide is treated, under nitrogen and after cooling with 2.5 ml thionyl chloride. After 30 minutes this is placed under vacuum (40°, 18 mm Hg) to remove the sulphur dioxide formed. 10 ml dimethyl formamide is added to the white solid obtained and then a solution of 3,5,7,3',4'-penta-O-methyl-(+)-cyanidan-3-ol in 20 ml dimethylformamide. After 1 hour this is evaporated under low vacuum (0.1 mm Hg) and the remaining solid is placed in 100 ml anhydrous tetrahydrofuran. This is filtered and then rinsed three times with 20 ml tetrahydrofuran. After drying over phosphorous pentoxide, one obtains of an amorphous pink powder. This is 8-N,N-dimethyl-iminomethyl-3,5,7,3',4'-penta-O-methyl-(+)-cyanidan-3-ol; m.p.=190°-191° C.

EXAMPLE 86

20.0 g of 8-[N-(isopropyl)-iminomethyl]-3,5,7,3',4'-penta-O-benzyl-(+)-cyanidan-3-ol is slurried with 40 ml of ethyl acetate and a catalyst mixture of 10 g of 5% palladium on carbon and 4 g of 5% platinum on active charcoal is added. The resulting mixture is stirred for 5 hours after which the catalyst is filtered and the filtrate evaporated in vacuo. The crude residue is purified by column chromatography on silicagel using benzene/diethylether (2:1) as eluant to give 8-N-isopropylaminomethyl-(+)-cyanidan-3-ol; m.p.: 95°-98° C.

Further gradient elution of the silicagel column using benzene/diethylether (1:1) and then benzene/diethylether (1:2) gives 8-(N-isopropyl-iminomethyl)-3-O-benzyl-(+)-cyanidan-3-ol; m.p.: 118°-122° C.

EXAMPLE 87

A solution of 19.0 g 8-formyl-3,5,7,3',4'-penta-O-benzyl-(+)-cyanidan-3-ol in 75 ml isopropylamine is stirred for 17 hours. 500 ml water is added, the precipitate filtered off dried under vacuum, then recrystallised in ethyl alcohol. After drying under vacuum, one obtains 8-(N-isopropyliminomethyl)-3,5,7,3',4'-penta-O-benzyl-(+)-cyanidan-3-ol; m.p. 106°-107° C.

EXAMPLE 88

7.7 g 8-formyl-3,5,7,3',4'-penta-O-benzyl-(+)-cyanidan-3-ol, 15 ml aniline and 10 mg p-toluenesulfonic acid are dissolved in 80 ml of toluene. The solution is reflux heated for a period of 17 hours during which time water is removed by azeotropic distillation using a Dean and Stark tube. After this time, the solution is cooled to room temperature and then washed with 2 times 40 ml 2N hydrochloric acid, 40 ml water, 40 ml of a saturated sodium bicarbonate solution and 40 ml water. Drying with magnesium sulfate and evaporation give a solid residue which is crystallized twice from ethyl acetate. 8-(N-phenyliminomethyl)-3,5,7,3',4'-penta-O-benzyl-(+)-cyanidan-3-ol is obtained as a bright yellow solid; m.p.: 145°-146° C.

EXAMPLE 89

A solution of 7.7 g 8-formyl-3,5,7,3',4'-penta-O-benzyl-(+)-cyanidan-3-ol, 2.8 g 4-nitroaniline and 10 mg p-toluenesulfonic acid in 80 ml toluene is heated at reflux temperature for 16 hours. During this time, water is removed by azeotropic distillation using a Dean and Stark tube. The solution is then cooled to room temperature and washed with 2×40 ml of 2N-hydrochloric acid, 40 ml of water, 40 ml of a saturated sodium bicarbonate solution and 40 ml of water. Drying with magnesium sulfate and evaporation give 8-(N-4-nitrophenyliminomethyl)-3,5,7,3'4'-penta-O-benzyl-(+)-cyanidan-3-ol as an oil; $[\alpha]_D^{20} = -32°$ (C=1 in chloroform).

EXAMPLE 90

A solution of 400 g 8-hydroxyiminomethyl-3,5,7,3',4'-penta-O-benzyl-(+-cyanidan-3-ol and 3.2 g glacial acetic acid in a mixture of 3.6 liters ethyl acetate and 400 ml ethyl alcohol is hydrogenated over 20 g palladium 5% on activated charcoal. Hydrogenation lasts for 24 hours. After the usual treatment (see example 1), one obtains 8-hydroxyiminomethyl-(+)-cyanidan-3-ol; m.p.: 163°-164° C.

EXAMPLE 91

A solution of 41.3 g 8-formyl-3,5,7,3',4'-penta-O-bemzyl-(+)-cyanidan-3-ol and 7.7 g hydroxylamine hydrochloride in 175 ml anhydrous pyridine is heated at 80° C. for 3 hours. After cooling, the pyridine is evaporated, the residue dissolved in 300 ml dichloromethane, washed with 150 ml 2N hydrochloric acid and 100 ml water. After drying over magnesium sulphate and evaporation of the solvent, the solid is recrystallised in a mixture of ethyl alcohol and ethyl acetate; after drying under vacuum, one obtains 36.7 g (87%) 8-hydroxyiminomethyl-3,5,7,3',4'-penta-O-benzyl-(+)-cyanidan-3-ol; m.p.: 133°-134° C.

EXAMPLE 92

A mixture of 5.0 g 8-hydroxyiminomethyl-3,5,7,3',4'-penta-O-benzyl-(+)-cyanidan-3-ol and 150 ml acetic anhydride is heated at 50° C. for 10 minutes with stirring. The resulting solution is slowly poured whilst stirring into 100 ml ice and water mixture. Stirring is continued for 30 minutes, the solid formed is filtered off and washed in water. After drying under vacuum, one obtains 8-acetoxyiminomethyl-3,5,7,3',4'-penta-O-benzyl-(+)-cyanidan-3-ol; m.p.: 107°-108° C.

EXAMPLE 93

A solution of 1.0 g 8-carboxy-3,5,7,3',4'-penta-O-benzyl-(+)-cyanidan-3-ol in 50 ml of ethyl acetate is flushed with nitrogen. 0.5 g of 5% palladium on active charcoal is added, the suspension is stirred and hydrogen is bubbled through the mixture. The reaction is complete after 4 hours. The catalyst is filtered off and the solution evaporated in vacuo to give initially an oil. After 18 hours under high vacuum, the oil solidifies to give 8-carboxy-(+)-cyanidan-3-ol as a white solid. The compound decomposes without melting at 200° C.

EXAMPLE 94

A solution of 6 g 8-carboxy-3-O-methyl-5,7,3',4'-tetra-O-benzyl-(+)-cyanidan-3-ol in 600 ml ethyl acetate is hydrogenated at room temperature over 3 g palladium 10% on activated charcoal. Hydrogenation lasts for 2 hours. After usual treatment (cf. example 1), amorphous, white, solid 8-carboxy-3-O-methyl-(+)-cyanidan-3-ol is isolated; $[\alpha]_D^{20} = -51.8°$ (C=0.5 in ethanol)).

EXAMPLE 95

A solution of 2.0 g 8-carboxy-3,5,7,3',4'-penta-O-benzyl-(+)-cyanidan-3-ol in 200 ml of ethyl acetate is flushed with nitrogen, 0.5 og 5% palladium on activated charcoal is added. The suspension is stirred and hydrogen is bubbled through the mixture for 1½ hour. The catalyst is filtered off and the solution evaporated in vacuo to give an oil. The crude product is purified by column chromatography on silicagel using benzene/diethylether (3:2) as eluant to give 8-carboxy-3-O-benzyl-(+)-cyanidan-3-ol as a white solid; m.p.: 147°-149° C.

EXAMPLE 96

37.2 g 8-bromo-3-O-methyl-5,7,3',4'-tetra-O-benzyl-(+)-cyanidan-3-ol is dissolved in 400 ml anhydrous tetrahydrofuran in a 1 liter reaction flask A. After cooling to −70° C., 34 ml of a 1.47M solution of n-butyl lithium in n-hexane is added. A second reaction flask B is connected to A by means of a tube allowing flow control. Reaction flask B contains a saturated solution of carbon dioxide in 500 ml dry tetrahydrofuran obtained by bubbling at −70° C. for 3 hours. The solution in flask A is allowed to enter at a rate which enables temperature to be maintained at approximately −70° C. After 2 hours, the mixture is allowed to heat up to 0° C. and is then hydrolysed with 100 ml 0.5N aqueous hydrochloric acid. The tetrahydrofuran is evaporated off and 350 ml dichloromethane is added. The solution obtained is washed with water, dried over magnesium sulphate then completely evaporated. The resulting residue is crystallised in methyl alcohol and recrystallised in a mixture of methyl alcohol and chloroform. In this way 8-carboxy-3-O-methyl-5,7,3',4'-tetra-O-benzyl-(+)-cyanidan-3-ol in the form of white crystals is obtained; m.p.: 142° C.

EXAMPLE 97

41 g 8-bromo-3,5,7,3',4'-penta-O-benzyl-(+)-cyanidan-3-ol is dissolved in 400 ml anhydrous tetrahydrofuran in a 1 liter flask A. After cooling to −70° C. 34 ml of a 1.47M solution of n-butyl-lithium in n-hexane is added. A second flask B is connected to flask A by a tube allowing controlled flow. Flask B contains a solution of 7.14 g dry phenyl isocyanate in 20 ml anhydrous tetrahydrofuran. After cooling down flask B to −70° C., the solution from flask A is gradually added so that the temperature is kept at about −70° C. Afterwards the temperature of the mixture is allowed to rise to room temperature and is hydrolysed with 5 ml water. The tetrahydrofuran is evaporated off and then 350 ml dichloromethane is added. The solution obtained is washed in water, dried over magnesium sulphate then completely evaporated. The residue is crystallised in a mixture of methyl alcohol and ethyl acetate. One obtains 8-N-phenylcarboxamido-3,5,7,3',4'-penta-O-benzyl-(+)-cyanidan-3-ol in the form of a white powder; m.p.: 185°–186° C.

EXAMPLE 98

A solution of 8 g 8-methoxycarbonyl-3,5,7,3',4'-penta-O-benzyl-(+)-cyanidan-3-ol in 300 ml ethyl acetate is hydrogenated at atmospheric pressure in the presence of 2.7 g palladium 10% on activated charcoal. After 24 hours the suspension is filtered in cellite and the filtrate completely evaporated under vacuum at 30° C. The residue is dissolved in a mixture of ethyl alcohol and water and slowly evaporated under vacuum until a heavy precipitate is obtained. This operation is repeated and the precipitate dried. In this way, one obtains 8-methoxycarbonyl-(+)-cyanidan-3-ol; m.p.: 208°–210° C.

EXAMPLE 99

As in example 97, but the reactor B contains 9.45 g methyl chloroformiate in 65 ml tetrahydrofuran. As the residue cannot be crystallised, it is purified by elution on a dry silicagel column with dichloromethane. One obtains 8-methoxycarbonyl-3,5,7,3',4'-penta-O-benzyl-(+)-cyanidan-3-ol; m.p.: 53°–54° C.

EXAMPLE 100

A solution of 4 g 8-ethoxycarbonyl-3,5,7,3',4'-penta-O-benzyl-(+)-cyanidan-3-ol in 300 ml of a mixture of 4 parts to 1 of ethyl alcohol and ethyl acetate is hydrogenated over 2 g palladium 10% on activated charcoal. Hydrogenation lasts for 2 hours. After usual treatment (cf. example 1) solid white 8-ethoxycarbonyl-(+)-cyanidan-3-ol is isolated; m.p.: 197°–198° C.

EXAMPLE 101

As in example 97, but reactor B contains a solution of 5.45 g ethyl chloroformiate in 50 ml tetrahydrofuran. The residue obtained is purified by dry column chromatography on silicagel. First elution is carried out using toluene, then ethyl acetate to obtain 8-ethoxycarbonyl-3,5,7,3',4'-penta-O-benzyl-(+)-cyanidan-3-ol.

EXAMPLE 102

18.2 g thionyl chloride is added while stirring at 0°–5° C. to a solution of 60.0 g 8-carboxy 3,5,7,3',4'-penta-O-benzyl-(+)-cyanidan-3-ol and 15.5 g triethylamine in 250 ml dichloromethane. Two hours later 9.0 g isopropylamine are slowly added and the solution allowed to warm to room temperature. This is stirred for 16 hours, then washed with 250 ml water, 250 ml saturated sodium bicarbonate solution and 250 ml water. After drying over magnesium sulphate, the solvent is evaporated off and the residue crystallised in a mixture of ethyl alcohol and ethyl acetate. The product is dried under vacuum and one obtains 46.3 g (73%) 8-(N-isopropylcarboxamido)-3,5,7,3',4'-penta-O-benzyl-(+)-cyanidan-3-ol; m.p.: 177°–178° C.

EXAMPLE 103

100 mg thionyl chloride is added whilst stirring at 0°–5° C. to a solution of 500 mg 8-carboxy 3,5,7,3',4'-penta-O-benzyl (+)-cyanidan-3-ol and 160 mg triethylamine in 3 ml dichloromethane. After 10 minutes, 100 mg n-butylamine is added and reflux heated for 3 hours. This is allowed to cool down to room temperature, washed in 3 ml water, dried over magnesium sulphate and the solvent completely evaporated. After recrystallisation of the residue in a mixture of ethyl acetate and ethyl alcohol, one obtains 8-[N(1-butyl)carboxamido]-3,5,7,3',4'-penta-O-benzyl-(+)-cyanidan-3-ol; m.p.: 173°–175° C.

EXAMPLE 104

A solution of 31.3 g 8-N-phenylcarboxamido-3,5,7,3',4'-penta-O-benzyl-(+)-cyanidan-3-ol in 600 ml ethyl acetate is hydrogenated at ordinary temperature over 15 g palladium 10% on activated charcoal. The process lasts 4 hours. After the usual treatment (cf. example 1) 8-N-phenylcarboxamido-(+)-cyanidan-3-ol is isolated; m.p.: 234°–235° C.

EXAMPLE 105

As in example 97, but the reactor B contains a saturated solution of carbon dioxide in 2 liter dry tetrahydrofuran. Carbon dioxide gas is bubbled into reactor B during introduction of the solution of reactor A and for 1 hour afterwards. After warming up reactor B to room temperature, a solution of 75 Ml, 0.5M hydrochloric acid and 600 ml water is added. This is stirred for 30 minutes, the tetrahydrofuran is evaporated off under vacuum, then extraction with 1.5 l dichloromethane is carried out. After drying over magnesium sulphate, the solvent is evaporated off under vacuum. The residue is crystallised in a mixture of chloroform and methyl alcohol, then re-crystallised in a mixture of carbon tetrachloride and methyl alcohol. After drying under vacuum, one obtains 8-carboxy-3,5,7,3',4'-penta-O-benzyl-(+)-cyanidan-3-ol; m.p.=132°–133° C.

EXAMPLE 106

100 mg thionyl chloride is added while stirring at 0°–5° C., to a solution of 400 mg 8-carboxy-3,5,7,3',4'-penta-O-benzyl-(+)-cyanidan-3-ol and 160 mg triethylamine in 5 ml dichloromethane. After 10 minutes, 100 mg N,N-diethylethylenediamine is added, the mixture stirred for 1 hour, then reflux heated for 2 hours. After cooling, the solution is twice washed with 5 ml water, dried over magnesium sulphate and the solvent evaporated off under vacuum. After recrystallisation in ethyl alcohol and drying under vacuum one obtains 8-[N-(N',N'-diethylaminoethyl)-carboxamido]-3,5,7,3',4'-penta-O-benzyl-(+)-cyanidan-3-ol; m.p.: 149°–150° C.

EXAMPLE 107

A solution of 17.0 g 8-cyano-3,5,7,3',4'-penta-O-benzyl-(+)-cyanidan-3-ol in a mixture of 500 ml tetrahydrofuran and 500 ml methyl alcohol is hydrogenated over 10 g palladium 10% on activated charcoal. This lasts 8 hours. After the usual treatment (see example 1) 8-cyano-(+)-cyanidan-3-ol are obtained; decomposes at 250°–260° C.

EXAMPLE 108

A mixture of 5.0 g 8-(O-acetyloximino)-3,5,7,3',4'-penta-O-benzyl-(+)-cyanidan-3-ol and 50 ml acetic anhydride is reflux heated with stirring for 15 hours. The resulting solution is placed in 100 ml of a mixture of ice and water and stirred for 30 minutes. A yellow solid forms. This is filtered off and washed in water. After drying udner vacuum, one obtains 8-cyano-3,5,7,3',4'-penta-O-benzyl-(+)-cyanidan-2-ol in the form of a white solid; m.p.: 68°–69° C.

EXAMPLE 109

A mixture of 45.1 g 3,5,7,3',4'-bromo-penta-O-benzyl-(+)-cyanidan-3-ol, 5.91 g copper$^I$ cyanide and 28 ml dimethylformamide is reflux heated for 14 hours. It is allowed to cool to 70° C. and then 33 ml water and 11 ml ethylene diamine are added. 40 ml dimethylformamide is added and the mixture stirred for 1 hour at 40° C., allowed to cool to room temperature before adding to it 400 ml benzene and 15 ml water. The two phases are separated and the aqueous phase extracted 3 times with 50 ml benzene. The combined benzene phases are extracted with a solution of 12.5 g sodium cyanide in 250 ml water. The benzene is dried over magnesium sulphate and the solvent evaporated. After passing over a silicagel chromatographic column (eluent=chloroform) 8-cyano-3,5,7,3',4'-penta-O-benzyl-(+)-cyanidan-3-ol is isolated; m.p.: 68°–69° C.

EXAMPLE 110

20 g 8-formyloxy-3,5,7,3',4'-penta-O-methyl-(+)-cyanidan-3-ol is reflux dissolved in 300 ml methyl alcohol. After adding 0.1 g potassium, this is allowed to cool to room temperature. The crystals formed are separated and rinsed with a little cold methyl alcohol. In this way, one obtains colourless crystals of 8-hydroxy-3,5,7,3',4'-penta-O-methyl-(+)-cyanidan-3-ol; m.p.: 157°–158° C.

EXAMPLE 111

As in example 3, but after 10 minutes a cold solution of the lithium salt of tertiobutyl hydroperoxide is slowly added as follows: In a 250 ml flask, 6,8 g tertiobutyl hydroperoxide is dissolved in 100 ml anhydrous tetrahydrofuran. After cooling to −70° C., 51 ml of a 1.47M solution of n-butyl lithium in n-hexane are slowly added. Hydrolysis is carried out with 50 ml saturated ammonium chloride solution. The residue is crystallised in a mixture of ethyl alcohol and toluene to yield 8-hydroxy-3,5,7,3',4'-penta-O-benzyl-(+)-cyanidan-3-ol; m.p.: 94°–95° C.

EXAMPLE 112

20 g 8-formyloxy-3,5,7,3',4'-penta-O-benzyl-(+)-cyanidan-3-ol is reflux dissolved in 300 ml methyl alcohol. After the addition of 0.1 g potassium, this is allowed to cool to room temperature and completely evaporated after neutralisation of the mixture with several drops of formic acid. The residue is recrystallised in a mixture of ethyl alcohol and toluene to yield 8-hydroxy-3,5,7,3',4'-penta-O-benzyl-(+)-cyanidan-3-ol; same substance as that in example 111.

EXAMPLE 113

A solution of 30 g 8-methoxy-3,5,7,3',4'-penta-O-benzyl-(+)-cyanidan-3-ol in 500 ml ethyl acetate is hydrogenated over 10 g palladium 10% on activated charcoal. This process lasts 4 hours. After usual treatment (cf. example 1), 8-methoxy-(+)-cyanidan-3-ol in the form of a white solid is isolated; m.p.: 217° C.; $[\alpha]_D^{20} = -18.57°$ (C=0.5 in acetone).

EXAMPLE 114

A solution of 26.4 g 8-hydroxy-3,5,7,3',4'-penta-O-methyl-(+)-cyanidan-3-ol in 260 ml tetrahydrofuran is reflux heated under nitrogen over 7 g potassium hydride. After 1 hour, the suspension is allowed to cool and then 10 ml methyl iodide is added. After 30 minutes this is hydrolysed with a saturated solution of ammonium chloride. The resulting solution is extracted with methylene chloride and the organic phase washed with water and then dried. After evaporation the residue is recrystallised in methyl alcohol. In this way, one obtains 8-methoxy-3,5,7,3',4'-penta-O-methyl-(+)-cyanidan-3-ol; m.p.: 115°–117° C.

EXAMPLE 115

As in example 114, but starting with 28.4 g 8-formyloxy-3,5,7,3',4'-penta-O-methyl-(+)-cyanidan-3-ol. One obtains in the same way 8-methoxy-3,5,7,3',4'-penta-O-methyl-(+)-cyanidan-3-ol; same substance as that in example 114.

EXAMPLE 116

A solution of 52.6 g 8-hydroxy-3,5,7,3',4'-penta-O-benzyl-(+)-cyanidan-3-ol in 400 ml tetrahydrofuran is reflux heated under nitrogen over 7.2 g potassium hydride. After one hour the suspension is allowed to cool down and then a solution of 10 ml methyl iodide in 180 ml tetrahydrofuran is added. After 30 minutes, this is hydrolysed with saturated ammonium chloride solution and the solvent evaporated. The residue is cleared over a short silicagel column using methylene chloride. After evaopration the brown product obtained is recrystalised in a mixture of isopropyl ether and ethyl acetate. One obtains 8-methoxy-3,5,7,3',4'-penta-O-benzyl-(+)-cyanidan-3-ol; m.p.: 92°–94° C.

EXAMPLE 117

As in example 116, but starting with 54.5 g 8-formyloxy-3,5,7,3',4'-penta-O-benzyl-(+)-cyanidan-3-ol. One obtains 8-methoxy-3,5,7,3',4'-penta-O-benzyl-(+)-cyanidan-3-ol; same substance as that in example 116.

EXAMPLE 118

30 g 8-tertiobutoxy-3,5,7,3',4'-penta-O-benzyl-(+)-cyanidan-3-ol in 750 ml ethyl acetate are hydrogenated over 9 g palladium 10% on activated charcoal. This lasts 3 hours. After usual treatment (cf. example 1), one obtains 8-tertiobutoxy-(+)-cyanidan-3-ol in the form of a white solid; m.p.: 139°–140° C.; $[\alpha]_D^{20} = -10.0°$ (C=0.5, ethanol 95%).

EXAMPLE 119

A solution of 93.4 g 8-bromo-3,5,7,3',4'-penta-O-benzyl-(+)-cyanidan-3-ol in 500 ml tetrahydrofuran at −70° C. is treated with 81.7 ml of a 1.47M n-butyl lithium solution in n-hexane. 5 minutes later, 24.3 g magnesium bromide is added and the temperature allowed to rise to approximately 0° C. When the solution is complete the temperature is reduced to −60° C. and a solution of 25 ml tertiobutyl perbenzoate in 75 ml tetrahydrofuran is slowly added. The temperature is allowed to rise towards 0° C. and hydrolysis is carried out with 100 ml water. The solvent is evaporated off under vacuum (20°, 14 mm Hg) and the residue extracted with 500 ml methylene chloride. The organic phase is washed with a saturated solution of ammonium chloride then with water and finally dried. After evaporation, the residue obtained is recrystallised twice in a mixture of hexane and acetone. In this way, one obtains 8-tertiobutoxy-3,5,7,3',4'-penta-O-benzyl-(+)-cyanidan-3-ol in the form of a white solid; m.p.: 117°–118° C.; $[\alpha]_D^{20} = -40.0°$ (C=0.5 in acetone).

EXAMPLE 120

A solution of 18 g of 8-(2,3-epoxypropyloxy)-3,5,7,3',4'-penta-O-methyl-(+)-cyanidan-3-ol and 450 ml of a 0.1N potassium hydroxide aqueous solution in 800 ml of dimethylsulfoxide is stirred at 100° overnight. The reaction mixture is concentrated to 400 ml and one adds 1.2 liter of water. Extraction with dichloromethane and washing of the organic phase with water and drying over magnesium sulfate and evaporating the solvent give a crude yellow residue. This residue is purified by silica column chromatography using a mixture of methylene chloride and methanol for elution. The best fractions are recrystallised in isopropanol and give pure 8-(2,3-dihydroxy-propyloxy)-3,5,7,3',4'-penta-O-methyl-(+)-cyanidan-3-ol; m.p.: 119°–120°.

EXAMPLE 121

A solution of 10 g of 8-(2,3-epoxypropyloxy)-3,5,7,3',4'-penta-O-benzyl-(+)-cyanidan-3-ol and 140 ml of a 0.1N potassium hydroxide aqueous solution in 400 ml dimethylsulfoxide is stirred at 100° for 2 hours and then at room temperature for 48 h. Extraction with methylene chloride gives a solid residue which recrystallised in a mixture of ethanol and ethyl acetate. One obtains 8-(2,3-dihydroxypropyloxy)-3,5,7,3',4'-penta-O-benzyl-(+)-cyanidan-3-ol; m.p.: 127°–129°.

EXAMPLE 122

A mixture of 40.5 g of 8-formyloxy-3,5,7,3',4'-penta-O-methyl-(+)-cyanidan-3-ol, 6.8 g of tetrabutylammonium bisulphate and 0.4 liter of epichlorhydrin are efficiently stirred at room temperature for 90 minutes with 1 liter of a 50% aqueous sodium hydroxide solution. After addition of 0.6 liter of dichloromethane, the organic layer is separated, washed three times with 0.5 liter of water, dried over magnesium sulphate and evaporated. The oily residue is dissolved in 0.5 liter of ligroin at 75°. On cooling a solid forms which is separated and recristallised twice in ethanol. One obtains 8-(2,3-epoxypropyloxy)-3,5,7,3',4'-penta-O-methyl-(+)-cyanidan-3-ol as a white powder; m.p.: 104°–105° C.

EXAMPLE 123

A mixture of 108 g 8-formyloxy-3,5,7,3',4'-penta-O-benzyl-(+)-cyanidan-3-ol, 8.8 g tetrabutylammonium bisulphate and 1 liter of epichlorhydrin is efficiently stirred at room temperature for 90 min. with 1 liter of a 50% aqueous sodium hydroxide solution. After addition of 1.5 liter dichloromethane, the organic layer is separated, washed three times with 0.5 liter water, dried over magnesium sulphate and evaporated. The oily residue is dissolved in 0.5 liter ligroin at 75°. On cooling a solid forms which is separated and recrystallised in ethanol under nitrogen to give 8-(2,3-epoxypropyloxy)-3,5,7,3',4'-penta-O-benzyl-(+)-cyanidan-3-ol as a white powder; m.p.: 99°–101° C.

EXAMPLE 124

A solution of 25 g 8-(2,3-epoxypropyloxy)-3,5,7,3',4'-penta-O-methyl-(+)-cyanidan-3-ol in 500 ml isopropylamine is stirred and refluxed for 5 days. Isopropylamine is then distilled off and the oily residue dried under vacuum. After recrystallisation in a mixture of n-hexane and acetone, one obtains 8-(3-N-isopropylamino-2-hydroxypropyloxy)-3,5,7,3',4'-penta-O-methyl-(+)-cyanidan-3-ol as white crystals; m.p.: 105°–107° C.

EXAMPLE 125

A suspension of 1.23 g of 8-(3-N-isopropylamino-2-hydroxy-propyloxy)-3,5,7,3',4'-penta-O-methyl-(+)-cyanidan-3-ol and 0.58 g fumaric acid in 15 ml methanol is warmed at 55° C. overnight. On cooling crystals form. Recrystallisation in absolute ethanol give the hemifurmarate of 8-(3-N-isopropylamino-2-hydroxypropyloxy)-3,5,7,3',4'-penta-O-methyl-(+)-cyanidan-3-ol as white crystals; m.p.: 110°–112° C.

EXAMPLE 126

A solution of 40.65 g 8-(2,3-epoxypropyloxy)-3,5,7,3',4'-penta-O-benzyl-(+)-cyanidan-3-ol in 400 ml isopropylamine is refluxed under nitrogen for 45 hours. Ispropylamine is then diestilled off and the oil residue dried. After recrystallisation in isopropanol, one obtains 8-(3-N-isopropylamino-2-hydroxypropyloxy)-3,5,7,3',4'-penta-O-benzyl-(+)-cyanidan-3-ol as a white solid; m.p.: 114°–118° C.

EXAMPLE 127

A solution of 19.4 g 8-formyl-3,5,7,3',4'-penta-O-methyl-(+)-cyanidan-3-ol in 100 ml 1,2-dichloroethane is cooled in an ice bath. 2.5 g sodium acetate is added. A solution of 14.4 g 90% metachloroperbenzoic acid in 180 ml 1,2-dichloroethane is then slowly added keeping the temperature below 20° C. After heating for 1 hour at 60° C., then cooling, this is neutralised with a 5% sodium bicarbonate solution then washed in saturated sodium chloride solution. After drying over magnesium sulphate, the solvent is evaporated and the residue recrystallised in isopropyl alcohol. One obtains white needles of 8-formyloxy-3,5,7,3',4'-penta-O-methyl-(+)-cyanidan-3-ol; m.p.: 145°–147° C.

EXAMPLE 128

A solution of 77 g 8-formyl-3,5,7,3',4'-penta-O-benzyl-(+)-cyanidan-3-ol in 385 ml 1,2-dichloroethane is cooled in an ice bath. 9 g anhydrous sodium acetate is added. A solution of 28.8 g 90% mtachloroperbenzoic acid in 340 ml 1,2-dichloroethane is added slowly keeping the temperature below 20° C. After heating for 30 minutes at 50° C., then cooling again, this is neutralised with a 5% sodium bicarbonate solution then washed with a saturated salt solution. After drying over magnesium sulphate, the solution is filtered over florisil. After evaporation, one obtains 8-formyloxy-3,5,7,3',4'-penta-O-benzyl-(+)-cyanidan-3-ol; m.p.: 147° C.

EXAMPLE 129

A solution of 3.65 g 8-methoxy-3,5,7,3',4'-penta-O-methyl-(+)-cyanidan-3-ol and 7.2 ml dimethylformamide in 30 chloroform, under nitrogen, is cooled at 0°. One adds slowly 8.5 ml phosphoroxychloride and reflux heats this stirred mixture overnight. After cooling to 0° C. one adds carefully 40 ml of a 20% sodium acetate solution. Extraction with methylene chloride, washing of the organic phase with a 5% sodium bicarbonate solution and water, drying over magnesium sulphate and evaporation give a crude solid which is recrystallised in diisopropylether to give white crystals of pure 6-formyl-8-methoxy-3,5,7,3',4'-penta-O-methyl-(+)-cyanidan-3-ol: m.p.: 113°–114°.

EXAMPLE 130

A mixture of 45.7 g 8-boromo-3,5,7,3',4'-penta-O-benzyl-(+)-cyanidan-3-ol, 45.0 g bis-trifluoromethylthiomercury, 25.5 g powdered copper and 150 ml dry hexamethylphosphoramide is heated under a nitrogen cover at 170° C. for 9.5 hours. After cooling, the reaction mixture is poured into a stirred mixture of 250 ml toluene and 500 ml water. Filtration and washing of the solid material with toluene yield a clear liquid. The aqueous layer is separated and discarded. The toluene layer is washed three times with 500 ml water. After drying with sodium sulfate and evaporation, the crude product is purified by column chromatography on silicagel using toluene as eluent. After crystallisation from cyclohexane and drying under high vacuum 8-trifluoromethylthio-3,5,7,3',4'-penta-O-benzyl-(+)-cyanidan-3-ol is obtained as a white solid; m.p.: 115°–116° C.

EXAMPLE 131

A solution of 68 g 8-trifluoroacetyl-3,5,7,3',4'-penta-O-benzyl-(+)-cyanidan-3-ol in 400 ml ethyl acetate is hydrogenated, at 60° and atmospheric pressure, over 20 g palladium 10% on activated charcoal. This process lasts 2 hours. After usual treatment (cf. example 1), solid yellow 8-trifluoroacetyl-(+)-cyanidan-3-ol is isolated; m.p.: 220° C. (decomp.).

EXAMPLE 132

A suspension of 18 g palladium chloride in 2.5 liter methyl alcohol is hydrogenated. When the process is finished, the solution is decanted and rinsed several times in ethyl acetate. A solution of 15 g 8-trifluoroacetyl-3,5,7,3',4'-penta-O-benzyl-(+)-cyanidan-3-ol in 400 ml ethyl acetate is hydrogenated over this catalyst. This lasts for 6 hours. After usual treatment (cf. example 1), solid yellow 8-trifluoroacetyl-3-O-benzyl-(+)-cyanidan-3-ol is isolated; $[\alpha]_D^{20} = -50°$ (C=1 in 95% ethanol).

EXAMPLE 133

As in example 3, but after 10 minutes, a solution of 7.15 ml ethyl trifluoracetate in 15 ml tetrahydrofuran is added drop by drop. One hour later, the temperature is allowed to rise to 0° C. then hydrolysis carried out with 50 ml ammonium chloride solution. The tetrahydrofuran is evaporated off, then 500 ml dichloromethane is added. The solution obtained is washed with water, dried over magnesium sulphate then completely evaporated. It was not possible to recrystallise the residue but the latter may be purified by chromatography on a silicagel column using a 1:1 mixture of cyclohexane and isopropyl ether. In this way, one obtains 8-trifluoroacetyl-3,5,7,3',4'-penta-O-benzyl-(+)-cyanidan-3-ol as a slightly brown resin.

EXAMPLE 134

As in example 97, but reactor B contains 9.7 g tertiobutyl perbenzoate in 80 ml tetrahydrofuran. As it is not possible to crystallise the residue, this is separated by dry column chromatography of silicagel using a mixture of cyclohexane and diisopropyl ether as eluent. The first fraction obtained is 13 g (32%) of solid white 8-tertiobutoxy-3,5,7,3',4'-penta-O-benzyl-(+)-cyanidan-3-ol, which corresponds to the substance in example 119. Then by increasing the proportion of diisopropyl ether in the eluant one obtains 8-benzoyl-3,5,7,3',4'-penta-O-benzyl-(+)-cyanidan-3-ol in the form of a solid yellowish foam; m.p.: 55°–60° C.

EXAMPLE 135

To a solution of 4.48 g aniline in 44 ml 3N hydrochloric acid cooled to 0°–5° C., one adds slowly, in such a way that the temperature does not rise above 5° C., a solution of 9.6 g sodium nitrite in 32 ml water. This is stirred at 5° C. for 10 more minutes and then a solution of 4.8 g urea in 20 ml water is added. This solution is then added to a solution of 8.9 g 3',4'-O,O-diphenylmethylene (+)-cyanidan-3-ol in 520 ml 0.5N sodium hydroxide solution stirring rapidly at 3° C. The mixture is stirred for 2 hours at 3°–5° C., acidified with 80 ml 2N Hydrochloric acid, the red precipitate which forms filtered off and washed in water. The product is vacuum dried and recrystallised in a mixture of ethyl alcohol and acetone and then in a mixture of methyl alcohol and chloroform. After vacuum drying, one obtains 6,8-diphenylazo-3',4'-O,O-diphenylmethylene-(30)-cyanidan-3-ol; m.p.: 161°–162° C.

EXAMPLE 136

A suspension of 39 g 8-formyl-3,5,7,3',4'-penta-O-methyl-(+)-cyanidan-3-ol, 17 g L-cystein methyl ester hydrochlorid, 17 g sodium bicarbonate, 12 g magnesium sulphate in 500 ml methanol is stirred at room temperature under nitrogen for 2.5 hours. Filtration and vacuum concentration gives a residue which is dissolved in dichloromethane and chromatographed over silicagel, using a mixture of acetone and dichloromethane for elution. The best fractions give pure 8-3,5,7,3',4'-penta-O-methyl(carboxymethoxy-4-thaizolidin-2-yl)-(+)-cyanidan-3-ol as a resin.

EXAMPLE 137

3.5 g 8-formyl-3-O-formyl-5,7,3',4'-tetra-O-benzyl-(+)-cyanidan-3-ol dissolved in 50 ml tetrahydrofuran is hydrogenated during 45 minutes over 0.8 g palladium 5% on activated charcoal. After filtration of the catalyst and evaporation of the solvent, the residue is eluted on a dry silicagel column with a mixture of chloroform and ethyl acetate; 8-formyl-3-O-formyl-(+)-cyanidan-3-ol is obtained; m.p.: 124°-125° C.

EXAMPLE 138

As in example 22, but adding 9.42 g bromobenzene and a solution of 27.65 g 8-formyl-3-O-methyl-5,7,3',4'-tetra-O-benzyl-(+)-cyanidan-3-ol in 100 ml dry tetrahydrofuran. After hydrogenation in 300 ml ethyl acetate over 10% palladium on activated charcoal, filtration of the catalyst and evaporation of the solvent, the residual compound is purified by elution through a dry silicagel Woelm AIII column with a mixture of chloroform and ethyl acetate. One obtains 8-benzyl-3-O-methyl-(+)-cyanidan-3-ol. m.p.: 105° C.

EXAMPLE 139

30.0 g 8-formyl-(+)-cyanidan-3-ol is dissolved in 100 ml 1,2-dimethoxyethane. 15 ml pyridine is added followed by 22.7 g cupric acetate monohydrate in 50 ml 1,2-dimethoxyethane and the resulting mixture is stirred for 15 minutes. 30.0 g dichlorodiphenylmethane is added over 45 minutes at such a rate that the temperature does not rise over 35° C. The resultant mixture is then stirred for 4 hours at 20°-25° C. after which time the copper salts are removed by filtration. Evaporation of the filtrates affords a dark brown residue which is slurried with 250 ml ethyl acetate, then filtered. The filtrates are evaporated and the residue is treated with 500 ml dichloromethane, then filtered. The resulting solution is washed with a solution of ethylenediaminetetraacetic acid in water followed by a solution of borax in water. A precipitate is formed which is separated as well as the aqueous solution; the organic layer is washed with water and dried over magnesium sulphate. The solvent is evaporated and the residue is dissolved in diisopropyl ether, from which solution some tetraphenylethylene crystallises and is discarded. The solvent is again evaporated and the resulting compound is crystallised several times in a mixture of methanol and water. 3',4'-O,O-diphenylmethylene-8-formyl-(+)-cyanidan-3-ol is obtained. m.p.: 197°-198.5° C. The borax solution in water, which contains a precipitate, is neutralised with hydrochloric acid, then extracted with ethyl acetate. The organic phase is evaporated and the resulting residue is eluted on a dry silicagel Woelm AIII column with a mixture of toluene and diisopropylic ether to remove the 3',4'-O,O-diphenylmethylene-8-formyl-(+)-cyanidan-3-ol still contained in the residue. The other fraction is crystallised in a mixture of ethanol and water. One obtains 3,6'-O,C-diphenylmethylene-8-formyl-(+)-cyanidan-3-ol. m.p.: 300°-302° C.

EXAMPLE 140

As in example 139 using 32.7 g 8-formyl-3-O-formyl-(+)-cyanidan-3-ol. The dichloromethane solution extracted with aqueous borax is washed with water and dried over magnesium sulphate. The solvent is evaporated and the residue is eluted on a dry silicagel Woelm AIII column with a mixture of dichloromethane and ethyl acetate. One obtains 3',4'-O,O-diphenylmethylene-8-formyl-3-O-formyl-(+)-cyanidan-3-ol. m.p.: 117°-118° C.

We claim:

1. A pharmaceutical preparation for the treatment of a liver disease comprising a therapeutically effective amount of a compound of the formula

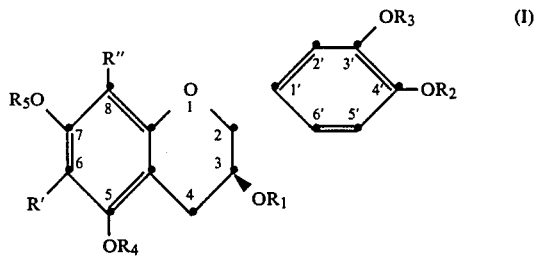

wherein R' is hydrogen, halogen, or $C_1$-$C_7$ alkylbenzyl; R" is $C_1$-$C_7$-alkyl which is substituted by hydroxyimino; $C_2$-$C_7$-alkenyl substituted by acetoxymethylthio; $C_1$-$C_7$-alkylbenzyl; formyl; or trifluoroacetyl; and $R_1$, $R_2$, $R_3$, $R_4$, and $R_5$ are each hydrogen, $C_1$-$C_7$-alkyl or phenyl-$C_1$-$C_7$-alkyl, and $R_1$ can also be $C_8$-$C_{16}$-alkanoyl; and a pharmaceutically acceptable carrier.

2. A pharmaceutical preparation for the treatment of a venous disease comprising a therapeutically effective amount of a compound of the formula

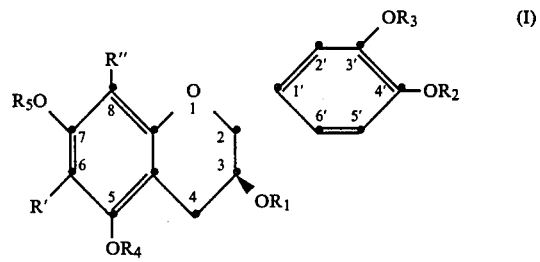

wherein R' is hydrogen, $C_1$-$C_7$ alkylbenzyl, or halobenzyl; R" is $C_1$-$C_4$-alkyl-benzyl, halobenzyl, or carboxyl; and $R_1$, $R_2$, $R_3$, $R_4$ and $R_5$ are each hydrogen, $C_1$-$C_7$-alkyl or phenyl-$C_1$-$C_7$-alkyl; or a pharmaceutically acceptable salt thereof, and a pharmaceutically acceptable carrier.

3. A pharmaceutical preparation for the treatment of a venous disease comprising a therapeutically effective amount of a compound selected from 8-(4-N,N-dimethylaminobenzyl)-3,5,7,3',4'-penta-O-methyl-(+)-cyanidan-3-ol, 6,8-di-(1-piperidyl-methyl)-3',4'-O,O-diphenylmethylene-(+)-cyanidan-3-ol, 6,8-di[phenyl-(1-piperidyl-methyl)]-3',4'-O,O-diphenylmethylene-(+)-cyanidan-3-ol, 8-formyl-3',4'-O,O-diphenylmethylene-(+)-cyanidan-3-ol, 8-formyl-3-O-formyl-3',4'-O,O-diphenylmethylene-(+)-cyanidan-3-ol, or a therapeutically active salt thereof and a pharmaceutically acceptable carrier.

4. A pharmaceutical preparation for the treatment of a venous disease comprising a therapeutically effective amount of a compound selected from 8-(4-methylbenzyl)-(+)-cyanidan-3-ol, 8-(2-methylbenzyl)-(+)-cyanidan-3-ol, 6,8-di(2-methylbenzyl)-(+)-cyanidan-3-ol, 8-(4-fluorobenzyl)-(+)-cyanidan-3-ol, 8-(4-methoxybenzyl)-(+)-cyanidan-3-ol, 8-benzyl-3-O-methyl-(+)-cyanidan-3-ol, 8-(4-fluorobenzyl)-3,5,7,3',4'-penta-O-methyl-(+)-cyanidan-3-ol, 8-(4-methylbenzyl)-3,5,7,3',4'-penta-O-methyl-(+)-cyanidan-3-ol, and a pharmaceutically acceptable carrier.

5. Pharmaceutical preparation for the treatment of liver diseases which contains 8-formyl-3-O-palmitoyl-(+)-cyanidan-3-ol and a pharmaceutically acceptable carrier.

6. Pharmaceutical preparation for the treatment of venous diseases according to claim 69 which contains 8-(4-methylbenzyl)-(+)-cyanidan-3-ol.

7. Pharmaceutical preparation for the treatment of venous diseases according to claim 4 which contains 8-(2-methylbenzyl)-(+)-cyanidan-3-ol.

8. Pharmaceutical preparation for the treatment of venous diseases according to claim 4 which contains 6,8-di-(2-methylbenzyl)-(+)-cyanidan-3-ol.

9. A pharmaceutical preparation for the treatment of venous diseases according to claim 4 which contains 8-(4-fluorobenzyl)-(+)-cyanidan-3-ol.

10. A pharmaceutical preparation for the treatment of venous diseases according to claim 4 which contains 8-(4-methoxybenzyl)-(+)-cyanidan-3-ol.

11. A pharmaceutical preparation for the treatment of venous diseases according to claim 4 which contains 8-benzyl-3-O-methyl-(+)-cyanidan-3-ol.

12. A pharmaceutical preparation for the treatment of venous diseases according to claim 4 which contains 8-(4-fluorobenzyl)-3,5,7,3',4'-penta-O-methyl-(+)-cyanidan-3-ol.

13. A pharmaceutical preparation for the treatment of venous diseases according to claim 4 which contains 8-(4-methylbenzyl)-3,5,7,3',4'-penta-O-methyl-(+)-cyanidan-3-ol.

14. A pharmaceutical preparation for the treatment of liver diseases which contains 8-formyl-3-O-palmitoyl-5,7,3',4'-tetra-O-benzyl-(+)-cyanidan-3-ol and a pharmaceutically acceptable carrier.

* * * * *